US005840521A

United States Patent [19]

Barth

[11] Patent Number: 5,840,521

[45] Date of Patent: Nov. 24, 1998

[54] EXPRESSION VECTOR CONTAINING AN INDUCIBLE SELECTION GENE SYSTEM

[75] Inventor: Peter Thomas Barth, Helsby, England

[73] Assignee: Imperial Chemical Industriles PLC, London, England

[21] Appl. No.: 338,793

[22] Filed: Nov. 8, 1994

Related U.S. Application Data

[63] Continuation of Ser. No. 842,081, Feb. 26, 1992, abandoned.

[30] Foreign Application Priority Data

Feb. 26, 1991 [GB] United Kingdom .................. 9104017
Apr. 29, 1991 [GB] United Kingdom .................. 9109188

[51] Int. Cl.[6] ........................ C12P 21/00; C12N 1/21; C12N 15/63

[52] U.S. Cl. .................. 435/69.1; 435/352.3; 435/320.1

[58] Field of Search ........................ 435/252.3, 252.33, 435/69.1, 172.1, 172.3, 183, 320.1; 536/23.2; 935/22, 24, 27, 38

[56] References Cited

U.S. PATENT DOCUMENTS

| | | | |
|---|---|---|---|
| 4,810,643 | 3/1989 | Souza | 435/69.5 |
| 4,894,334 | 1/1990 | Ben-Bassat et al. | 435/69.1 |

FOREIGN PATENT DOCUMENTS

| | | |
|---|---|---|
| 0169566 | 1/1986 | European Pat. Off. . |
| 0359379 | 3/1990 | European Pat. Off. . |
| 3934454 | 4/1991 | Germany . |
| 2052516 | 1/1981 | United Kingdom . |
| 8903886 | 5/1989 | WIPO . |

OTHER PUBLICATIONS

De La Torre et al.; "Plasmid Vectors Based on TN10 DNA; Gene Expression Regulated by Tetracycline[1]"; Plasmid vol. 12, No. 2, 1984; pp. 103–110.

Hillen et al.; "Tet Repressor–Tet Operator Interaction"; Topic Molecular Structure Biology, vol. 10; 1989 pp. 143–162.

Siebenlist et al.; "Contacts Between Escherichia coli RNA Polymerase and an Early Promoter of Phage T7"; Proceedings of the Nat'l Academy of Sciences of USA, vol. 77, No. 1; 1980; pp. 122–126.

Summers et al., "Multimerization of High Copy Number Plasmids Causes Instability . . . "; Cell, vol. 36, No. 4; 1984; pp. 1097–1103.

Bolivar et al.; "Construction and Characterization of New Cloning Vehicles . . . "; Gene; 1977; pp. 95–113.

Twigg et al.; "Trans–Complementable Copy–Number Mutants of Plasmid Cole1"; Nature; 1980; pp. 216–218.

Yanisch–Perron et al.; "Improved M13 Phage Cloning Vectors and Host Strains: Nucleotide Sequences of the M13MP18 and PUC19 Vectors"; Gene; 1985; pp. 103–119.

Lanka et al.; "Molecular Cloning and Mapping of SPH1 Restriction Fragments of Plasmid RP4"; Plasmid 10; 1983; pp. 303–307.

Datta et al.; "Properties of an R Factor from Pseudomonas Aeruginosa"; Journal of Bacteriology; 1971; pp. 1244–1249.

(List continued on next page.)

*Primary Examiner*—George C. Elliott
*Assistant Examiner*—Robert Schwartzman
*Attorney, Agent, or Firm*—Cushman Darby & Cushman Intellectual Property Group of Pillsbury Madison & Sutro, LLP

[57] ABSTRACT

The invention relates to vectors which include an inducible selection gene and a sequence which codes for a heterologous polypeptide. In a particular example the selection gene comprises the tetA and tetR genes. The vector may also include a sequence which is capable of conferring stability on the vector, such as the cer sequence, a transcription terminator, such as gene 32 from bacteriophage T4, a ribosome binding site, and a multi-cloning site. Hosts transformed with the vector, processes for preparing these hosts, and processes for preparing polypeptides using these hosts.

19 Claims, 25 Drawing Sheets

OTHER PUBLICATIONS

Klock et al.; "Heterologous Repressor–Operator Recognition Among Four Classes of Tetracycline Resistance Determinants"; American Society for Microbiology; 1985; pp. 326–332.

Barth et al.; "Map of Plasmid RP4 Derived by Insertion of Transposon C"; Journal of Molecular Biology; 1977; pp. 455–474.

Holmes et al.; "A Rapid Boiling Method for the Preparation of Bacterial Plasmids"; Analytical Biochemistry; 1981; pp. 193–197.

Welte et al.; "Purification and Biochemical Characterization of Human Pluripotent Hematopoietic Colony–Stimulating Factor"; Proc. Nat'l. Acad. Sci. USA 82; 1985; pp. 1526–1530.

Summers et al.; "Multimer Resolution Systems of Cole1 and COLK; Localisation of the Crossover Site"; Mol. Gen. Genet; 1985; pp. 334–338.

Moyed et al. (1980), Journal of Bacteriology, vol. 15, No. 2, pp. 549–556.

McMurray et al. (1980) Proceedings of the National Academy of Sciences, vol. 77, No. 7, pp. 3974–3977.

Sambrook et al. (1989) Molecular Cloning: A Laboratory Manual (Cold Spring Harbor Laboratry Press, Cold Spring Harbor), pp. 1.3–1.20, 17.3–17.41.

Gorski et al. (1985) Cell, vol. 43, No. 2, pp. 461–470.

Hsien et al. (1976) Biochemistry, vol. 15, No. 26, pp. 5776–5783.

Lamb et al. (1985) European Journal of Biochemistry, vol. 148, pp. 265–270.

TRANSCRIPTION TERMINATION SEQUENCE

Fig. 1(a)

```
  SalI
5' TCGACATTATATTACTAATTAATTGGGGACCCTAGAGGTCCCCTTTTTTATTTTAA
3'      GTAATATAATGATTAATTAACCCCTGGGATCTCCAGGGGAAAAAATAAAATT

    SphI HindIII
   AAAGCATGCA           3'
   TTTCGTACGTTCGA       5'
```

Fig. 1(b)

```
  SalI
5' TCGACATTATATTACTAATTAATTGGGGACCCTAGAGGTCCCCTTTTTTATTTTAA
3'      GTAATATAATGATTAATTAACCCCTGGGATCTCCAGGGGAAAAAATAAAATT

    SphI BamHI  StyI
   AAAGCATGCGGATCCC       3'
   TTTCGTACGCCTAGGGGAAC   5'
```

Fig.5(a)

```
EcoR1
AATTCTGGCA AATATTCTGA AATGAGCTGT TGACAATTAA TCATCGAACT    50
    GACCGT TTATAAGACT TTACTCGACA ACTGTTAATT AGTAGCTTGA    46

   HpaI
AGTTAACTAG TACGCAAGTT CACGTAAAAA GGGTATCGAC               90
TCAATTGATC ATGCGTTCAA GTGCATTTTT CCCATAGCTG               86

    KpnI      BamHI    XbaI     SalI     PstI     SphI
AATGGTACCC GGGGATCCTC TAGAGTCGAC CTGCAGGCAT GCAAGCTTAG   140
TTACCATGGG CCCCTAGGAG ATCTCAGCTG GACGTCCGTA CGTTCGAATC   136

                                ClaI
CCCGCCTAAT GAGCGGGCTT TTTTTTAT                           168
GGGCGGATTA CTCGCCCGAA AAAAAATAGC                         166
```

Fig.5(b)

```
EcoRI
AATTCTGGCA AATATTCTGA AATGAGCTGT TGACAATTAA TCATCGAACT

 HpaI
AGTTAACTAG TACGCAGAGC TCAATCTAGA GGGTATTAAT AATGTTCCCA

TTGGAGGATG ATTAATG
```

Fig. 9A

```
EcoRI   ScaI

AATTCAGT ACT CCA CTG GGT CCA GCA AGC TCT CTG CCG CAG TCT TTC CTG CTG AAG TCT    59
    GTCA TGA GGT GAC CCA GGT CGT TCG AGA GAC GGC GTC AGA AAG GAC GAC TTC AGA
         Thr Pro Leu Gly Pro Ala Ser Ser Leu Pro Gln Ser Phe Leu Leu Lys Ser
          1               5                  10                  15
             SnabI                                                    FspI

CTC GAA CAG GTA CGT AAA ATT CAA GGC AGC GGT GCG GCT CTG CAG GAA AAG CTG TGC GCA 119
GAG CTT GTC CAT GCA TTT TAA GTT CCG TCG CCA CGC CGA GAC GTC CTT TTC GAC ACG CGT
Leu Glu Gln Val Arg Lys Ile Gln Gly Ser Gly Ala Ala Leu Gln Glu Lys Leu Cys Ala
         20                  25                  30                  35
                         MstII                                      BamHI

ACC TAC AAA CTG TGC CAC CCT GAG GAA CTG GTG CTG CTC GGT CAC TCT CTG GGG ATC CCG 179
TGG ATG TTT GAC ACG GTG GGA CTC CTT GAC CAC GAC GAG CCA GTG AGA GAC CCC TAG GGC
Thr Tyr Lys Leu Cys His Pro Glu Glu Leu Val Leu Leu Gly His Ser Leu Gly Ile Pro
         40                  45                  50                  55
             SacI                   HindIII

TGG GCT CCA CTG AGC TCT TGC CCG TCC CAA GCT TTA CAA CTG GCA GGC TGC TTG AGC CAG 219
ACC CGA GGT GAC TCG AGA ACG GGC AGG GTT CGA AAT GTT GAC CGT CCG ACG AAC TCG GTC
Trp Ala Pro Leu Ser Ser Cys Pro Ser Gln Ala Leu Gln Leu Ala Gly Cys Leu Ser Gln
         60                  65                  70                  75
                                                    XbaI

CTG CAC TCC GGT CTG TTC CTG TAC CAG GGT CTG CTG CAG GCT CTA GAA GGC ATC TCT CCT 299
GAC GTG AGG CCA GAC AAG GAC ATG GTC CCA GAC GAC GTC CGA GAT CTT CCG TAG AGA GGA
Leu His Ser Gly Leu Phe Leu Tyr Gln Gly Leu Leu Gln Ala Leu Glu Gly Ile Ser Pro
         80                  85                  90                  95
```

*Fig. 9B*

```
                                                                    NdeI
GAA TTG GGG CCC ACC CTG GAC ACA CTG CAG CTG GAC GTT GCC GAC TTC GCT ACT ACC ATA 359
CTT AAC CCC GGG TGG GAC CTG TGT GAC GTC GAC CTG CAA CGG CTG AAG CGA TGA TGG TAT
Glu Leu Gly Pro Thr Leu Asp Thr Leu Gln Leu Asp Val Ala Asp Phe Ala Thr Thr Ile
        100                 105                 110                 115

TGG CAA CAG ATG GAG GAA CTG GGT ATG GCT CCG GCA CTG CAG CCG ACT CAG GGT GCG ATG 419
ACC GTT GTC TAC CTC CTT GAC CCA TAC CGA GGC CGT GAC GTC GGC TGA GTC CCA CGC TAC
Trp Gln Gln Met Glu Glu Leu Gly Met Ala Pro Ala Leu Gln Pro Thr Gln Gly Ala Met
        120                 125                 130                 135
                                        BssHII

CCA GCA TTC GCC TCT GCT TTC CAG CGG CGC GCA GGC GGT GTT CTG GTT GCC TCC CAT CTT 479
GGT CGT AAG CGG AGA CGA AAG GTC GCC GCG CGT CCG CCA CAA GAC CAA CGG AGG GTA GAA
Pro Ala Phe Ala Ser Ala Phe Gln Arg Arg Ala Gly Gly Val Leu Val Ala Ser His Leu
        140                 145                 150                 155

            XhoI                                                        SalI
CAG AGC TTC CTC GAG GTG TCT TAC CGC GTT CTG CGT CAC CTG GCC CAG CCG TAA G       534
GTC TCG AAG GAG CTC CAC AGA ATG GCG CAA GAC GCA GTG GAC CGG GTC GGC ATT CAGCT
Gln Ser Phe Leu Glu Val Ser Tyr Arg Val Leu Arg His Leu Ala Gln Pro
        160                 165                 170             174
```

Fig. 10A

```
EcoRI   ScaI

AATTCAGT ACT CCA CTG GGT CCA GCA AGC TCT CTG CCG CAG TCT TTC CTG CTG AAG TGT     59
    GTCA TGA GGT GAC CCA GGT CGT TCG AGA GAC GGC GTC AGA AAG GAC GAC TTC ACA
         Thr Pro Leu Gly Pro Ala Ser Ser Leu Pro Gln Ser Phe Leu Leu Lys Cys
          1               5                  10                  15
               SnabI                                                  PspI

CTC GAA CAG GTA CGT AAA ATT CAA GGC GAT GGT GCG GCT CTG CAG GAA AAG CTG TGC GCA 119
GAG CTT GTC CAT GCA TTT TAA GTT CCG CTA CCA CGC CGA GAC GTC CTT TTC GAC ACG CGT
Leu Glu Gln Val Arg Lys Ile Gln Gly Asp Gly Ala Ala Leu Gln Glu Lys Leu Cys Ala
        20                  25                  30                  35
                         MstII                                    BamHI

ACC TAC AAA CTG TGC CAC CCT GAG GAA CTG GTG CTG CTC GGT CAC TCT CTG GGG ATC CCG 179
TGG ATG TTT GAC ACG GTG GGA CTC CTT GAC CAC GAC GAG CCA GTG AGA GAC CCC TAG GGC
Thr Tyr Lys Leu Cys His Pro Glu Glu Leu Val Leu Leu Gly His Ser Leu Gly Ile Pro
        40                  45                  50                  55
              SacI                   HindIII

TGG GCT CCA CTG AGC TCT TGC CCG TCC CAA GCT TTA CAA CTG GCA GGC TGC TTG AGC CAG 219
ACC CGA GGT GAC TCG AGA ACG GGC AGG GTT CGA AAT GTT GAC CGT CCG ACG AAC TCG GTC
Trp Ala Pro Leu Ser Ser Cys Pro Ser Gln Ala Leu Gln Leu Ala Gly Cys Leu Ser Gln
        60                  65                  70                  75
                                                    XbaI

CTG CAC TCC GGT CTG TTC CTG TAC CAG GGT CTG CTG CAG GCT CTA GAA GGC ATC TCT CCT 299
GAC GTG AGG CCA GAC AAG GAC ATG GTC CCA GAC GAC GTC CGA GAT CTT CCG TAG AGA GGA
Leu His Ser Gly Leu Phe Leu Tyr Gln Gly Leu Leu Gln Ala Leu Glu Gly Ile Ser Pro
        80                  85                  90                  95
```

Fig. 10B

```
                                                                                 NdeI
GAA TTG GGG CCC ACC CTG GAC ACA CTG CAG CTG GAC GTT GCC GAC TTC GCT ACT ACC ATA 359
CTT AAC CCC GGG TGG GAC CTG TGT GAC GTC GAC CTG CAA CGG CTG AAG CGA TGA TGG TAT
Glu Leu Gly Pro Thr Leu Asp Thr Leu Gln Leu Asp Val Ala Asp Phe Ala Thr Thr Ile
        100                 105                 110                 115

TGG CAA CAG ATG GAG GAA CTG GGT ATG GCT CCG GCA CTG CAG CCG ACT CAG GGT GCG ATG 419
ACC GTT GTC TAC CTC CTT GAC CCA TAC CGA GGC CGT GAC GTC GGC TGA GTC CCA CGC TAC
Trp Gln Gln Met Glu Glu Leu Gly Met Ala Pro Ala Leu Gln Pro Thr Gln Gly Ala Met
        120                 125                 130                 135
                                      BssHII
CCA GCA TTC GCC TCT GCT TTC CAG CGG CGC GCA GGC GGT GTT CTG GTT GCC TCC CAT CTT 479
GGT CGT AAG CGG AGA CGA AAG GTC GCC GCG CGT CCG CCA CAA GAC CAA CGG AGG GTA GAA
Pro Ala Phe Ala Ser Ala Phe Gln Arg Arg Ala Gly Gly Val Leu Val Ala Ser His Leu
        140                 145                 150                 155
            XhoI                                                            SalI

CAG AGC TTC CTC GAG GTG TCT TAC CGC GTT CTG CGT CAC CTG GCC CAG CCG TAA G       534
GTC TCG AAG GAG CTC CAC AGA ATG GCG CAA GAC GCA GTG GAC CGG GTC GGC ATT CAGCT
Gln Ser Phe Leu Glu Val Ser Tyr Arg Val Leu Arg His Leu Ala Gln Pro
        160                 165                 170             174
```

Fig. 18A

```
                         Trp Promoter
      TTCTGGCAAATATTCTGAAATGAGCTGTTGACAATTAATCATCGAACTAGTTAACTAGTA
    1 ---------+---------+---------+---------+---------+---------+ 60

                         S-D    rbs   Met KpnI     BamHI
      CGCAAGTTCACGTAAAAAGGGTATCGACAATGGTACCCGGGGATCCACCTCAGGGTGGTC
   61 ---------+---------+---------+---------+---------+---------+ 120

             Stop             KpnI        ----Ricin A----->
      TTTCACATTAGAGGATAACAACATGGTACCCAAACAATACCCAATTATAAACTTTACCAC
  121 ---------+---------+---------+---------+---------+---------+ 180
                              M  V  P  K  Q  Y  P  I  I  N  F  T  T

      AGCGGGTGCCACTGTGCAAAGCTACACAAACTTTATCAGAGCTGTTCGCGGTCGTTTAAC
  181 ---------+---------+---------+---------+---------+---------+ 240
       A  G  A  T  V  Q  S  Y  T  N  F  I  R  A  V  R  G  R  L  T

      AACTGGAGCTGATGTGAGACATGAAATACCAGTGTTGCCAAACAGAGTTGGTTTGCCTAT
  241 ---------+---------+---------+---------+---------+---------+ 300
       T  G  A  D  V  R  H  E  I  P  V  L  P  N  R  V  G  L  P  I

      AAACCAACGGTTTATTTTAGTTGAACTCTCAAATCATGCAGAGCTTTCTGTTACATTAGC
  301 ---------+---------+---------+---------+---------+---------+ 360
       N  Q  R  F  I  L  V  E  L  S  N  H  A  E  L  S  V  T  L  A

      CCTGGATGTCACCAATGCATATGTGGTCGGCTACCGTGCTGGAAATAGCGCATATTTCTT
  361 ---------+---------+---------+---------+---------+---------+ 420
       L  D  V  T  N  A  Y  V  V  G  Y  R  A  G  N  S  A  Y  F  F

      TCATCCTGACAATCAGGAAGATGCAGAAGCAATCACTCATCTTTTCACTGATGTTCAAAA
  421 ---------+---------+---------+---------+---------+---------+ 480
       H  P  D  N  Q  E  D  A  E  A  I  T  H  L  F  T  D  V  Q  N

      TCGATATACATTCGCCTTTGGTGGTAATTATGATAGACTTGAACAACTTGCTGGTAATCT
  481 ---------+---------+---------+---------+---------+---------+ 540
       R  Y  T  F  A  F  G  G  N  Y  D  R  L  E  Q  L  A  G  N  L

      GAGAGAAAATATCGAGTTGGGAAATGGTCCACTAGAGGAGGCTATCTCAGCGCTTTATTA
  541 ---------+---------+---------+---------+---------+---------+ 600
       R  E  N  I  E  L  G  N  G  P  L  E  E  A  I  S  A  L  Y  Y

      TTACAGTACTGGTGGCACTCAGCTTCCAACTCTGGCTCGTTCCTTTATAATTTGCATCCA
  601 ---------+---------+---------+---------+---------+---------+ 660
       Y  S  T  G  G  T  Q  L  P  T  L  A  R  S  F  I  I  C  I  Q
```

*Fig. 18B*

```
      AATGATTTCAGAAGCAGCAAGATTCCAATATATTGAGGGAGAAATGCGCACGAGAATTAG
661   ---------+---------+---------+---------+---------+---------+ 720
       M  I  S  E  A  A  R  F  Q  Y  I  E  G  E  M  R  T  R  I  R

      GTACAACCGGAGATCTGCACCAGATCCTAGCGTAATTACACTTGAGAATAGTTGGGGGAG
721   ---------+---------+---------+---------+---------+---------+ 780
       Y  N  R  R  S  A  P  D  P  S  V  I  T  L  E  N  S  W  G  R

      ACTTTCCACTGCAATTCAAGAGTCTAACCAAGGAGCCTTTGCTAGTCCAATTCAACTGCA
781   ---------+---------+---------+---------+---------+---------+ 840
       L  S  T  A  I  Q  E  S  N  Q  G  A  F  A  S  P  I  Q  L  Q

      AAGACGTAATGGTTCCAAATTCAGTGTGTACGATGTGAGTATATTAATCCCTATCATAGC
841   ---------+---------+---------+---------+---------+---------+ 900
       R  R  N  G  S  K  F  S  V  Y  D  V  S  I  L  I  P  I  I  A

      TCTCATGGTGTATAGATGCGCACCTCCACCATCGTCACAGTTTTGATTGCTTATAAGGCC
901   ---------+---------+---------+---------+---------+---------+ 960
       L  M  V  Y  R  C  A  P  P  P  S  S  Q  F  *

         KpnI            XbaI          PstI  SphI HindIII
      AGTGGTACCCGGGGATCCTCTAGAGTCGACCTGCAGGCATGCAAGCTTAGCCCGCCTAAT
961   ---------+---------+---------+---------+---------+---------+1020

        Terminator
      GAGCGGGCTTTTTTTTATCGACCGATGCCCTTGAGAGCCTTCAACCCAGTCAGCTCCTTC
1021  ---------+---------+---------+---------+---------+---------+1080

      CGGTGGGCGCGGGGCATGACTATCGTCGCCGCACTTATGACTGTCTTCTTTATCATGCAA
1081  ---------+---------+---------+---------+---------+---------+1140
```

EXPRESSION VECTOR CONTAINING AN INDUCIBLE SELECTION GENE SYSTEM

This is a continuation if application Ser. No. 07/842,081, filed on Feb. 26, 1992; which was abandoned.

The present invention relates to a vector which includes an inducible selection gene, a host containing the vector and processes for preparing the vector and host.

The majority of bacterial cloning and expression vectors contain an antibiotic resistance marker as a simple means to maintain selection for the plasmid in the bacterial host of choice. This is commonly ampicillin because of the fact that one of the original cloning vectors constructed, pBR322, carries an ampicillin resistance determinant (Bolivar et al, 1977, *Gene* 2: 95–113). One of the derivatives of this plasmid is pAT153 (Twigg and Sherratt, 1980, Nature 283: 216–218). The ampicillin resistance marker is constitutively controlled as are the majority of plasmid encoded resistances.

Although a number of selection systems have been used in cloning vectors for the preparation of polypeptides, there is still a need for improved selection systems.

According to the present invention there is provided a vector which comprises an inducible selection gene, and a sequence which codes for a heterologous polypeptide.

The term "vector" as used herein is used in its broadest sense and includes within its meaning any replicon capable of transferring recombinant DNA material from one cell to another. The present invention includes vectors suitable for integration into a host, and vectors, such as plasmids, which are useful in constructing vectors for transfer of recombinant DNA to hosts.

The inducible "selection gene" (or selection marker) will, in general, include a gene which facilitates selection and is inducible. The inducible selection gene may comprise a first gene which codes for a substance which facilitates selection, and a second gene which controls expression of that substance so that expression only occurs under defined conditions. Thus, for example the first gene may comprise a gene which codes for a substance which confers resistance to an antibiotic and the second gene may comprise a gene which codes for a repressor. In the presence of the antibiotic the system is induced and expression of the first gene takes place to confer antibiotic resistance, thus permitting recombinant vectors which carry the selection gene to be selected. In the absence of the antibiotic, repression occurs so that expression of the first gene does not take place and the substance which confers antibiotic resistance in the vector is not produced.

A particular example of a suitable inducible selection gene is one which includes the tetA and tetR genes. The tetA gene is the gene which codes for a substance which confers resistance to tetracycline; whilst the tetR gene codes for a repressor protein which is able to prevent expression of the tetA gene. The system is induced in the presence of tetracycline, so that in its presence the tetA gene is expressed thus conferring tetracycline resistance on the vectors which carry the selection gene. In the absence of tetracycline, the tetA gene is repressed by the tetR gene so that expression of tetA does not take place and the product of this gene is not generated.

Thus in particular embodiment of the present invention there is provided a vector which comprises an inducible selection gene which comprises the tetA and tetR genes, and a sequence which codes for a heterologous polypeptide.

The vector may, in addition to the sequences mentioned above include other DNA sequences suitable for particular applications, such as appropriate control sequences. For example the vector may include a promoter, ribosome binding site and transcription terminator sequence. The vector will, in general, include an origin of replication, for example that derived from plasmid pAT153.

A particular example of a suitable promoter is the tryptophan (trp) promoter. Other promoters may be used. For example, in a further embodiment of the present invention the vector includes the T7A3 promoter (SEQ ID NO 42), in which case the vector may optionally also include an operator such as lac0 (especially the shortened lac0 sequence of SEQ ID NO 43). The T7A3 promoter sequence shown in SEQ ID NO 42 is shown up to the base before the beginning of mRNA, so that when used with the lac0 sequence the lac0 sequence of SEQ ID NO 43 extends from +1 (beginning of mRNA).

A particular example of a transcription terminator is a derivative of the transcription terminator sequence found in bacteriophage T4 gene 32.

A sequence which confers stability on the vector may also be present. An example of such a sequence is the cer sequence (see, for example, Cell, 36, 1097–1103, 1984).

The vector may include a multicloning sequence to facilitate the introduction of ribosome binding sequences, and genes for heterologous polypeptides etc.

The heterologous polypeptide may comprise a polypeptide which possesses pharmacological properties, and is hence of use in medicine. A particular example of such a polypeptide is ricin A which may be used in the preparation of immunotoxins. A further example is a polypeptide known as G-CSF or an analogue thereof.

Granulocyte colony stimulating factor (G-CSF) has been described in the literature by Wallet K. et al Proc. Natl. Acad. Sci. USA Vol 82, pp 1526–1530 and has also been described in European Patent Publication No 169,566 and PCT Patent Publication No WO 87/01132. G-CSF has been shown to stimulate granulocyte production in vivo and to function with minimal side effects. As a result human G-CSF is seen as having potential utility in the management of neutropaenia associated with chemotherapy, radiation therapy, radiation accident or autologous bone marrow transplantation. Moreover G-CSF may have utility in the stimulation of bone marrow suppression associated with AIDS, in the treatment of myelodysplastic syndromes characterised by granulocyte functional abnormalities and as an adjunct to the treatment of severe infections.

The term "human G-CSF" as used herein refers to those G-CSFs that have been found to exist in nature and includes the two polypeptides having the amino acid sequence set out in SEQ. ID No 41. These two polypeptides differ only in so far as a tripeptide insert Val-Ser-Glu is present in one polypeptide between positions 35 and 36, but absent in the other. The numbering used throughout the present specification is based on the naturally occurring polypeptide without the Val-Ser-Glu insert.

Analogues of G-CSF include polypeptides which differ from that of naturally occurring G-CSFs in terms of the identity or location of one or more amino acid residues. For example, such analogues may contain substitutions, or terminal or intermediate additions or deletions of such residues. Such analogues would share the property of natural G-CSFs of being able to stimulate granulocyte production.

In particular the present invention provides a replicable expression vehicle which comprises a vector as hereinbefore defined.

In a particular embodiment of the present invention there is provided a replicable plasmidic expression vehicle which comprises an inducible selection gene comprising the tetA and tetR genes, and a DNA sequence which codes for a heterologous polypeptide.

As indicated above, the expression vehicle may include a sequence capable of conferring stability on the expression vehicle, such as the cer sequence.

In a further embodiment of the present invention there is provided a vector which comprises a replicable plasmidic expression vehicle comprising a promoter, the cer sequence, a transcription terminator as found in the terminus of gene 32 bacteriophage T4, an origin of replication and a DNA sequence which codes for a heterologous polypeptide.

According to the present invention there is also provided a process for preparing a polypeptide, said process comprising culturing a host which comprises a vector of the present invention so that the polypeptide is expressed.

The process may be carried out in the absence of the product used in selection. For example, in the case where the selection system comprises the tetA and tetR genes, the process may be carried out in the absence of tetracycline.

The above-mentioned process may be effected by the use of any appropriate host cell, such as bacterial, yeast, or mammmalian cells. A particular example of a suitable host comprises bacterial cells, for example *E. coli.*

It will be appreciated that where the desired metabolite is not passed out of the host at a useful rate, the host may be cultured and harvested as the intact cell and the desired polypeptide recovered by subsequently extracting the cells, for example after separation from the medium containing nutrients necessary for growth of the host cell. Where the metabolite is passed out of the host cell into the surrounding culture solution, then the polypeptide may be recovered by extraction in the normal way.

According to the present invention there is also provided a host capable of expressing a heterologous polypeptide, which host comprises a vector (such as replicable plasmidic expression vehicle) as herein defined.

In a particular embodiment of the present invention there is provided a host transformed with a replicable plasmidic expression vehicle which comprises an inducible selection gene comprising the tetA and tetR genes, and a DNA sequence which codes for a heterologous polypeptide.

According to a further feature of the present invention there is also provided a process for the preparation of a host as hereinbefore defined, said process comprising transforming a host by the insertion therein of a vector (such as a replicable plasmidic expression vehicle) as hereinbefore defined.

Suitable methods for the introduction of foreign genetic material into a host are known from the literature. Such methods include formation of a replicable expression vehicle comprising a vector and the foreign genetic material, and introduction of the vehicle into the host. Introduction of the vehicle into the host may be facilitated by subjecting the host to an appropriate treatment, for example in the case of *E. coli*, by treatment with calcium chloride solution.

The present invention also provides a process for the preparation of a vector as herein defined comprising inserting a sequence which codes for the desired polypeptide into a vector (as herein defined) at an appropriate insertion site so that a vector (conveniently in the form of a replicable plasmidic expression vehicle) is obtained which is capable of directing synthesis of the polypeptide.

According to a further aspect of the present invention there is provided a vector which comprises an inducible selection gene. The selection gene may be as defined hereinbefore, for example it may comprise the tetA and tetR genes.

The vector of the present invention utilises an inducible selection gene. This has been found to be particularly advantageous since the product of this gene (tetA in the preferred embodiment) is only expressed during the construction and testing phases of the genetic manipulation. If the subsequent plasmid carrying the cloned gene is stably maintained in its bacterial host, the need for selection ceases. Cultures grown to express the cloned gene product will therefore not require addition of the selection drug and will consequently not express the product of the selection gene. Such a product is unavoidable in most vectors because they carry constitutively expressed selection genes. Such unwanted products are disadvantageous because they divert metabolic energy away from the cloned gene product and may produce undesirable contaminants. In particular the vectors of the present invention avoids the use of penicillins as selection markers. This is particularly advantageous because of the prevalence of allergic reactions to penicillin or its breakdown products in human populations. Presence of a β-lactamase encoded by the plasmid would prevent the simple detection of any such contaminating β-lactams as active antibiotics.

The use of the tetA/tetR genes as a selection system has been found to particularly advantageous as, in general, the vectors which contain this selection system are unexpectedly stable. This stability helps to maintain expression levels and to improved accumulation of polypeptides, such as ricin A.

The stability of the vectors of the present invention is exemplified by pICI0042 which carries the tetA/tetR selection gene. This plasmid was unexpectedly found to have gained stability over its parent pAT153, even without the presence of the cer sequence. This is an unexpected but very welcome advantage of the construction of this plasmid.

The invention will now be further described, by way of example only, with reference to the following Examples; and accompanying drawings in which:

FIGS. 1(*a*) and (*b*) illustrate transcription terminator sequences (SEQ ID NOS: 33, 37, 49, 52);

Figure 6:
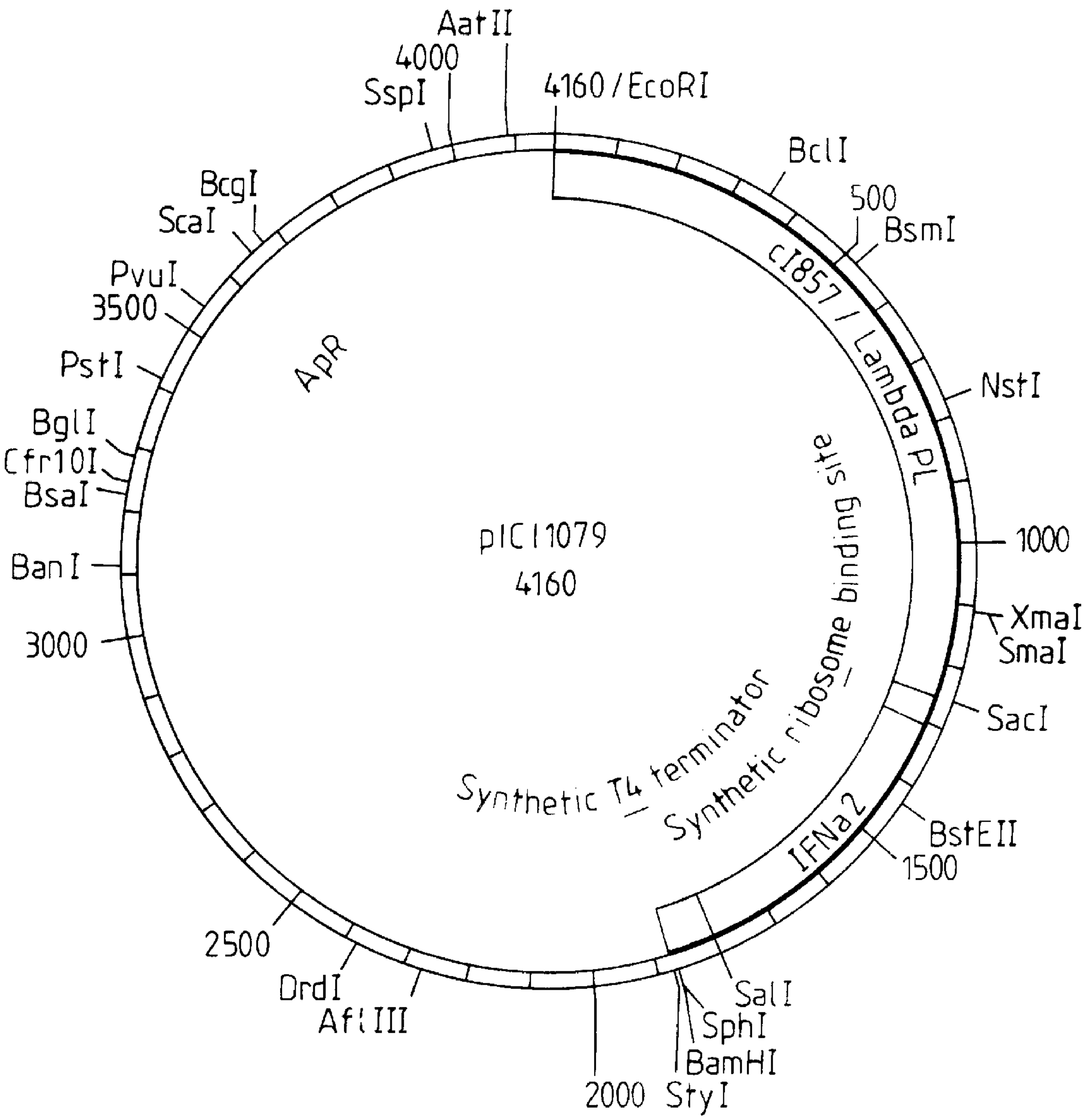
Figure 7:
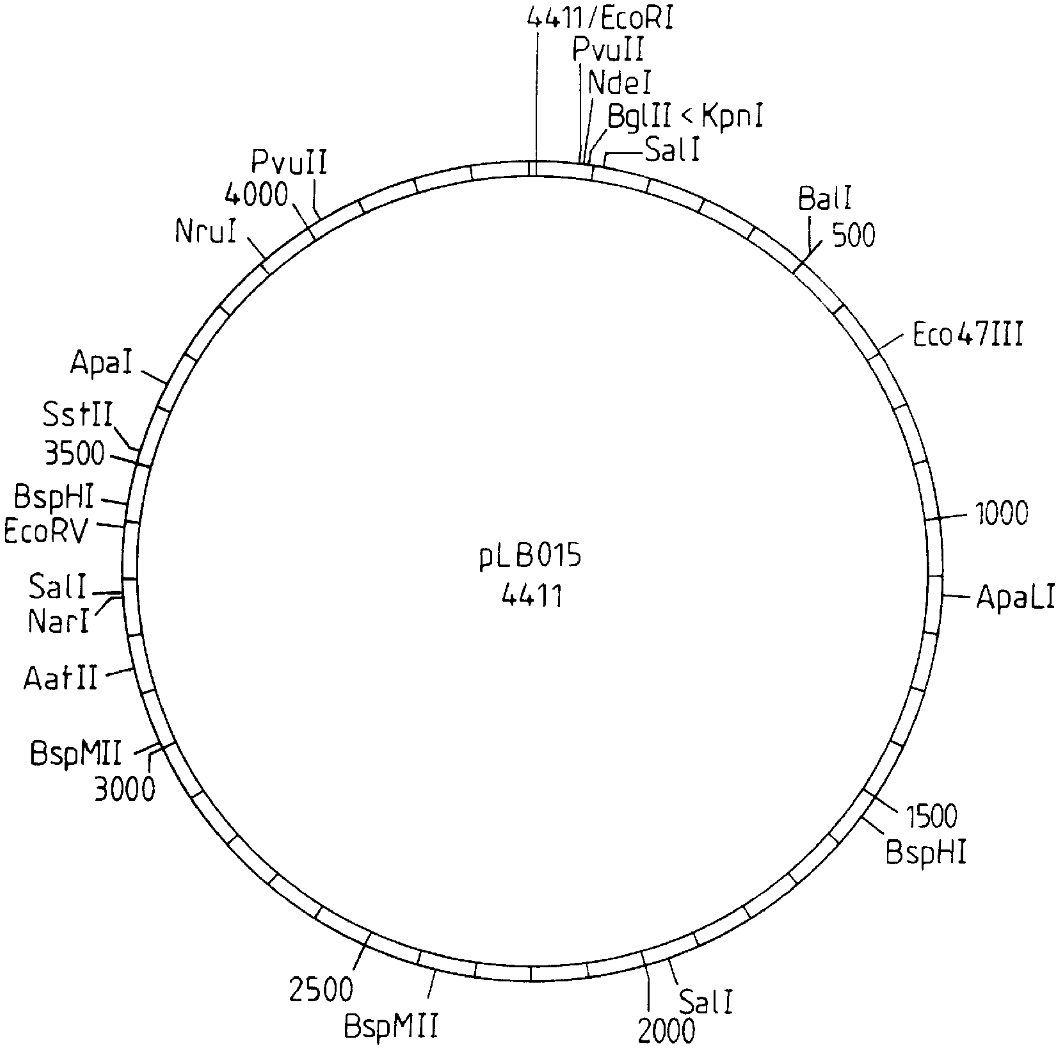
Figure 8:
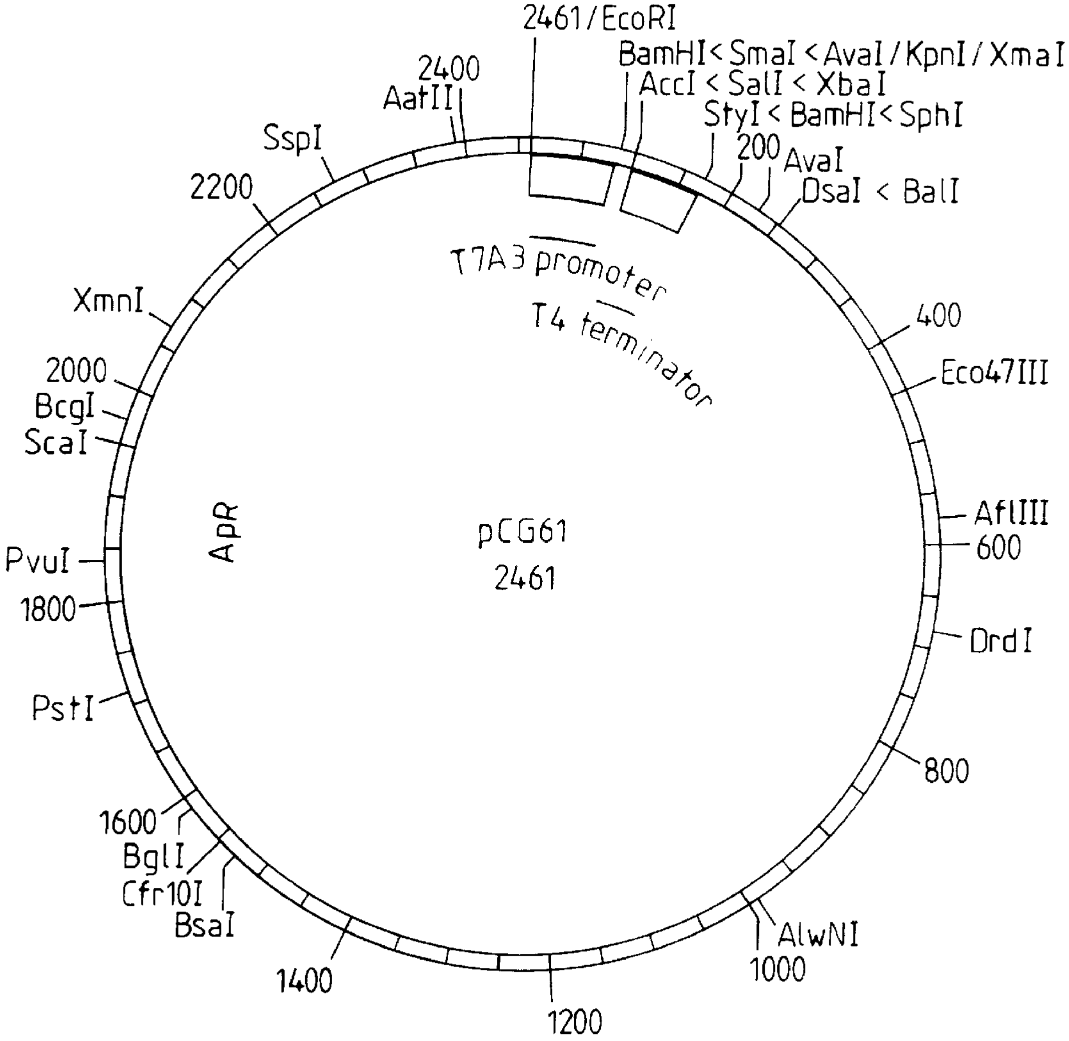
Figure 11:
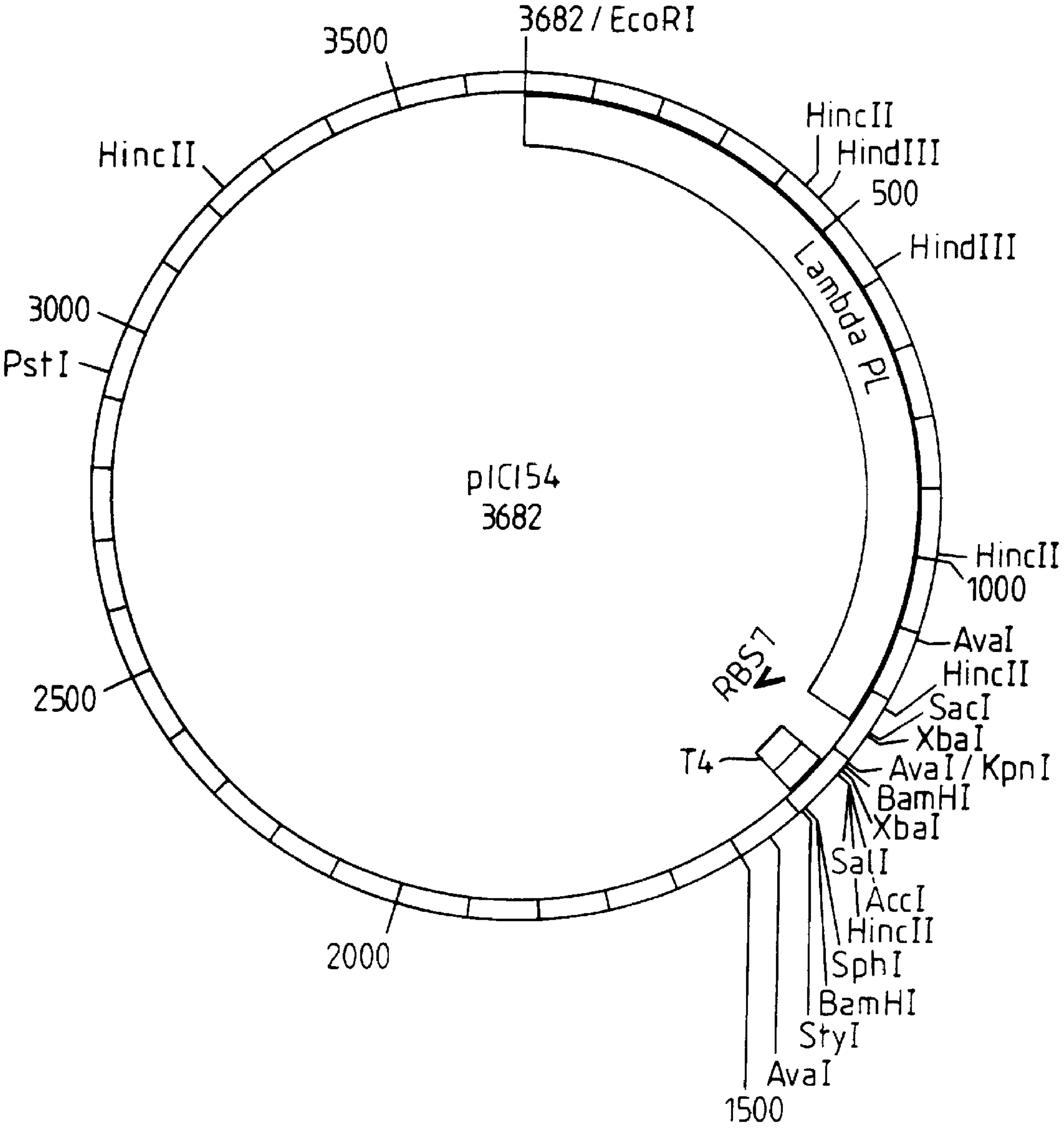
Figure 12A:
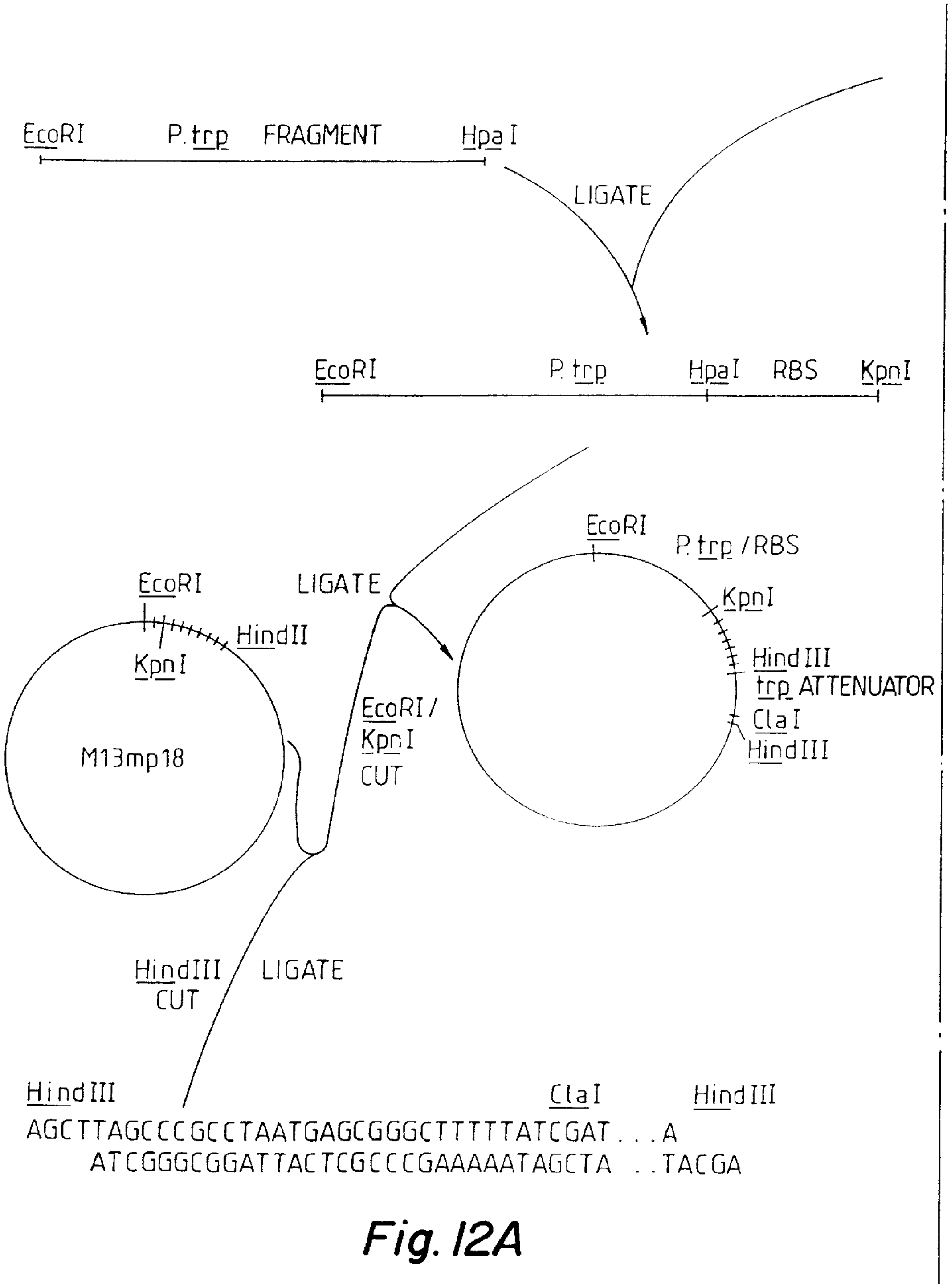
Figure 12B:
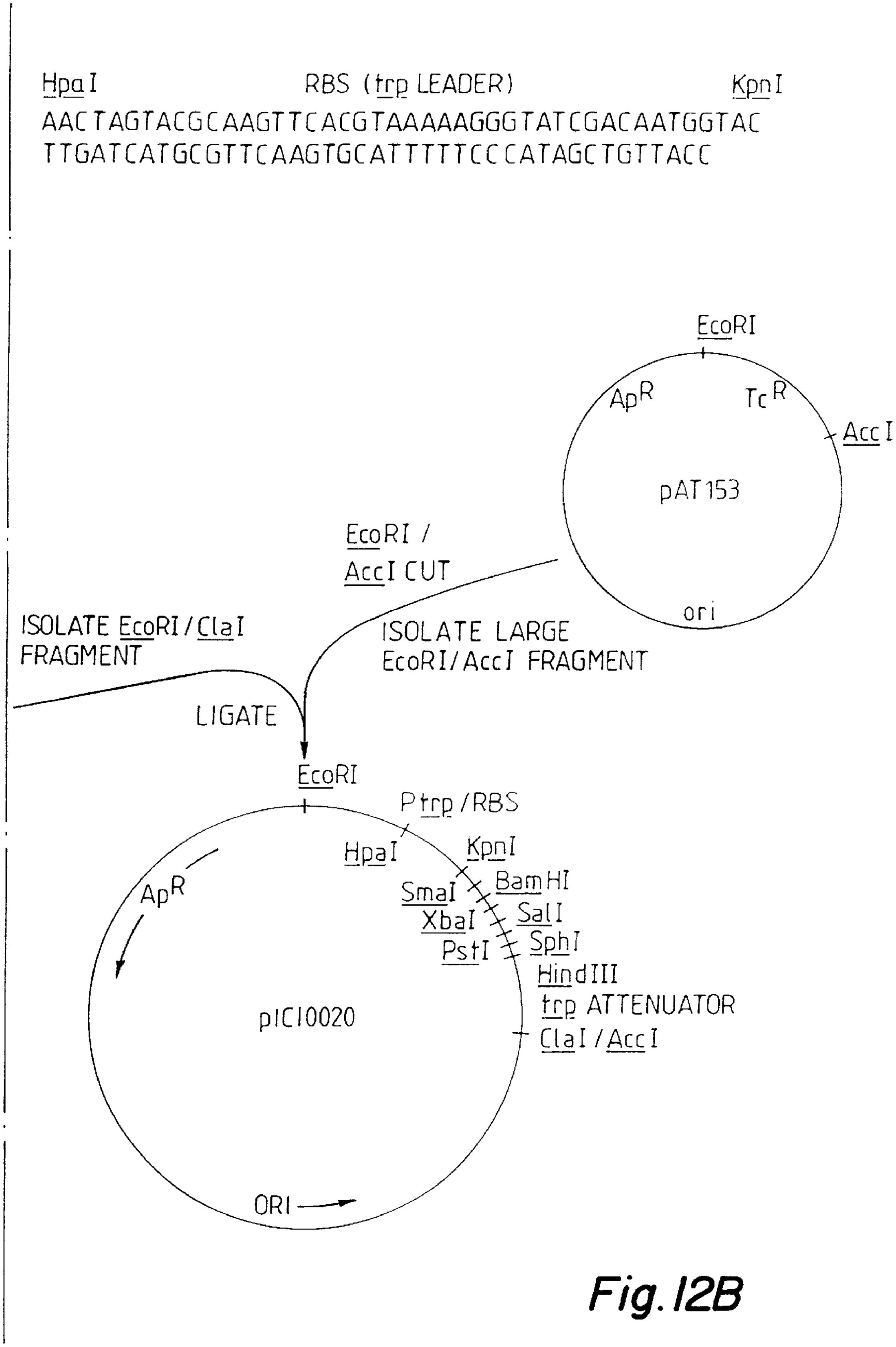
Figure 13:
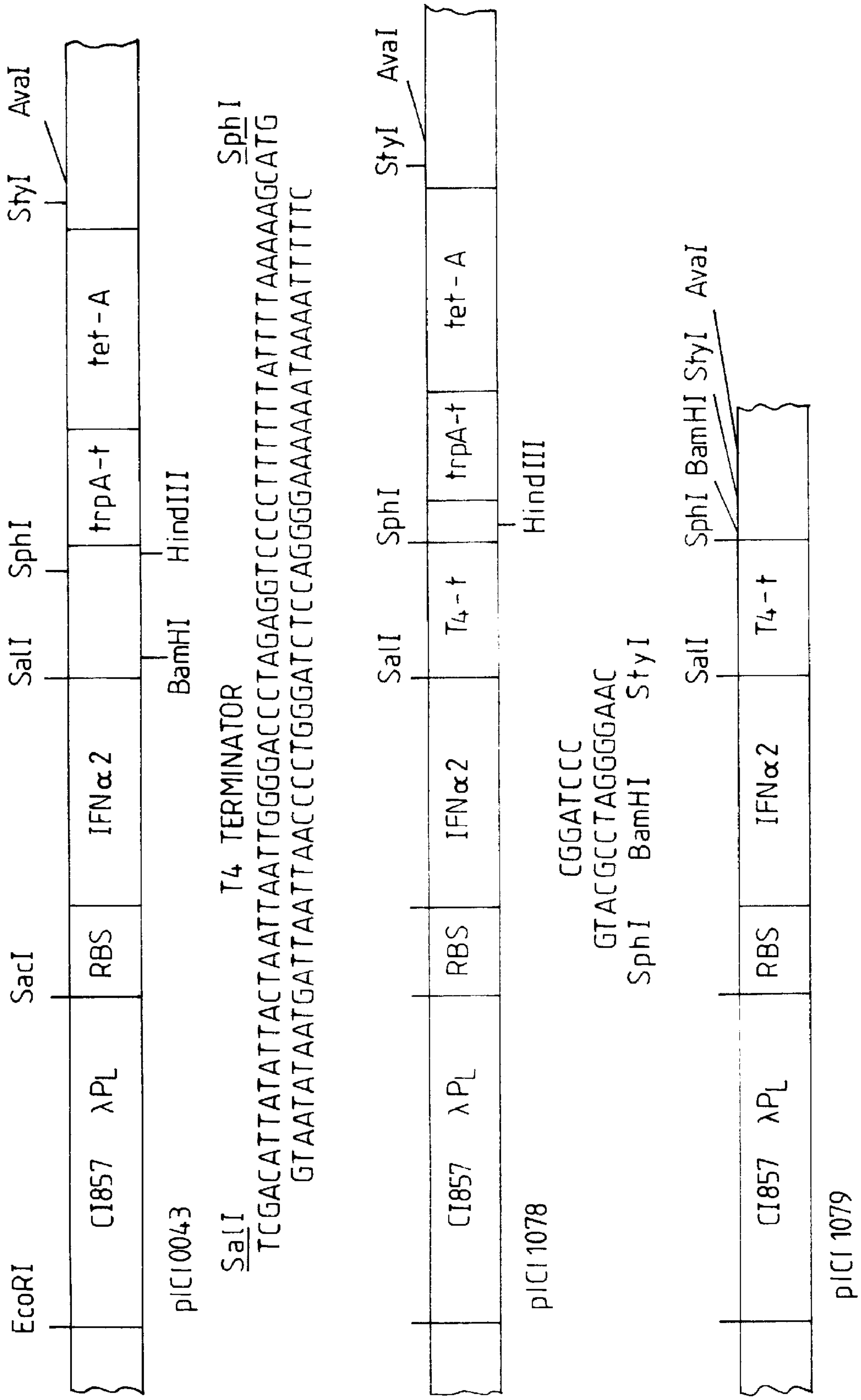
Figure 14A:
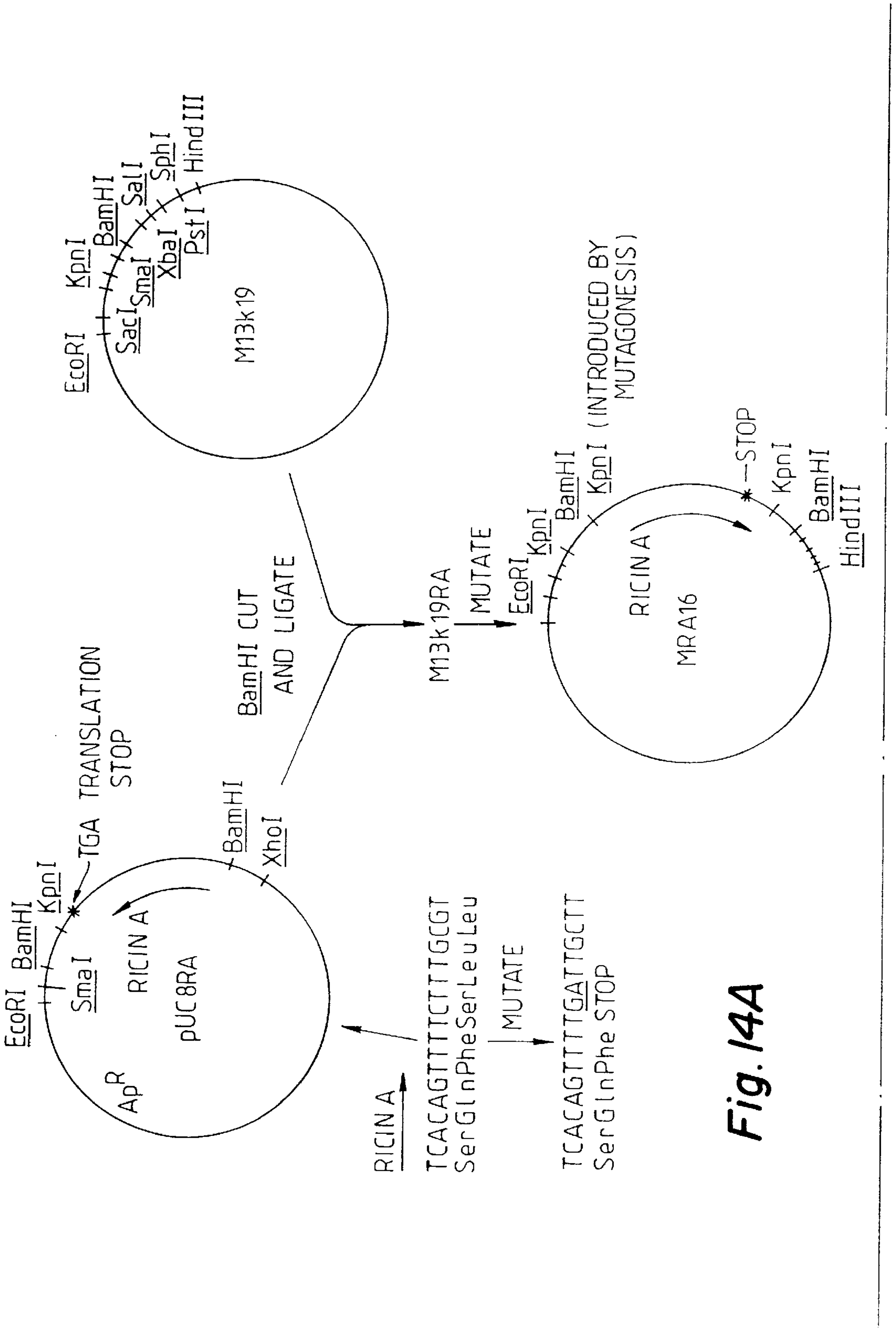
Figure 14B:
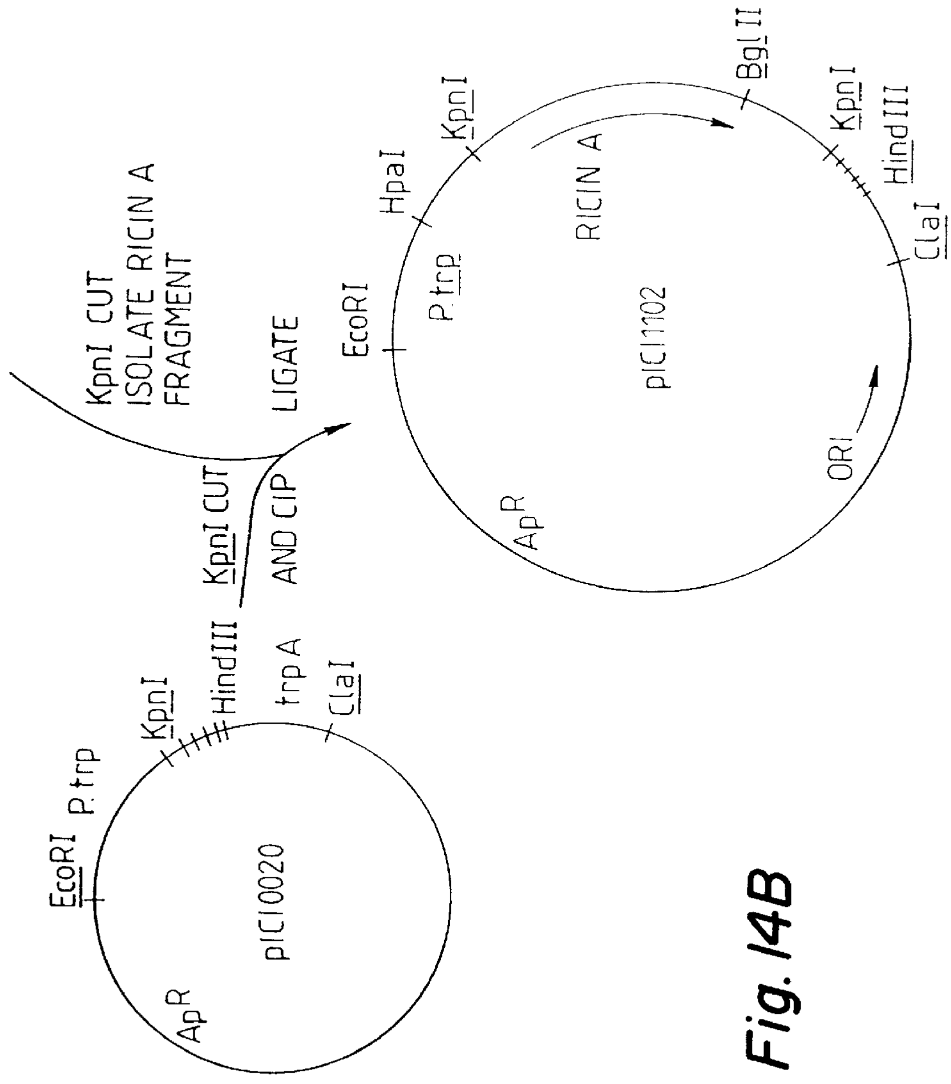
Figure 15:
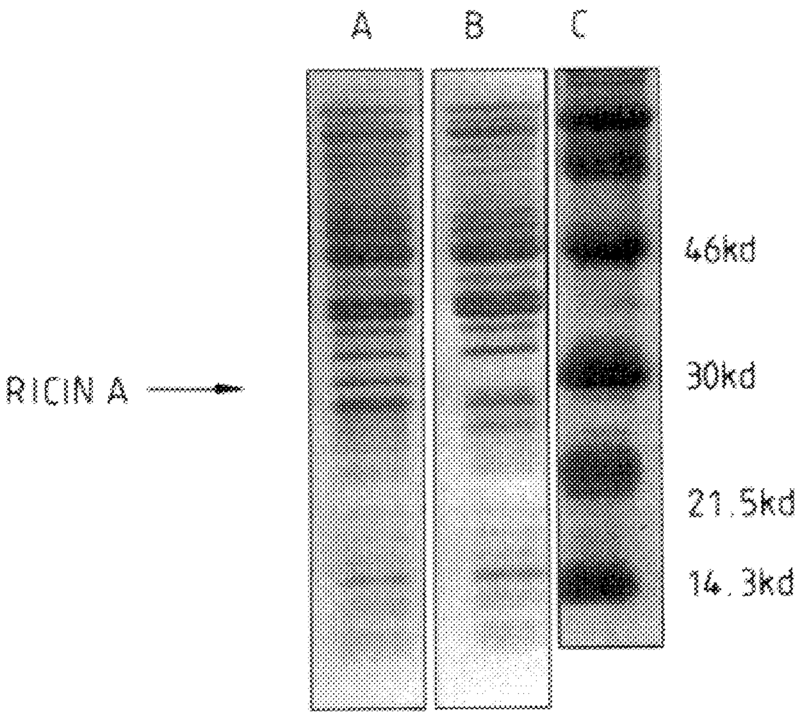

FIGS. 5(*a*) and (*b*) describe fragments used in the preparation of plasmids (SEQ ID NOS: 30, 34, 48);

FIG. 6 is a plasmid map of pICI1079;

FIG. 7 is a plasmid map of pLB015;

FIG. 8 is a plasmid map of pCG61;

FIG. 9 describes the sequence of [$Ser^{17,27}$]G-CSF (SEQ ID NO : 31);

FIGS. 10A and 10B describe the sequence of h-GCSF (SEQ ID NO-: 41);

FIG. 11 is a plasmid map of pCG54;

FIGS. 12A and 12B illustrate the construction of pICI0020 (SEQ ID NOS: 57–59);

FIG. 13 illustrates the construction of pICI1078 (SEQ ID NOS: 33, 49);

FIGS. 14A and 14B illustrate the construction of pICI1102;

FIG. 15 illustrates a coomassie stained SDS gel of *E. coli* lysates in which track A is pICI1102; B is pICI0020, and C is molecular weight markers.

Figure 16:
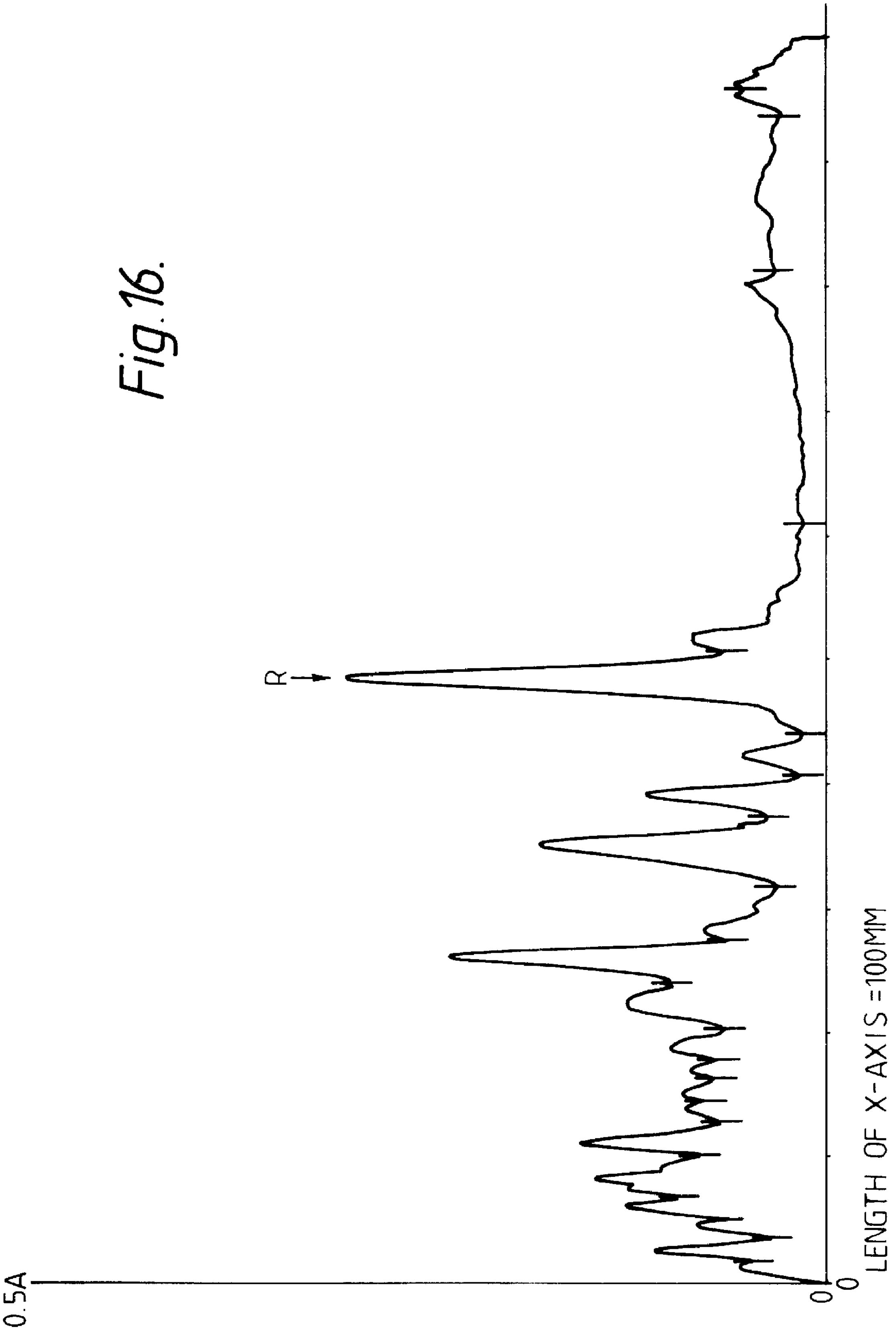
Figure 17:
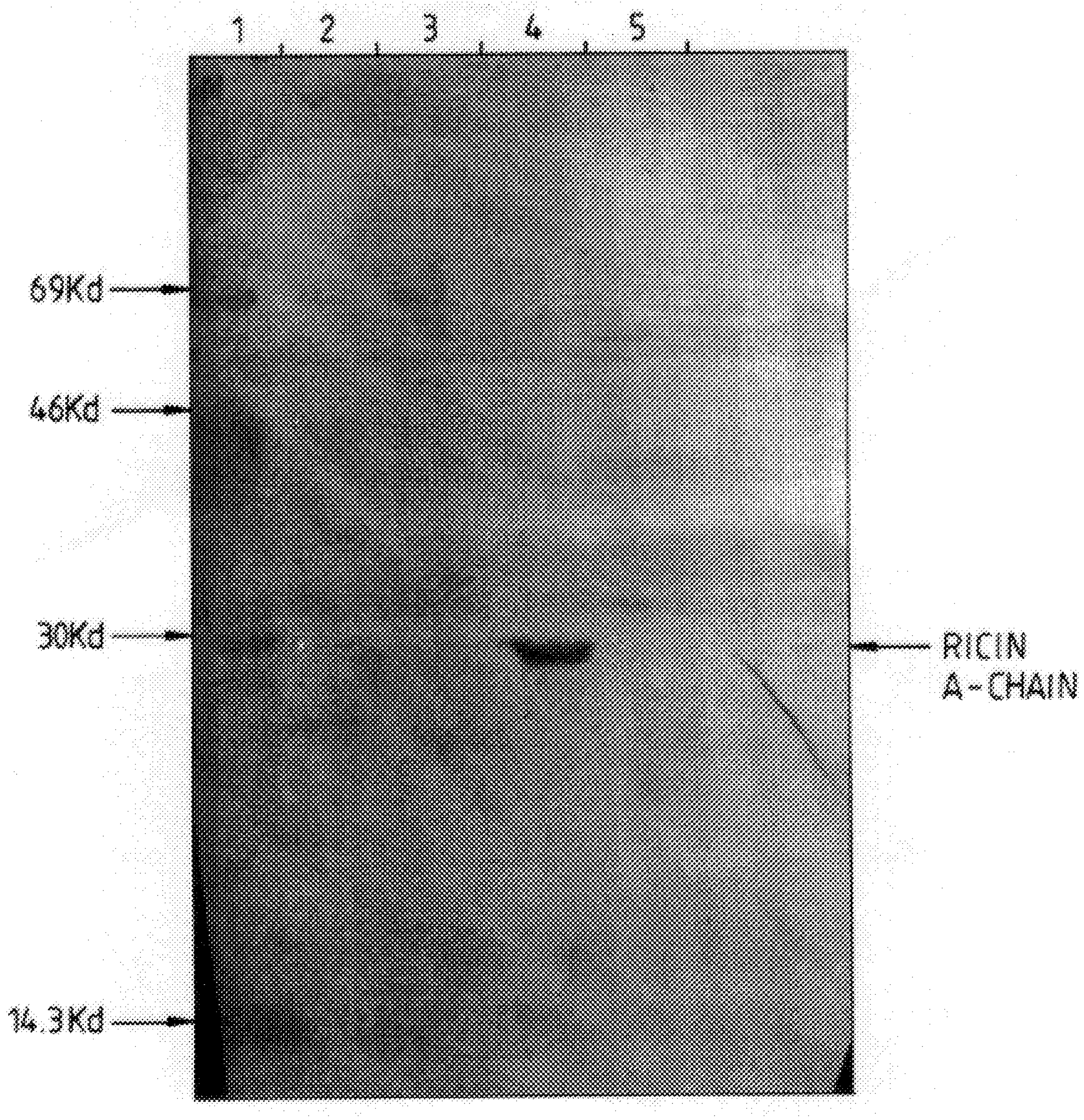
Figure 19:
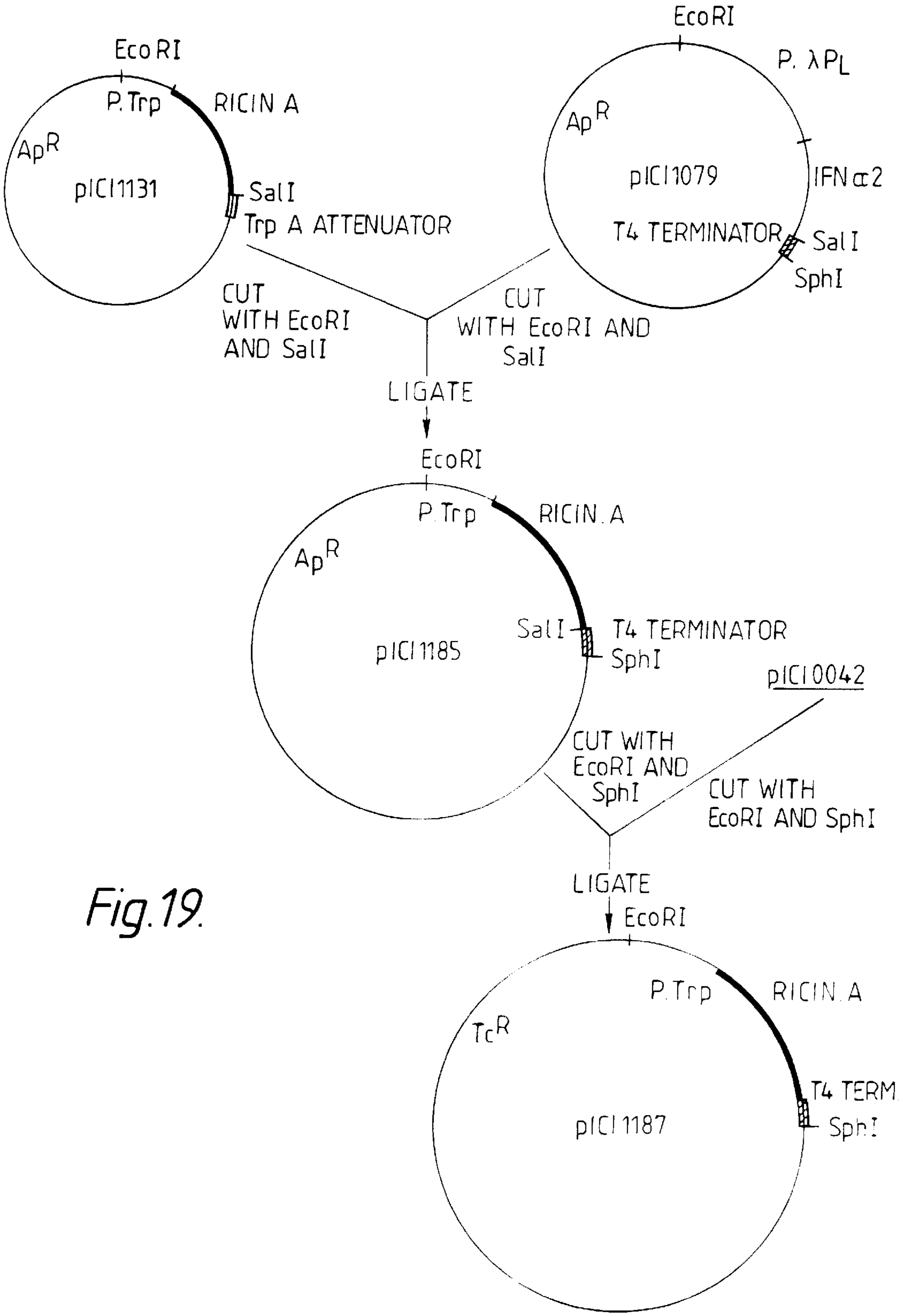

FIG. 16 illustrates a gel profile of pICI1102 in which peak R represents ricin A;

FIG. 17 is a western blot of ricin A produced by pICI1102 and in which track 1 is molecular weight markers; 2 and 3 are non-ricin producing clones; 4 is pICI1102; and 5 is pICI0020 (control plasmid—no ricin A sequence);

FIGS. 18A and 18B are a partial sequence of pICI1102 (SEQ ID NOS: 60, 61); and FIG. 19 illustrates the construction of pICI1187.

The sequences referred to are set out in the "Sequence Listing" following the Examples and sequences are specified in the conventional 5' to 3' sense.

BUFFERS FOR RESTRICTION ENZYMES

Stability: stable at −20° C.

Buffer composition:

| Buffer components | Final concentration in mmol/l (1:10 diluted set buffer) B | M | H |
|---|---|---|---|
| Tris-HCl | 10 | 10 | 50 |
| $MgCl_2$ | 5 | 10 | 10 |
| NaCl | 100 | 50 | 100 |
| Dithioerythritol (DTE) | — | 1 | 1 |
| 2-Mercaptoethanol | 1 | — | — |
| pH at 37° C. | 8.0 | 7.5 | 7.5 |

The above buffers are available from Boehringer Mannheim.

In the site-directed mutagenesis procedure—Example 7

Buffer 1 100 mM Tris HCl pH 8.0

100 mM NaCl 20 mM $MgCl_2$

Buffer 2 10 mM Tris HCl pH 8.0

20 mM NaCl 1 mM EDTA

Buffer 3 12 mM Tris HCl pH 7.7

30 mM NaCl 10 mM $MgCl_2$ 8 mM 2-mercapto ethanol

Buffer 4 60 mM Tris HCl pH 8.0

90 mM NaCl 6 mM $MgCl_2$ 10 mM DTT

Nucleotide mix 1 250 $\mu$M each of dATP, dGTP, dCTP=S (phosphorothioate derivative of dCTP), dTTP and 1 mM ATP Nucleotide mix 2 250 $\mu$M each of dATP, dGTP, dCTP, dTTP and 350 $\mu$M ATP M9 minimal media

| | |
|---|---|
| Ammonium chloride | 1 g |
| Disodium hydrogen orthophosphate | 6 g |
| Potassium dihydrogen orthophosphate | 3 g |
| Sodium chloride | 0.5 g |
| In distilled water | 1 l. |

Supplements/75 ml

| | |
|---|---|
| 300 $\mu$l | 50% glucose |
| 75 $\mu$l | 1 M $MgSO_4$ |
| 75 $\mu$l | 0.1 M $CaCl_2$ |
| 75 $\mu$l | 4 mg/ml thiamine |
| 75 $\mu$l | 20% casein amino acids |

Trace Element Solution (TES)

TES has the following composition:

mg/10 ml deionised water

| | |
|---|---|
| $AlCl_3.6H_2O$ | 2.0 |
| $CoCl_2.6H_2O$ | 0.8 |
| $KCr(SO_4)_2.12H_2O$ | 0.2 |
| $CuCl_2.2H_2O$ | 0.2 |
| $H_3BO_3$ | 0.1 |
| KI | 2.0 |
| $MnSO_4.H_2O$ | 2.0 |
| $NiSO_4.6H_2O$ | 0.09 |
| $Na_2MoO_4.2H_2O$ | 0.4 |
| $ZnSO_4.7H_2O$ | 0.4 |

Geneclean (TM)

The kit contains 1) 6M sodium iodide 2) a concentrated solution of sodium chloride, Tris and EDTA for making a sodium chloride/ethanol/water wash; 3) Glassmilk (TM)—a 1.5 ml vial containing 1.25 ml of a suspension of silica matrix in water.

This is a technique for DNA purification based on the method of Vogelstein and Gillespie published in Proceedings of the National Academy of Sciences USA (1979) Vol 76, p 615.

Alternatively any of the methods described in "Molecular Cloning—a laboratory manual" Second Edition, Sambrook, Fritsch and Maniatis (Cold Spring Harbor Laboratory, 1989) can be used.

Random Label Kit Product of Pharmacia No 27-9250

The procedure is described in "Molecular Cloning—a Laboratory Manual" Second Edition, Sambrook, Fritsch and Maniatis, pp 10.13–10.17 (Published by Cold Spring Harbor Laboratory 1989).

Sequenase (TM)

Chemically modified T7 DNA polymerase

Based on the procedure of Tabor and Richardson published in "Proceedings of the National Academy of Sciences USA" (1987) vol 84 pp 4767–4771.

T4 DNA ligase

Described in "Molecular Cloning—a Laboratory Manual" Second Edition, Sambrook, Fritsch and Maniatis 5.60–5.64 (Published by Cold Spring Harbor Laboratory 1989) and also by Weiss B. et al J. Biol. Chem. Vol 243 p 4543 (1968).

*E.coli* strains

The *E. coli* strains HB101 and CGSC 6300 (also referred to herein as MSD522) are freely available. Thus for example they may be obtained from the *E. coli* Genetic Stock Centre, Yale University, USA. Moreover *E. coli* HB101 may additionally be obtained from for example BRL supplied by GIBCO Limited Unit 4, Cowley Mill Trading Estate, Longbridge Way, Uxbridge, UB8 2YG, Middlesex, England or GIBCO Laboratories, Life Technologies Inc., 3175 Staley Road, Grand Island, N.Y. 14072, USA. The genotype of strain HB101 is described in the aforementioned "Molecular Cloning—A Laboratory Manual" as Sup E44 hsd S20 ($r_B^-$ $m_B^-$)rec A 13 ara-14 $F^-$leu 6 thi-1 proA2 lac Y1 gal K2 rps L20 $xyl^-5$ $mtl^-1$. The genotype of MSD 522 (CGSC 6300) is set out in Example 3.

The following non-limiting Examples are given by way of illustration only.

EXAMPLE 1

Preparation of plasmids containing trp promoter/tetA/tetR genes.

(a) Preparation of pICI0042

Many plasmid vectors are based on one of the original cloning vectors: pBR322 (Bolivar et al, 1977*, Gene* 2: 95–113). The non-mobilizable pAT153 is a derivative of this (Twigg and Sherratt, 1980*, Nature* 283: 216–218). Both these plasmids contain the ampicillin resistance determinant, TEM β-lactamase.

Plasmid pICI0042 utilises a repressed tetracycline resistance determinant, as found on the naturally-occurring plasmid RP4. This repressed system shuts off expression of the tetA gene in the absence of tetracycline whereas most drug resistant mechanisms have constitutive expression.

The tet locus was first mapped on RP4 by Barth and Grinter (*J. Mol. Biol.* 113: 455–474, 1977). This was shown to consist of adjacent genes: tetA, the structural resistance gene and tetR, the repressor gene and this region has been sequenced (Klock et al, *J. Bacteriol*: 161:326–332, 1985). These genes are located on adjacent BglII-SmaI and SmaI-SmaI fragments. The BglII site is unique in RP4 but there are five SmaI sites (Lanka, Lurz and Furste, *Plasmid* 10: 303–307, 1983).

(i) Cloning the tetA+tetR genes

The plasmid RP4 is well documented (Datta et al, *J. Bacteriol* 108: 1244, 1971) and is freely available. Furthermore, the plasmid RP4 has been deposited with the National Collection of Type Cultures, 61 Colindale Avenue, London, NW9 5HT under accession numbers 50078 and 50437. RP4 obtained from N Datta (National Collection of Type Cultures) was used herein. *E. coli* strains containing this plasmid were grown in selective broth cultures and plasmid DNA was isolated by a scale-up of the Holmes and Quigley method (Holmes and Quigley, *Anal. Biochem* 114: 193–197, 1981). It was deproteinized by treatment with 2.5M ammonium acetate and reprecipitated with isopropanol. This plasmid DNA was treated, according to the supplier's recommended conditions, with restriction enzyme BglII and cut to completion. It was then partially cut by XmaI by using diluted enzyme and short incubation times. XmaI is an isoschizomer of SmaI but which produces 4-nucleotide cohesive ends at its cut sites.

The vector plasmid pUC8 (Yanisch-Perron, Vieira and Messing, *Gene* 33: 103–119, 1985) was similarly prepared and cut with BamHI and XmaI to completion. The RP4 fragments were cloned into this vector by ligation with T4 ligase at 12° C. for 16 hours. This was used to transform *E. coli* C600 made competent by the calcium chloride method (Maniatis et al, Cold Spring Harbor Laboratory, 1982). Cultures were then plated onto medium which selected for tetracycline resistance.

*E.coli* C600 is freely available from numerous sources including many culture collections such as the *E.coli* Genetic Stock Centre, Yale University, USA under accession number GCSC 3004. The genotype of *E.coli* C600 is K12 thr-1 leuB6 thi-1 lacY1 tonA21 $\lambda^-$ supE44.

Figure 2:
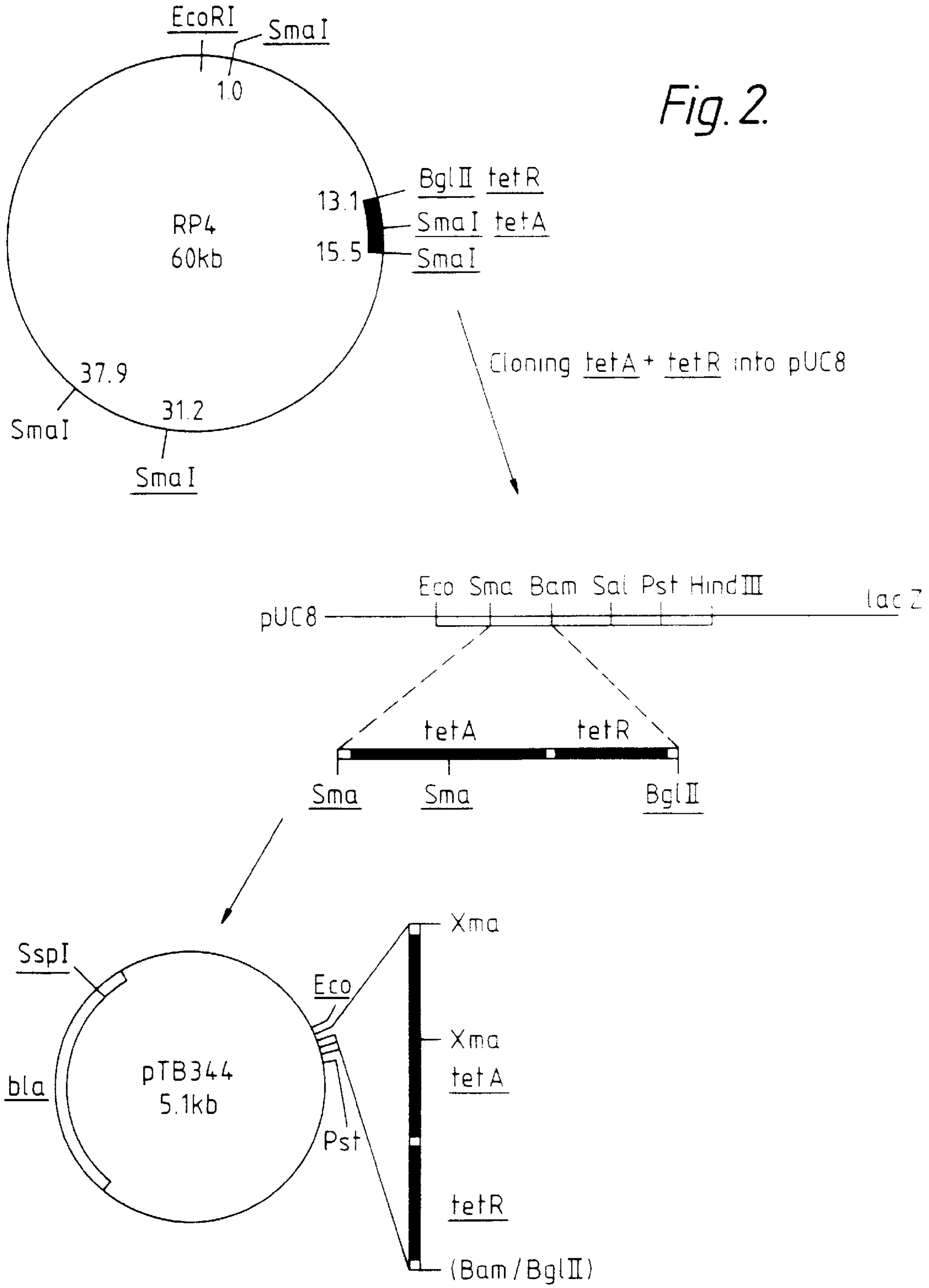
FIG. 2 illustrates the preparation of pTB344.

Several colonies with this resistance were checked for the expected phenotype (ampicillin and tetracycline resistance but not the kanamycin resistance indicative of RP4 itself). Colonies with the correct resistances were subjected to clone analysis by isolating plasmid DNA (Holmes and Quigley method). These preparations were cut with EcoRI and HindIII and analysed by gel electrophoresis. This established the size of the cloned insert which was found to be the 2.45 kb predicted for the BglII-XmaI-XmaI fragment from RP4. A clone carrying this fragment containing the tetA and tetR genes was designated pTB344. (FIG. 2)

(ii) Removal of the tet gene from pAT153

It was necessary to remove the tet gene from the vector plasmid pAT153 before inserting the tetA+tetR cassette from RP4 to prevent gene duplication which can be a source of genetic instability. Also the tet gene may not be effectively suppressed by the non-cognate tetR. The removal was done by isolating plasmid pAT153 DNA and cutting it with EcoRI and AvaI. Between these sites, synthetic oligonucleotides with the following sequence (SEQ ID NO. 40) and SEQ ID NO:53

Figure 3A:
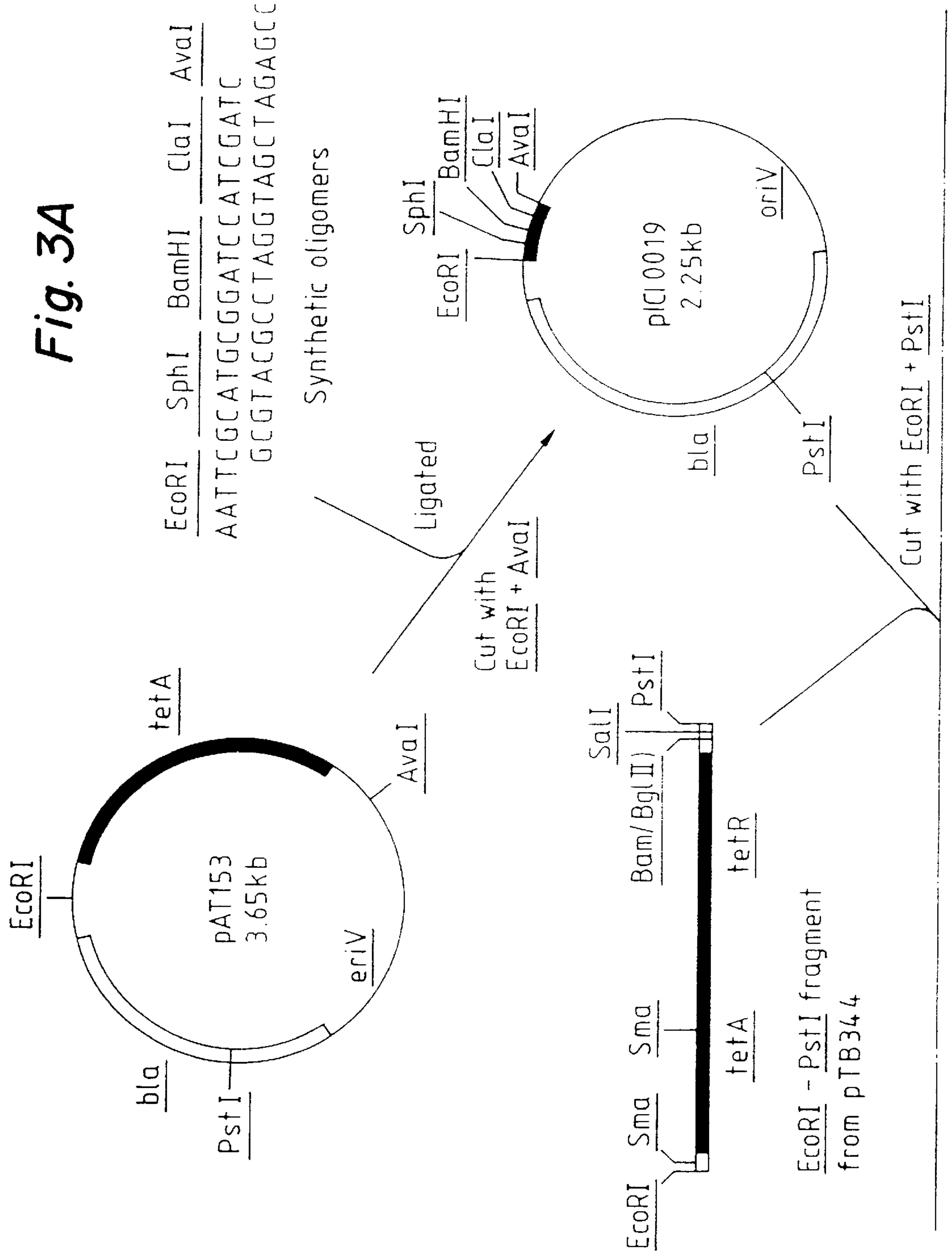
FIG. 3 illustrates the preparation of pICI0042 (SEQ ID NOS: 40, 53)
Figure 3B:
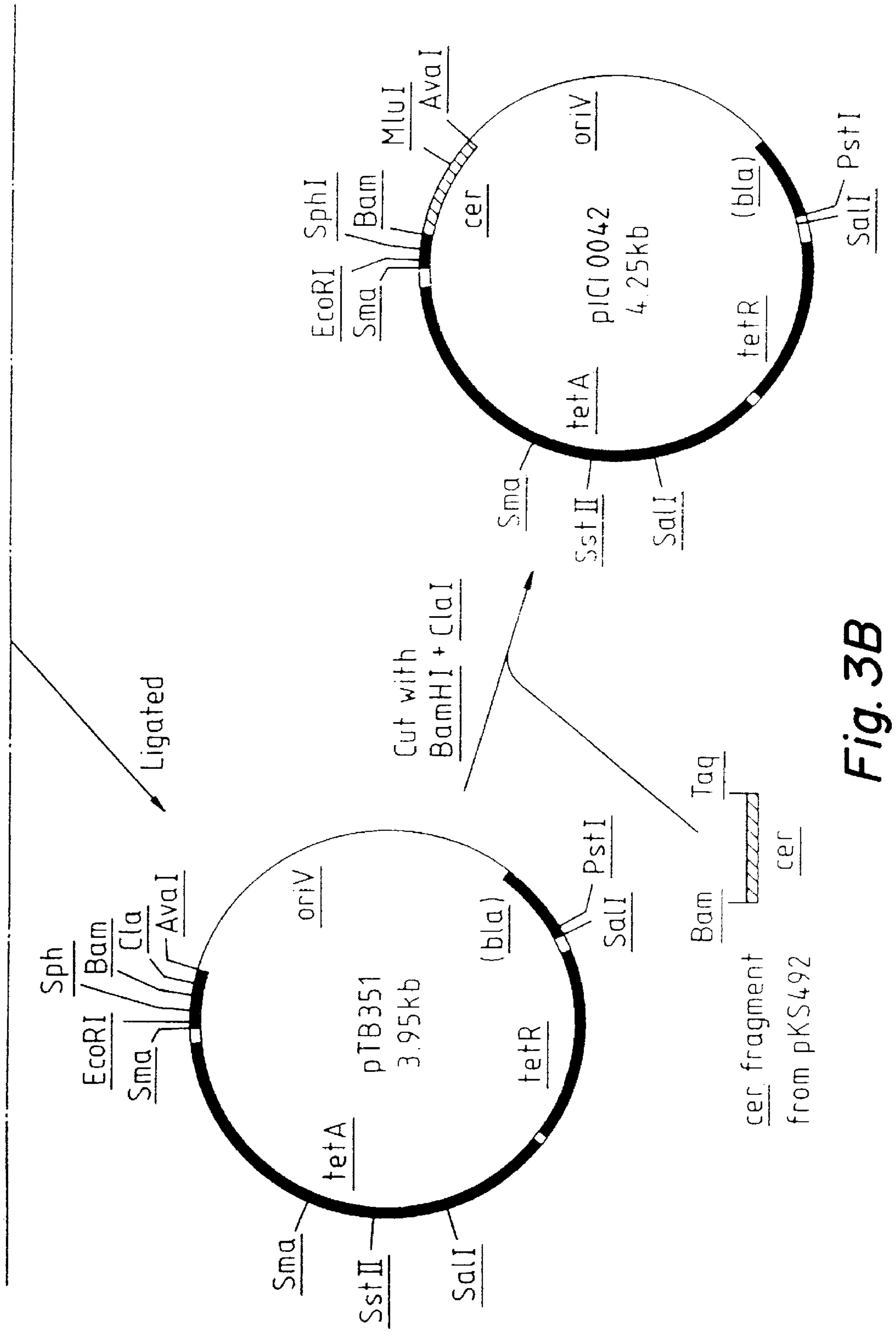

5'AATTCGCATGCGGATCCATCGATC3'
3'GCGTACGCCTAGGTAGCTAGAGCC5' were cloned. These fit the EcoRI and AvaI cohesive ends and contain SphI, BamHI and ClaI sites in addition. After transformation and selection, colonies were tested for the loss of the tetracycline resistance determinant. Plasmid DNA from one clone was sequenced to confirm that the predicted sequence was correct. This plasmid was designated pICI0019. (FIG. 3)

(iii) Insertion of the tetA+tetR genes

The tetA and tetR genes were isolated from pTB344 on an EcoRI to PstI fragment. The pUC8 vector was destroyed by cutting with SspI because it carries the same selection determinant (ampicillin resistance) as pICI0019. Plasmid pICI0019 DNA was cut with EcoRI and PstI and then ligated with the 2.45 kb fragment carrying the tet genes. This was used to transform *E.coli* C600, the culture being plated out under selection for tetracycline resistant colonies. The insertion of the tet genes was designed to replace most of the bla gene in pCH19 which should thus lose its ampicillin resistance determinant. Loss of ampicillin resistance from the transformants was confirmed. A few clones were then used to isolate plasmid DNA which was subjected to restriction analysis. This confirmed that the constructed plasmid had the intended structure. It was designated pTB351. (FIG. 3)

(iv) Insertion of the cer sequence

The naturally-occurring plasmid ColEI is very stably maintained in *E.coli*, whereas its derivatives pBR322 and pAT153 are not. Summers and Sherratt (*Cell*, 36: 1097–1103, 1984) demonstrated that this was due to the derivatives not containing a short (283 bp) sequence called cer which is present in the parent plasmid. This sequence contains a site-specific plasmid multimer-resolution system which prevents the accumulation of plasmid multimers formed by homologous recombination. Such multimers have a deleterious effect on the process of partition which normally ensures stable inheritance of daughter plasmids during bacterial cell division.

Figure 4:
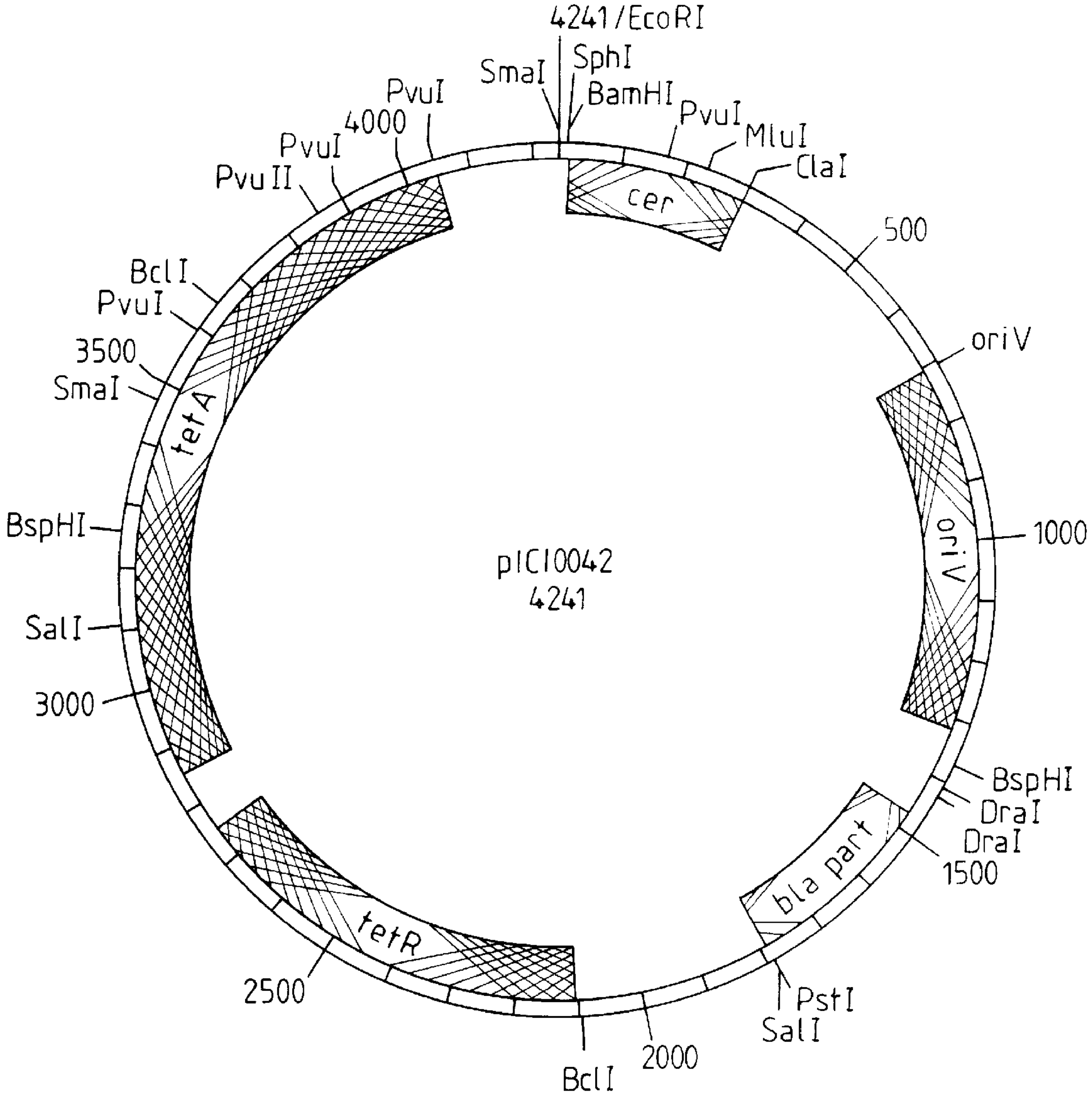
FIG. 4 is a plasmid map of pICI0042.

The cer sequence (Summers, D et al MGG, 201, p334–338, 1985) was isolated from plasmid pKS492 (provided by D. Sherratt) as a 289 bp fragment by cutting with BamHI and TaqI. The plasmid pTB351 was isolated as DNA from a dam strain of *E. coli* to prevent its ClaI site being blocked by the dam$^+$ methylation system. This DNA was cut with BamHI and ClaI (both these sites having been introduced on the synthetic oligonucleotide for this cloning). The cer fragment was ligated with the cut vector and then used to transform *E. coli* C600, selection being made for tetracycline resistance. Transformant colonies were subjected to clone analysis by AvaI restriction and gel electrophoresis. The presence of an extra DNA band of about 300 bp indicated the acquisition of the cer fragment. Further restriction analyses were used to confirm that resultant plasmids had the correct structure. One of these was designated pICI0042 (FIG. 3 and 4).

(v) Tests on pICI0042

The plasmid has been completely sequenced using the DuPont Genesis 2000 machine. (FIG. 3 and 4).

The inducibility of the tetracycline resistance was checked. First the minimal inhibitory concentration (MIC) of tetracycline for (pICI0042)C600 was measured. This was done by inducing a culture of this strain with 0.5 μg/ml of tetracycline. After growth, this culture was serially diluted and plated onto broth media containing levels of tetracycline from 0 to 500 μg/ml to give about 100 colonies per plate. The MIC was found to be about 200 μg/ml. A culture of (pICI0042)C600 was then grown to early log phase in Luria broth in the absence of tetracycline. This was used to inoculate parallel cultures in broth, with and without tetracycline induction. These were grown with aeration at 37° C. for 90 minutes to allow induced expression. Serial dilutions of these cultures were then plated onto rich medium with and without 100 μg/ml of tetracycline. The resulting colonies demonstrated that the viability of the uninduced culture was 1600-fold lower than the induced culture on the tetracycline medium. This confirms that the tetA+tetR induction system in pICI0042 is working satisfactorily.

The maintenance stability of pTB351 and pICI0042 in *E. coli* C600 were checked. This was in order to compare them with their parent plasmid pAT153 and note the effect of the cer sequence in pICI0042. Cultures were grown without selection and samples checked for the presence of the plasmid after 50, 100 and 150 generations of growth. We found no plasmid loss by either strain throughout this period. Thus pTB351, even without a cer sequence, appears to have gained stability over its parent pAT153. This may be a consequence of the deletion of its tet gene. Naturally-occurring plasmids always have tetracycline resistance under inducible control so the constitutive tet gene in pAT153 may be counterselective in the absence of tetracycline. This could be due to the fact that the tetracycline resistance mechanism acts as a cytoplasmic membrane export pump. When not required it may harm the cell by damaging the membrane structure, exporting wanted metabolites or wasting metabolic energy. The presence of the cer sequence in pICI0042 should contribute to plasmid maintenance stability even under the counterselective conditions of using it to express a recombinant gene at high level.

(b) Preparation of Plasmid pCH101

The plasmid pCH101 corresponds to pICI 0020 (see Example 5c) except that the EcoRI-SalI fragment (see FIG. 5*a*) is replaced by a fragment consisting of the SEQ ID No 34 (see FIG. 5*b* also) and the interferon $\alpha_2$ gene sequence as described by Edge M.D. et al, Nucleic Acids Research 1983, Vol 11, p6419–6435. In this regard the 3'-terminal ATG codon of SEQ ID No 34 immediately precedes the TGT codon which codes for cysteine (amino acid 1) in the interferon $\alpha_2$ sequence of the above-mentioned Edge M.D. et al Nucleic Acids Research reference. The 5' nucleotide sequence GATCCATG and the complementary 3' nucleotide sequence GTAC are thus omitted from the nucleotide sequence of the aforementioned reference.

(c) Insertion of an Expression Cassette into pICI0042

An expression cassette consisting of the trp promoter, a ribosome binding site and the interferon $\alpha_2$ gene was isolated from plasmid pCH101 (see b above) on an EcoRI to SphI restriction fragment. This was ligated into the production vector (pICI0042) (see above) similarly cut with EcoRI and SphI. This DNA was used to transform a competent culture of *E. coli* C600 and tetracycline resistant colonies were isolated. A few of these were tested by DNA clone analysis for the acquisition of the SstI restriction site carried on the expression cassette. Clones positive in this respect were further tested by restriction mapping to check that the expected construct was correct. They were also checked for the conferred capacity to produce interferon $\alpha_2$ protein as analysed on a polyacrylamide-SDS gel stained with Coomassie blue. One such confirmed clone was designated pLB005.

(d) Insertion of T4 transcription terminator into pTB244

The T4 transcription terminator sequence in the form of the SalI to HindIII fragment (67 bases pairs long) (FIG. 1*b* and SEQ ID NO:33 hybridized to SEQ ID NO:49 as indicated in FIG. 1*b*) was inserted into the multicloning site of an intermediate vector pTB244 (described in European Patent Publication No. 237,269) between its SalI and HindIII sites. Clone analysis was used to confirm the structure of this construct (pTB244-T4 ter). From this vector, an SstI to SphI fragment containing most of the multicloning site and the T4 terminator was then isolated. This was inserted into pLB005 similarly cut with SstI and SphI thereby substituting the interferon $\alpha_2$ gene but leaving a cassette consisting of the trp promoter, multicloning site and T4 terminator. This construct was confirmed by clone analysis and the plasmid designated pLB013.

(e) Substitution of the multicloning site

The multicloning site in pLB013 is not ideal for this vector in several respects: the SalI, BamHI and SmaI sites are not unique but exist elsewhere on the plasmid. This fragment was therefore excised by cutting with SstI and XbaI (both unique) and synthetic oligonucleotides with the following sequence (SEQ ID NO:35 and SEQ ID NO:50)

```
5' AGCTCCATATGGTACCAGATCTCTCGAGAGTACTT
          GGTATACCATGGTCTAGAGAGCTCTCATGAAGATC 5'
```

were inserted in its place. Clones were analysed for acquisition of the new restriction sites and then confirmed by sequencing. One such plasmid was designated pLB014. The new cloning sites inserted in this way are: NdeI, KpnI, BglII, XhoI and ScaI with the previous XbaI and SalI following them.

(f) Further modification

It was discovered that the adjacent SstI and NdeI sites in pLB014 could not be cut by both these restriction enzymes either simultaneously or sequentially presumably because of their close proximity. An additional sequence was therefore inserted between them. This was done by cutting pLB014 with SstI and KpnI and then inserting the following synthetic oligonucleotide (SEQ ID NO:36 and SEQ ID NO:51)

```
5' AGCTCAGCTGCAGCATATGGTAC
          GTCGACGTCGTATAC 5'
```

Clones were analysed for acquisition of an extra PvuII or PstI site and then confirmed by sequencing. One such plasmid was designated pLB015 (=pICI0080) (see FIG. 7). This plasmid, unlike pLB014, is efficiently cut by SstI and NdeI. This is to provide a place to insert a variety of ribosome binding site sequences correctly positioned with respect to the upstream trp promoter and with NdeI designed to provide the ATG start codon of the gene to be expressed.

EXAMPLE 2

Preparation of [$Arg^{11}$,$Ser^{17,27,60,65}$]human G-CSF using vector including trp promoter a) Plasmid pICI1239 (described in Example 7) was digested with EcoRI and SalI in buffer H as described previously. The small EcoRI-SalI fragment containing the trp promoter, ribosome binding site and gene for [$Arg^{11}$,$Ser^{17,27,60,65}$]hu G-CSF was isolated from a 0.7% agarose gel by use of Geneclean(TM). A vector fragment was prepared from pICI 0080 (see Example 1f) by digestion with EcoRI and XhoI in buffer H and the large EcoRI-XhoI fragment isolated from a 0.7% agarose gel by use of Geneclean(TM). The small EcoRI-SalI fragment was ligated into the EcoRI-XhoI vector fragment, using a 2:1 molar excess of insert to vector as described previously and the ligation mix used to transform *E. coli* strain MSD 522. Transformants were selected for growth on L-agar plates containing tetracycline (15 μg/ml). Three colonies were selected and grown up in M9 minimal media (75 ml) containing supplements and tetracycline (15 μg/ml) at 37° C. for 20 hours on a reciprocating shaker. Protein accumulation was measured by scanning Coomassie blue stained SDS-PAGE gels of whole cell lysate. All three clones expressed [$Arg^{11}$,$Ser^{17,27,60,65}$]hu G-CSF. Plasmid DNA from one of the colonies was designated pICI1327 and the sequence of the promoter and gene confirmed by standard dideoxy sequencing procedures as described previously.

b) Fermentation pICI 1327 was transformed into *E. coli* strain MSD 522 and the resultant recombinants purified and maintained on glycerol stocks at −80° C.

An aliquot of the culture was removed from stock and streaked onto agar plates of tetracycline to separate single colonies after overnight growth at 37° C. A single desired colony was removed and resuspended in 10 ml tetracycline broth and 100 μl immediately inoculated into each of 3 250 ml Erlenmeyer flasks containing 75 ml tetracycline broth. After growth for 16 h at 37° C. on a reciprocating shaker the contents of the flasks were pooled and used to inoculate a fermenter containing 20 L growth medium.

Composition of Growth Medium

| | Made up of distilled water g/l |
|---|---|
| $KH_2PO_4$ | 3.0 |
| $Na_2HPO_4$ | 6.0 |
| NaCl | 0.5 |
| Casein hydrolysate (Oxoid L41) | 2.0 |
| $(NH_4)_2SO_4$ | 10.00 |
| Yeast Extract (Difco) | 10.00 |
| Glycerol | 35.00 |
| L-Leucine | 0.625 |
| $MgSO_4.7H_2O$ | 0.5 |
| $CaCl_2.2H_2O$ | 0.03 |
| Thiamine | 0.008 |
| $FeSO_4$/Citric Acid | 0.04/0.02 |
| Trace element solution (TES) | 0.5 ml $l^{-1}$ |
| Tetracycline | 10 mg $l^{-1}$ |

Fermentations were then carried out at a temperature of 37° C., and at a pH, controlled by automatic addition of 6M sodium hydroxide solution, of pH 6.7. The dissolved oxygen tension (dOT) set point was 50% air-saturation and was initially controlled by automatic adjustment of the fermenter stirrer speed. Air flow to the fermenter, initially 20 L/min, corresponding to 1 volume per volume per minute (VVM) was increased to 50 L/min (2.5 VVM) when the fermenter stirrer speed approached 80–90% of its maximum. Since the oxygen transfer rate (OTR) of the fermenters was unable to meet the oxygen uptake rate (OUR) of the bacteria at a cell density greater than that corresponding to an $OD_{550}$ of 50 under the conditions described, dOT in the fermenter at cell densities greater than this was maintained at 50% air-saturation by restricting bacteria oxygen uptake rate. This was achieved by formulating the medium to become carbon-limited at $OD_{550}$ of 50 and then supplying a feed of the limiting carbon source, together with ammonium sulphate and yeast extract, at a rate which restricted bacterial growth rate.

Fermentations were performed for 18 h and during that time samples were taken for measurement of optical density ($OD_{550}$), cell dry weight and accumulation of [$Arg^{11}$,$Ser^{17,27,60,65}$]human G-CSF within the cells. [$Arg^{11}$,$Ser^{17,27,60,65}$] human G-CSF accumulation was measured by scanning Coomassie blue stained SDS-PAGE gels of whole cell lysates of the sampled bacteria as is well known in the art.

When $OD_{550}$ reached 35 (8.5 h), casein hydrolysate solution (100 g/l Oxzoid L41) was pumped into the fermenters at a rate of 0.75 g/l/h.

When $OD_{550}$ reached approximately 50, the supply of carbon-source in the fermentation batch became exhausted leading to a rapid rise in dOT from 50% air saturation. At this point, a feed containing glycerol (470 g/l), yeast extract (118 g/l) and ammonium sulphate (118 g/l) was pumped into the fermenters at a rate which returned and then maintained the dOT at 50% air saturation with the fermenter stirrer at ca 70–80% of its maximum. Casein hydrolysate feeding was maintained at 0.75 g/l/h throughout. After approximately 18 hours, when microscopic examination of the culture showed the presence of large inclusion bodies within a majority of the cells, bacteria were harvested on a Sorval RC3B centrifuge (7000 g, 30 min., 4° C.) and stored frozen at minus 80° C.

EXAMPLE 3

Preparation of [$Arg^{11}$,$Ser^{17,27,60,65}$]human G-CSF using vector including T7A3 promoter a) An EcoRI-SalI fragment, containing a T7A3 promoter, a trp leader ribosome binding site sequence and a gene for [$Ser^{17,27}$]hu G-CSF was sub-cloned into M13 mp18 as described in part d) of Example 5. The sequence of the EcoRI-SalI fragment is set out in SEQ ID No 32 and FIG. 9, SEQ ID No 32 consists of the EcoRI restriction site (nucleotides 1–6), the A3 promoter sequence of bacteriophage T7 (nucleotide 7–52), the trp leader ribosome binding site sequence (nucleotides 53–78)and translation initiation codon (nucleotides 79–81). FIG. 9 sets out the nucleotide sequence of [$Ser^{17,27}$]human G-CSF terminating in the SalI restriction site. It will be appreciated that the 3' terminal ATG codon of SEQ ID No 32 immediately precedes the ACT codon which codes for threonine (amino acid 1) in FIG. 9. The 5' nucleotide sequence AATTCAGT is thus absent from the EcoRI-SalI fragment. The EcoRI-SalI fragment may also be prepared by excision from pICI 1295 (see Example 8). Site-directed mutagenesis was performed on single-stranded DNA as described in the protocol described in Example 7 using oligonucleotide SEQ ID No 28 to convert the codon for Gln at position 11 to Arg. Double-stranded RF DNA was prepared from a plaque containing the $Gln^{11}$→$Arg^{11}$ change as described in Example 6, except that at step B3 incubation was for 3 hours instead of 5 hours, and digested with EcoRI (as described previously) and SnaBI (10 units, 1×M buffer, BCL, 30 μl, 2 hours, 37° C.). The resulting 144 bp EcoRI-SnaBI fragment containing the T7A3 promoter, trp leader ribosome binding site sequence and gene fragment with $Arg^{11}$ codon was isolated and ligated to an EcoRI-SnaBI cut vector from pICI 1327 (which contains codons for $Ser^{60}$ and $Ser^{65}$ and is described in Example 2). The ligation mix was used to transform *E. coli* strain MSD522 and transformants selected for growth on L-agar plates containing tetracycline (15 μg/mg). Plasmid DNA from a colony containing the expected T7A3 promoter and [$Arg^{11}$,$Ser^{17,27,60,65}$] hu G-CSF gene sequence were identified by sequencing DNA from the isolated plasmid and designated pICI 1386.

The fermentation was effected according to two alternative processes (b) and (c) below. Process (b) was effected at 37° C. and after 16 hours fermentation as described, microbial biomass was 35 g/l and [$Arg^{11}$,$Ser^{17,27,60,65}$]human G-CSF was estimated to be accumulated to 7 g/l fermentation broth. Process (c) was effected at 30° C. and the fermentation was accordingly slower because of the lower fermentation temperature. With regard to process(c), after 35 hours, the microbial biomass was 55 g/l and the [$Arg^{11}$, $Ser^{17,27,60,65}$]human G-CSF yield was estimated to be accumulated to 15 g/l fermentation broth.

b) *E.Coli* strain CGSC 6300 (genotype $F^-$, $\lambda^-$, lac+) obtained from the *E.coli* Genetic Stock Centre was transformed with plasmid pICI 1386. The resultant strain CGSC 6300 (pICI 1386) was purified and maintained in glycerol stocks at −80° C. An aliquot of the culture was removed from stock and streaked onto agar plates of L-tetracycline to separate single colonies after overnight growth (16 h) at 37° C. A single colony of CGSC 6300 (pICI 1386) was removed and resuspended in 10 ml L-tetracycline broth and 100 μl immediately inoculated into each of twenty 250 ml Erlenmeyer flasks containing 75 ml of L-tetracycline broth. After growth for 16 h at 37° C. on a reciprocating shaker the contents of the flasks were pooled, and used to inoculate a fermenter containing 20 litres of modified LCM50 growth medium. The composition of the growth medium is in Table 1.

TABLE 1

Composition of growth medium

| Modified LCM50 Growth Medium (A) | made up with distilled water g/l |
|---|---|
| $KH_2PO_4$ | 3.0 |
| $Na_2HPO_4$ | 6.0 |
| NaCl | 0.5 |
| Casein Hydrolysate (Oxoid L41) | 2.0 |
| $(NH_4)_2SO_4$ | 10.0 |
| Yeast extract (Difco) | 20.0 |
| Glycerol | 35.0 |
| $MgSO_4.7H_2O$ | 0.5 |
| $CaCl_2.2H_2O$ | 0.03 |
| Thiamine | 0.008 |
| $FeSO_4$/Citric acid | 0.04/0.02 |
| Trace element solution (TES) | (0.5 ml $l^{-1)}$ |
| Tetracycline | (10 mg $l^{-1}$) |

The fermentation was then carried out at a temperature of 37° C. and at a pH, controlled by automatic addition of 6M sodium hydroxide solution, of pH 6.7. The dissolved oxygen tension (dOT) set point was 50% air saturation and was initially controlled by automatic adjustment of the fermenter stirrer speed. Air flow to the fermenter was initially 20 L/min corresponding to 1.0 volume volume per minute (VVM) and was increased to 45 L/min manually when the fermenter stirrer speed reached its maximum (1000 rpm). The fermentation was performed for 16 h and during that time samples were taken for measurement of optical density of the culture ($OD_{550}$ biomass concentration, total microbial protein concentration and accumulation of [$Arg^{11}$,$Ser^{17,27,60,65}$]human G-CSF within the bacterial cells. Accummulation was measured by scanning Coomassie blue stained SDS-PAGE gels of whole cell lysates of the sampled bacteria as is well known in the art. Total microbial protein was estimated by the method of Lowry. A solution of yeast extract (225 g/L) was pumped into the fermenter 4.5 h post inoculation at 1.7 g/L/h. When the supply of carbon source (glycerol) in the growth medium became exhausted dOT increased rapidly from 50% air saturation. At this point a feed containing glycerol (714 g/l) and ammonium sulphate (143 g/L) was pumped. Since the bacterial oxygen sulphate rate (OUR) approached the maximum oxygen transfer rate of the fermenter (OTR) just prior to the carbon source in the batch growth medium becoming exhausted, the feed was pumped into the fermenter at a rate which restricted the bacterial OUR to approximately 80–90% of the fermenters maximum OTR. The feed rate was adjusted manually to return and then maintain dOT at 50% air saturation under the conditions described.

c) The fermentation process described in (b) was repeated but at a temperature of 30° C. for 35 hours. Except for the fermentation temperature of 30° C. the medium and fermentation conditions were identical to those described in (b).

EXAMPLE 4

Preparation of plasmid pAG88 a) Preparation of a synthetic gene for human G-CSF

A DNA sequence (FIG. 10) designated SEQ ID No:55 and encoding the amino-acid sequence of the polypeptide of FIG. 10 (human G-CSF) designated SEQ ID No:56 was designed according to the following considerations:

1) Single—stranded cohesive termini to allow ligation at suitable sites in a plasmid.
2) A series of restriction endonuclease sequences throughout the gene to facilitate subsequent genetic manipulation.
3) Translation termination codon.
4) Codons at the 5'-end of the coding region were normally chosen to be A/T rich. Other codons were normally chosen as those preferred for expression in *E.coli.*

The gene was assembled from the 18 oligonucleotides designated SEQ ID No.1–SEQ ID No. 18 and shown hereinafter.

Preparation of Oligonucleotides

The oligonucleotide sequences shown hereinafter were prepared on an Applied Biosystems 380A DNA synthesiser from 5'-dimethoxytrityl base-protected nucleoside-2-cyanoethyl-N,N-diisopropylphosphoramidites and protected nucleosides linked to controlled-pore glass supports on a 0.2 micro mol scale, according to protocols supplied by Applied Biosystems Inc.

Alternatively, the oligonucleotide sequences may be prepared by manual methods as described by Atkinson and Smith in 'Oligonucleotide Synthesis, a Practical Approach' (M. T. Gait, Editor, IRL Press, Oxford, Washington D.C., pages 35–81).

In detail, the preparation of the oligonucleotide sequences by use of the Applied Biosystems 380A DNA synthesiser was effected as follows:

Each oligonucleotide, after cleavage from the solid support and removal of all protecting groups, was dissolved in water (1 ml). A solution of 3M sodium acetate (pH5.6; 40 μl) and ethanol (1 ml) was added to the oligonucleotide solutions (400 μl) and the mixtures stored at −70° C. for 20 hours. The resulting precipitates were collected by centrifugation (13,000 rpm for 10 minutes) and the pellets washed with ethanol:water (7:3) (200 μl) then dried briefly in vacuo and dissolved in water (15 μl) and 10 μl of a formamide/dye mix. (10 mM NaOH, 0.5 mM EDTA, 0.01% Bromophenol Blue, 0.01% xylene cyanol, 80% formamide.

The oligonucleotides were purified on a 10% polyacrylamide gel in 50 mM Tris-borate (pH8.3) containing 8.3M urea. Oligonucleotides of correct length were identified by UV shadowing (Narang et al, 1979 in Methods in Enzymology Vol 68, 90–98)—normally the most prominent band— excised from the gel and electroeluted in 5 mM tris-borate (pH 8.3) at 300 mV for 3–4 hours. The aqueous solutions were concentrated to about 200 μl by treatment with n-butanol (mix, spin and removal of the upper organic layer). The purified oligonucleotides were precipitated at −70° C. for 20 hours from a 0.3M sodium acetate solution by addition of ethanol (2.5 volumes).

Assembly of gene

Oligonucleotides SEQ ID No 2–SEQ ID No 17 (400 pM of each) [as defined hereinafter] were phosphorylated with T4 polynucleotide kinase (3.6 units) for 2 hours at 37° C. in 25 μl of a solution containing ATP (800 pM containing 25 pM gamma-$^{32}$P ATP), 100 μM spermidine, 20 mM $MgCl_2$, 50 mM Tris-HCl (pH9.0) and 0.1 mM EDTA. The solutions were heated at 100° C. for 5 minutes to terminate the reactions, then mixed in pairs as shown in Table 1 to give duplexes A to I (Oligonucleotides SEQ ID No 1 and SEQ ID No 18 (400 mM in 25 μl) were used unphosphorylated). 0.3M Sodium acetate (pH5.6, 200 μl) and ethanol (850 μl) were added and the duplexes precipitated at −20° C. for 20 hours. The resulting precipitates were collected by centrifugation and washed with ethanol:water (7:3) then dissolved in water (50 μl). The pairs of oligonucleotides were annealed together by first heating the solutions to 100° C. for 2 minutes in a boiling water bath. The bath was then allowed to cool slowly to 40° C. (about 4 hours). Solutions containing 3 pairs of duplexes were combined as shown (see Table 1), to give groups I to III lyophilised and dissolved in 30 μl of a solution containing T4 DNA ligase (1 unit; BRL), 50 mM Tris (pH7.6), 10 mM magnesium chloride, 5% (w/v) PEG 8000, 1 mm ATT, 1 mm DTT. (BRL, Focus Vol 8 no 1 Winter 1986) and the DNA ligated at 30° C. for 5 minutes followed by 20 hours at 16° C. 3M Sodium acetate (20 μl) and water (150 μl) was added and the product precipitated by addition of ethanol (750 μl) and cooling to −20° C. for 20 hours. The precipitate was collected by centrifugation and washed with ethanol (1 ml) then dissolved in water (15 μl) and formamide/dye mix (10 μl) and purified on a 10% polyacrylamide gel in 50 mM Tris-borate (pH8.3), 1 mM EDTA and 8.3M urea. Bands for strands of appropriate lengths (173–186 bases) were identified by autoradiography and isolated together by electroelution from a single gel slice as described above for individual oligonucleotide sequences. The DNA strands were annealed by first heating an aqueous solution (50 μl) at 100° C. for 2 minutes, then allowing it to cool to 40° C. over 4 hours.

Groups I, II and III were ligated together essentially as described for the group preparation to give as the product, the gene sequence shown in FIG. 10. After precipitation, the gene was phosphorylated with T4 polynucleotide kinase as described previously for individual oligonucleotides, then dissolved in water (20 μl).

TABLE 1

| DUPLEX | OLIGONUCLEOTIDE | NUMBER OF BASES IN TOP STRAND | NUMBER OF BASES IN BOTTOM STRAND |
|---|---|---|---|
| A | SEQ ID No 1 + SEQ ID No 2 | 62 | 64 |
| B | SEQ ID No 3 + SEQ ID No 4 | 60 | 60 |
| C | SEQ ID No 5 + SEQ ID No 6 | 48 | 51 |
| D | SEQ ID No 7 + SEQ ID No 8 | 63 | 60 |
| E | SEQ ID No 9 + SEQ ID No 10 | 63 | 63 |
| F | SEQ ID No 11 + SEQ ID No 12 | 60 | 63 |
| G | SEQ ID No 13 + SEQ ID No 14 | 63 | 60 |
| H | SEQ ID No 15 + SEQ ID No 16 | 60 | 60 |
| I | SEQ ID No 17 + SEQ ID No 18 | 55 | 53 |

TABLE 1-continued

| DUPLEX | OLIGONUCLEOTIDE | NUMBER OF BASES IN TOP STRAND | NUMBER OF BASES IN BOTTOM STRAND |
|---|---|---|---|
| I | A + B + C | 170 | 175 |
| II | D + E + F | 186 | 186 |
| III | G + H + I | 178 | 173 |

b) Cloning of the synthetic gene for human G-CSF

The synthetic gene described above, was cloned into the plasmid vector, pSTP1 (Windass et al, Nucleic Acids Research, 1983, Vol 10, p6639).

For vector preparation, 10 μg of STP1 was dissolved in water (37.5 μl) and 10×B restriction buffer (4.5 μl) (BCL). the restriction endonuclease SalI (3 μl) (BCL, 8 units/μl) was added and the mixture incubated at 37° C. for 1 hour until linearised plasmid was predominant over supercoiled and nicked circular forms. The DNA was precipitated with ethanol at 4° C. for 30 minutes, washed with ethanol:water (7:3) then dissolved in water (39.5 μl), 10×H buffer (4.5 μl) (BCL). The restriction endonuclease EcoRI (1 μl) (BCL, 90 units/μl) was added and the mixture incubated at 37° C. for 1 hour until the large EcoRI-SalI fragment was predominant. The DNA was precipitated at −20° C. for 20 hours, washed with ethanol:water (7:3) then dissolved in water (20 μl)

The large EcoRI-SalI fragment was purified on a 1% preparative agarose gel and electroeluted and precipitated as described previously, then dissolved in water (20 μl). For ligation of the synthetic gene, a mixture of vector DNA (2 μl of the EcoRI-SalI fragment solution), synthetic gene (5 μl of the aqueous solution described previously, 5×ligase buffer (6 μl −250 mM Tris pH7.6 50 mM $MgCl_2$, 25% W/V PEG8000, 5 MM ATP, 5 mM DTT exBRL) water (15 μl) and T4 DNA ligase (2 μl, 1 U/μl) was incubated at 16° C. for 4 hours. The DNA mix was used directly (either 1 μl of neat ligation mix or 2 μl of ligation mix diluted 5× with water) to transform *E. coli* strain HB101. The DNA mixture (1 or 2 μl) was added to competent *E. coli* HB101 cells (20 μl, BRL) on ice and the mixture incubated on ice for 45 min then heat shocked at 42° C. for 45 seconds. After 2 min on ice, 100 μl of SOC buffer (Bactotryptone 2%; Yeast Extract 0.5%; NaCl 10 mM; KCl 2.5 mm; $MgCl_2$, $MgSO_4$ 20 mm (10 mm each); glucose 20 mm) was added and the mixture incubated at 37° C. for 1 hour. Aliquots of suspensions were plated onto L plates with 50 μl/ml ampicillin. Transformants were screened for the presence of cloned synthetic gene by colony hybridisation analysis using standard methods described in "Molecular Cloning: A Laboratory Manual" by Maniatis et al (Cold Spring Harbor) and in UK Patent Application No 8502605. A total of 100 colonies were streaked onto filters (Schleicher and Schuell), grown at 37° C. for 20 hours, lysed and baked. The filter was hybridised at 65° C. for 20 hours with a radioactive probe prepared from oligonucleotide sequence SEQ ID No 1 by use of a random-label kit (Pharmacia). Five colonies 1–5 giving a positive hybridisation signal were grown up in L broth at 37° C. for 20 hours on a small scale (100 ml) and plasmid DNA prepared by centrifugation in a caesium chloride gradient essentially as described in "Molecular Cloning; A Laboratory Manual" by Maniatas et al (Cold Spring Harbor).

The DNA was sequenced by the standard dideoxy chain-termination method as described by Sanger et al in Proc. Nat. Acad Sci. USA 74, 5463–5467 (1977) using a Sequenase (Trade Mark) kit (United States Biochemical Corporation). Oligonucleotides SEQ ID No 19 to SEQ ID No 23 (as defined hereinafter and see Table 2) were used as sequencing primers.

TABLE 2

| CODE | PRIMING SITE |
|---|---|
| SEQ ID No 19 | 214–234 top strand |
| SEQ ID No 20 | 333–353 top strand |
| SEQ ID No 21 | 375–395 bottom strand |
| SEQ ID No 22 | 207–227 bottom strand |
| SEQ ID No 23 | 69–93 bottom strand |

The plasmid DNA from clone 5 contained the DNA sequence shown in FIG. 10. The plasmid was designated pAG88 and was used to transform competent cells of the following *E.coli* strain HB101 and CGSC 6300 (hereinafter also referred to as MSD 522) by standard procedures.

EXAMPLE 5

Preparation of M13mp18 template containing $[Ser^{17,27}]$ human G-CSF gene

The procedure for steps a) and b) in Example 4 was repeated with the following modifications:

Oligonucleotides SEQ ID Nos 24, 25, 26 and 27 (as hereinafter defined) replace SEQ ID Nos 1, 2, 3 and 4 (as hereinafter defined) respectively.

c) Cloning of the gene for $[Ser^{17,27}]$ human G-CSF into an expression vector The gene described above (see FIG. 9 and SEQ ID No. 31) was cloned into plasmid vector pICI0020. This vector is a pAT153 based plasmid in which the 651 bp EcoRI-AccI region is replaced by a 167 bp EcoRI-ClaI fragment (SEQ ID NO:30 hybridized to SEQ ID NO:48 as indicated in FIG. 5*a*) consisting of:

(1) a synthetic *E. coli* trp promoter and trp leader ribosome binding site (2) a translation initiation codon (3) a multiple restriction enzyme recognition sequence derived from M13mp18, containing sites for KpnI, BamHI, XbaI, SalI, PstI, SphI and HindIII (4) a synthetic transcription termination sequence The DNA sequence of this region is shown in FIG. 5*a*.

The pICI0020 expression vector was digested to completion with KpnI (BCL) in 10 mM Tris HCl (pH7.5), 10 mM magnesium chloride. The DNA was precipitated with ethanol at −20° C. from a solution containing 0.3M sodium acetate and then the 3'-sticky ends were removed by treatment with T4 DNA polymerase for 10 minutes at 37° C. as follows:

DNA (1 μg) in water (16 μl)

10×T4 polymerase buffer (2 μl)

0.33M Tris acetate pH7.9

0.1M Magnesium acetate 0.66M Potassium acetate 5 mM dithiothreitol 1 mg/ml bovine serum albumin (BSA PENTAX fraction V)

2 mM dNTP mixture (1 μl)

T4 DNA polymerase (1 μl; 2.5 units/μl BCL)

Water (80 μl) was added and the mixture extracted with phenol/chloroform (100 μl) and then with chloroform (100 μl). The DNA was precipitated with ethanol (250 μl) at −20° C. after addition of 3M sodium acetate (10 μl) then digested to completion with SalI (BCL) in 150 mM NaCl, 10 mM $MgCl_2$ and 10 mM Tris HCl (pH7.5). The Kpn-blunt ended to SalI vector was purified from a 0.7% agarose gel and isolated by use of Geneclean (trademark) following the manufacturer's (Bio101, USA) recommended procedure.

The synthetic gene was isolated from the pSTP1 vectors as follows. The vectors were digested with ScaI and SalI (both from BCL) in 100 mM NaCl, 10 mM $MgCl_2$ and 10 mM Tris HCl (pH7.5). The 530 bp fragment was purified from a 0.7% agarose gel and isolated by use of Geneclean (trademark) following the manufacturer's (Bio101) recommended procedure.

For ligation, a mixture of the ScaI-SalI gene fragment (50 ng) and the pICI0020 vector fragment (100 ng) in 20 μl of a solution containing 50 mM Tris HCl (pH7.6), 10 mM $MgCl_2$, 1 mM ATP, 1 mM DTT, 5% w/v PEG 8000 and T4 DNA ligase (2 units; BRL) were incubated at 16° C. for 20 hours. The resulting mixture was used to transform competent *E. coli* HB101 cells (as supplied by BRL) as described herein. Transformants were selected for by growth on L-agar plates containing 50 μg/ml ampicillin and screened for the presence of the gene by colony hybridisation with a $^{32}P$ labelled probe (SEQ ID No 24) as described herein. Plasmid DNA was prepared from 6 positively hybridising colonies, purified by centrifugation in a caesium chloride gradient and the sequence confirmed by dideoxy sequencing as described herein.

The plasmid containing this gene was designated pICI 1080.

d) subcloning of an expression cassette containing a gene for $[Ser^{17,27}]$G-CSF into M13mp18.

The following Subcloning was effected to provide a starting point for preparation of the G-CSF derivatives detailed in Examples 3–8.

Plasmid DNA from pICI1080 (purified by caesium chloride density centrifugation) was digested to completion with EcoRI and SalI (BCL) according to the manufacturer's instructions. The small EcoRI-SalI fragment containing the trp promoter and $[Ser^{17,27}]$G-CSF gene was isolated from a 0.7% agarose gel by use of Geneclean (trademark). This fragment was cloned into an EcoRI-SalI cut M13mp18 vector (DNA supplied by Amersham International; enzymes from BCL). The fragments were ligated together in 5×BRL ligation Buffer using BRL T4 DNA ligase (described previously). The ligation mix was used to transfect competent *E. coli* TG1 cells (made competent according to the calcium chloride method of Mandel and Higa described in Molecular Cloning—A Laboratory Manual—Maniatis et al Cold Spring Harbor). The transfected cells were suspended in TY top agar containing 2% X-Gal in DMF and 200 μl log phase *E. coli* TG1 cells and were plated on 2×TY agar plates (TY top agar—8 g Bactotryptone, 5 g Yeast Extract, 5 g NaCl, 3.75 g Bacto-agar in 500 μl sterile $H_2O$; TY plates—8 g Bactotryptone, 5 g Yeast-extract, 5 g NaCl, 7.5 g Bactoagar in 500 ml sterile $H_2O$.)

Four white plaques were picked into 4×2 ml 1% *E. coli* TG1 cells in TY broth (8 g Bactotryptone, 5 g Yeast extract, 5 g NaCl in 500 ml sterile $H_2O$) aliquots and grown for 6 hours at 37° C. The 2 ml cultures were split into 0.5 ml and 1.5 ml aliquots. The bacteria were centrifuged out of solution in an Eppendorf, (trademark) microfuge and the supernatants were transferred to sterile Eppendorf (trademark) tubes. The 0.5 ml aliquots were stored at −20° C. as phage stocks. The 1.5 ml aliquots were used to prepare single stranded DNA following the method in the Amersham International M13 sequencing handbook (see below). These DNA samples were then sequenced using oligonucleotides SEQ ID No 22, SEQ ID No 23 and M13 Universal sequencing primer. The reactions were carried out using the Sequenase kit (trademark) according to the manufacturers instructions. All 4 clones had the correct DNA sequence for [$Ser^{17,27}$]G-CSF.

Large-scale single stranded DNA preparation

For single stranded DNA preparations of between 200–500 μg of DNA/ml, the method in the Amersham International "Oligonucleotide Directed Mutagenesis" was used. A detailed procedure is carried out as follows:

LARGE-SCALE SINGLE STRANDED DNA PREP:

A. Preparation of 1 ml phage stock

1. Pick a single TG1 *E. coli* colony from a glucose/minimal medium plate. Grow overnight in 10 ml 2×TY medium, shaken at 37° C. Add 10 μl to 20 ml of fresh medium, and shake at 37° C. for 3 hours.
2. Inoculate 1 ml 2×TY medium in a 10 ml sterile culture tube with 100 μl of 3 hour culture from step 1.
3. Inoculate the 1 ml culture with a recombinant plaque.
4. Incubate for 4 hours with shaking at 37° C. Transfer to a microcentrifuge tube.
5. Centrifuge for 5 minutes at ambient temperature. Pour supernatant into a fresh tube. Store overnight at 4° C. Set up an overnight culture of TG1 *E. coli* for the next stage.

B. Growth of 100 ml phage culture.

1. Inoculate 100 ml 2×TY medium with 1 ml of overnight TG1 culture and shake at 37° C. to an O.D $_{500}$ of 0.3.
2. Add the 1 ml phage supernatant from A5 (above) to the 100 ml culture.
3. Incubate for 5 hours with shaking at 37° C. Transfer to centrifuge tubes.
4. Centrifuge at 5000×g for 30 minutes at 4° C.
5. Transfer supernatant to a clean centrifuge tube. Take care not to carry over any cells (retain bacterial pellet for RF DNA preparation)
6. Add 0.2 volumes of 20% w/v PEG 6000 in 2.5M NaCl to the supernatant. Mix well and then leave to stand for 1 hour at 4° C.
7. Centrifuge at 5000×g for 20 minutes at 4° C. Discard supernatant.
8. Centrifuge at 5000×g for 5 minutes, and remove all remaining PEG/NaCl with a drawn out Pasteur pipette.
9. Resuspend the viral pellet in 500 μl water (double distilled) and transfer to a microcentrifuge tube (1.5 ml).
10. Centrifuge for 5 minutes in a microcentrifuge to remove any remaining cells. Transfer the supernatant to a fresh microcentrifuge tube.
11. Add 200 μl 20% PEG 12.5M NaCl to the supernatant mix well then leave to stand at ambient temperature for 15 minutes.
12. Centrifuge for 5 minutes, discard supernatant.
13. Centrifuge for 2 minutes. Carefully remove all traces of PEG/NaCl with a drawn out Pasteur pipette.
14. Resuspend the viral pellet in 500 μl double distilled water.
15. Add 200 μl phenol saturated with 10 mM Tris HCl pH8.0, 1 mM EDTA. Vortex briefly.
16. Stand tube for 15 minutes at room temperature.
17. Centrifuge for 3 minutes.
18. Transfer supernatant to fresh tube.
19. Repeat steps 15–18.
20. Add 500 μl chloroform and extract aqueous phase twice.
21. Add 50 μl 3M sodium acetate and 1 ml absolute ethanol. Mix.
22. Place in a dry ice and ethanol bath for 20 minutes.
23. Centrifuge for 15 minutes.
24. Wash each pellet with 1 ml –20° C. ethanol. Pour off.
25. Vacuum dry pellet and raise in 50 μl double distilled water. This procedure yields 100–200 μg single stranded DNA.

EXAMPLE 6

Preparation of pICI 1107

The procedure described in Example 5 was repeated except as follows:

The duplex I was phosphorylated with T4 polynucleotide kinase and digested with MstII (10 units) in 1×H buffer (BCL; 30 μl) for 2 hours at 37° C.

Following precipitation with ethanol, the 143 bp EcoRI-MstII fragment was purified on a 10% polyacrylamide gel containing 7M urea, isolated by electroelution from a gel slice and the DNA strands annealed as described in Example 4.

The synthetic EcoRI-MstII fragment described above was cloned into the plasmid vector pAG88 described in Example 4. For vector preparation, pAG88 (10 μg) was digested with MstII (20 units; BCL) in 1×H buffer (BCL; 100 μl) for 2 hours at 37° C. The DNA was precipitated with ethanol from 0.3M sodium acetate at –20° C. then digested with EcoRI (20 units; BCL) in 1×H buffer (BCL; 100 μl) for 2 hours at 37° C. Following precipitation with ethanol, the large EcoRI-MstII fragment was purified on a 1% agarose gel and purified using Geneclean (trademark) as described by the manufacturer (Bio 101, USA). Colonies containing the synthetic fragment were confirmed by screening with a radioactive probe prepared from oligonucleotide (SEQ ID No 1) and the correct sequence confirmed by DNA sequencing as described in Example 5 (above). The plasmid containing the gene for [$Ser^{17,27}$]G-CSF was designated pICI1107.

EXAMPLE 7

Preparation of plasmid pICI 1239

The site-directed mutagenesis procedure described below was employed using the mutagenic template M13mp18 containing the gene for [$Ser^{17,27}$]G-CSF described in Example 5 or 6 (above). The mutagenic oligonucleotides used are designated SEQ ID No 28 and SEQ ID No 29 (as hereinafter defined).

The triplet ACG in SEQ ID No 28 serves to convert Gln at position 11 to Arg and the first and last AGA triplets in SEQ ID No 29 serve to convert Pro at positions 65 and 60 to Ser. The mutagenesis was carried out as described below using SEQ ID No 29 in a single priming mutagenesis. This yielded a single plaque which incorporated the Pro 60 Ser and Pro 65 Ser changes. Single stranded DNA was prepared from this plaque as described in the mutagenesis procedure described below . This DNA was used as a mutagenic template in a single priming mutagenesis using SEQ ID No 28 as mutagenic primer. This yielded >100 plaques, 3 of which were screened by DNA sequencing as previously described. All 3 had the full set of changes incorporated. Double-stranded RF DNA was prepared from one of the plaques by following the procedure for large scale preparation of single stranded DNA (step d in Example 5) to step B5. The RF DNA was extracted from the bacterial pellet by the alkali lysis procedure of Birnboim and Doly (Nucleic Acids Research (1979) 7, 1513–1523) and purified by caesium chloride density gradient centrifugation as described in "Molecular Cloning—a Laboratory Manual" by Sambrook, Fritsch and Maniatis (Cold Spring Harbor Publication). The purified RF DNA was digested with EcoRI and SalI in buffer H as described previously and the 619 bp fragment, containing the trp promoter, ribosome binding site, translation initiation codon and gene for [$Ser^{17,27}$]G-CSF isolated from a 0.7% agarose gel by use of Geneclean (TM). The fragment was ligated into an EcoRI-SalI digested pICI0020 vector, using a 2:1 molar excess of insert to vector, with T4 DNA ligase (BRL) and ligase buffer, essentially as described previously. The ligation mix was used to transform *E.Coli* strain HB101. Transformants were selected for by growth on L-agar plates containing 50 μg/ml ampicillin. Colonies were screened for the presence of the inserted DNA by restriction analysis of plasmid DNA prepared by the method of Birnboim and Doly as described in "Molecular Cloning—a Laboratory Manual" Sambrook, Fritsch and Maniatis (Cold Spring Harbor Publication). Plasmid DNA from a colony containing the expected 619 bp EcoRI-SalI insert was used to transform *E.coli* strain MSD522 and designated pICI1239.

Site-directed mutagenesis protocol

The phosphorothioate method of Eckstein and co-workers was used:

Taylor, J W et al Nucleic Acids Research (1985) Vol pp 8749–8764

Taylor, J W et al Nucleic Acids Research (1985) Vol pp 8765–8785

Nakamaye, K et al Nucleic Acids Research (1986) Vol pp 9679–9698

Sayers, J R et al Nucleic Acids Research (1988) Vol pp 791–802

The procedure can be carried out using a kit supplied by Amersham International. The method is outlined below and incorporates changes to the original method with regard to the use of more than one mutagenic oligonucleotide and the incubation temperature for oligonucleotides of greater than 30 bases in length.

1. Annealing mutant oligonucleotide to single stranded DNA template:

| | |
|---|---|
| Single stranded DNA template (1 μg/μl) | 5 μl |
| Phosporylated mutagenic oligonculeotide (1.6 pmol/1 μl) | 2.5 μl |
| Buffer 1 | 3.5 μl |
| Water | 6 μl |

(Where two mutagenic oligonucleotides were used simultaneously, 2.5 μl (1.6 pmole/1 μl) of each phosporylated oligonucleotide was added to 5 μl single stranded DNA template (1 μg/μl) in 3.5 μl Buffer 1 and 3.5 μl water. Where 3 mutagenic oligonucleotides were used 2.5 μl (1.6 pmol/μl) of each phosporylated oligonucleotide was added to 5 μl single stranded DNA (1 μg/μl in 3.5 μl Buffer 1 and 1 μl water). The above ingredients were placed in a capped tube in a 70° C. water bath for 3 minutes if the oligonucleotide was <30 bases in length or in a boiling water bath for 3 minutes if the oligonucleotide was >30 bases in length. The tube was then placed in a 37° C. water bath for 30 minutes.

2. Synthesis and ligation of mutant DNA strand:

| To the annealing reaction were added | |
|---|---|
| $MgCl_2$ solution | 5 μl |
| Nucleotide mix 1 | 19 μl |
| (contains dCTP alpha S) | |
| water | 6 μl |
| Klenow fragment (6 units) | 1.5 μl |
| T4 DNA ligase (5 units) | 2 μl |

The above ingredients were placed in a 16° C. water-bath and left overnight.

3. Removal of single stranded (non-mutant) DNA using disposable centrifugal filter units.

To the reaction from Step 2 the following ingredients were added:

| | |
|---|---|
| Water | 170 μl |
| 5 M NaCl | 30 μl |

The 250 μl sample was added to the top half of the filter unit and centrifuged at 1500 rpm for 10 minutes at room temperature in a SORVALL RT6000B bench top centrifuge using a SORVALL H1000B swing out rotor. Sample passes through two nitrocellulose membranes which bind the single stranded DNA leaving the double stranded DNA to pass through to the collection tube below. 100 μl of 500 mM NaCl were added and respun for 10 minutes to wash through any remaining RF DNA.

The following ingredients were added to the filtrate:

| | |
|---|---|
| 3 M Sodium Acetate (pH 6.0) | 28 μl |
| Cold Ethanol (−20° C.) | 700 μl |

The mixture was placed in a dry ice and ethanol bath for 20 minutes and centrifuged in an Eppendorf microfuge for 15 minutes. The pellet was then resuspended in 10 μl buffer 2.

4. Nicking of the non-mutant strand using Nci I.

To the reaction mix from step 3, was added 65 μl Buffer 3 and 8 units Nci I (1 μl). The mixture was placed in a 37° C. water bath for 90 minutes.

5. Digestion of non-mutant strand using exonuclease III

To the reaction mix from step 4 was added

| | |
|---|---|
| 500 mM NaCl | 12 μl |
| Buffer 4 | 10 μl |
| Exonuclease III (50 units) | 2 μl |

The mixture was placed in a 37° C. water bath and incubated for 30 minutes at 37° C., 50 units of exonuclease III will digest approximately 3,000 bases in 30 minutes). The mixture was then placed in a 70° C. water bath for 15 minutes to inactivate the enzymes.

6. Repolymerisation and ligation of the gapped DNA.

To the reaction mix from step 5 was added

| | |
|---|---|
| nucleotide mix 2 | 13 μl |
| $MgCl_2$ solution | 5 μl |
| DNA polymerase I (4 Units) | 1 μl |
| T4 DNA ligase (2.5 units) | 1 μl |

The mixture was placed in a 16° C. bath for 3 hours.

7. Transformation of competent host *E. coli* TG1 cells with the DNA: 300 μl of freshly prepared competent *E. coli* TG1 cells (prepared following the method of Mandel and Higa)

were transformed with 20 $\mu$l of the reaction mix from step 6 (in duplicate).

The transformants were plated out in a lawn of log phase TG1 cells in TY Top agar on TY plates and incubated overnight at 37° C.

The *E. coli* strain TG1 is freely available from for example the *E. coli* Genetic Stock Centre, Yale University, USA and from Amersham International plc, Amersham Place, Little Chalfont, Amersham, Buckinghamshire HP7 9NA, England as supplied in their "in vitro" mutagenesis system, oligonucleotide directed kit (Product code RPN 1523).

EXAMPLE 8

Preparation of plasmid pICI 1295 (also referred to as pCG300)

(a) Production of pCG54 from pICI1079 pICI1079 is an ampicillin resistant, pAT153-derived plasmid containing the following elements between the EcoRI and StyII restriction sites:

(i) a CI857 from phage λ;

(ii) a $\lambda P_L$ promoter;

(iii) a synthetic ribosome binding site;

(iv) a synthetic interferon $\alpha_2$ gene sequence;

(v) a synthetic transcription terminator sequence, derived from phage T4, between the SalI and StyI restriction sites. The DNA sequence of this transcription terminator is shown in FIG. 1(*b*) and SEQ ID NO:52 (hybridized as shown in FIG. 1(*b*)

pICI1079 is illustrated in FIG. 6.

pICI1079 has been deposited under the Budapest Treaty, at the National Collections of Industrial and Marine Bacteria Limited (NCIMB), 23 St. Machar Drive, Aberdeen, AB2 1RY, Scotland, UK. (NCIMB No 40370, date of deposit 19 Feb. 1991).

pCG54 was constructed in order to make available an expression vector containing the same promoter, ribosome binding site and transcription terminator sequences as above, ie: $\lambda_L$, RBS7 and T4, but lacking gene sequence encoding for production of a specific protein. Such a construct would provide the facility of a basic expression vector containing essential elements allowing transcription and translation for production of any protein of interest which could be introduced into this vector by subsequent cloning events.

Construction of the vector was initiated by restriction endonuclease cleavage of pICI1079 at its respective EcoRI and SalI sites. This cleavage step released a vector fragment containing the pICI1079 backbone complete with genes for plasmid replication and antibiotic resistance functions, plus the T4 transcription terminator sequence. The fragment was isolated by agarose gel purification steps using Geneclean for final purification of the DNA fragment.

To this vector fragment a second smaller DNA fragment of approximately 1.2 Kb in size was introduced. This second fragment may be obtained, for example by DNA synthesis or by site directed or PCR mutagenesis of the small EcoRI-SalI restriction fragment obtained from pICI1079 as described above. This second fragment contained exactly equivalent promoter and ribosome binding site sequences as originally present in pICI1079 and additionally had EcoRI and SalI sites available at its 5' and 3' termini respectively, so providing compatible termini for ligation to the pICI1079 fragment. A ligation reaction in the presence of Gibco-BRL enzyme T4 DNA ligase and its respective buffer, resulted in the formation of the construct pCG54.

Clones containing this construct were originally isolated following transformation of an aliquot of the ligation reaction mixture into *E.coli* competent cells of strain HB101.

The construct pCG54 recovered was 3.682 Kb in size and contained essential features as outlined on the map featured in FIG. 11.

(b) Production of pCG61 from pCG54 (also referred to as pICI54)

Synthetic oligonucleotide sequences were designed so as to include both the natural sequence for the T7A3 promoter and also a sequence which would provide an effective translation initiation region to enable correct processing of any polypeptide gene sequence cloned adjacent to it. A suitable candidate sequence for this latter region was identified as RBS1, the trp ribosome binding sequence. Therefore two complimentary oligonucleotides identified as SEQ ID No.38 and SEQ ID No.39 were synthesized to generate a double stranded DNA linker incorporating the T7A3 promoter and RBS1 sequences.

Oligonucleotides were prepared as 84 mers by the standard protocol using an ABI gene synthesizer. They were designed so that in the double stranded form the synthetic fragments would have restriction endonuclease sites EcoRI and KpnI at the 5' and 3' ends respectively. Due to their length the oligomers could not be purified by means of HPLC and purification was undertaken by means of acrylamide gel electrophoresis using a 10% acrylamide: 7M Urea gel.

Prior to purification, the oligomers were first checked on a sizing gel to ensure that not only are they of the correct size but that also the samples prepared contain as their greatest proportion the oligomers required and not a high contaminating proportion of smaller secondary oligonucleotides which result as by-products of synthesis.

The acrylamide gels were prepared by standard methods with ammonium persulphate and N,N,N',N'-tetramethylethylenediamine used as catalysts for gel polymerisation.

Sizing of the oligonucleotides required that they could be visualized after electropohoresis. It was therefore necessary to radioactively label the samples using $^{32}P$. This made it possible to assess sample quality following electrophoresis by way of autoradiography.

Oligonucleotide samples were supplied in a crude form unphosphorylated. This factor was made use of for radiolabelling purposes in that the samples could be 'hot' labelled at the 5' termini by phosphorylation using the enzyme T4 polynucleotide kinase.

Oligomers were provided from synthesis in an unphosphorylated form and so after purification each oligomer was individually subjected to a phosphorylation reaction in which ATP was used to phosphorylate the 5' end of each molecule in the presence of T4 polynucleotide kinase. (see Molecular Cloning: A Laboratory manual 2nd Edition, Sambrook, Fristch and Maniatis, p 5.68–5.71). Once phosphorylated the two complimentary oligonucleotides were annealed together to form the double strand DNA duplex containing the T7A3 promoter and the RBS1 sequence.

The vector molecule pCG54 was cleaved with restriction enzymes EcoRI and KpnI. On restriction digestion 2.3 kb vector fragment and a 1.1 kb fragment containing the $\lambda_{PL}$ promoter and RBS1 sequence are generated. This cloning step is planned to replace the $\lambda_L$-RBS1 sequence by EcoRI to Kpnl synthetic fragment comprising the T7A3-RBS1 sequence. The 2.3 kb vector fragment resulting from digestion of pCG54 was purified by the usual protocol using agarose gel electrophoresis and Geneclean methodology for removal of DNA from agarose fragments.

The 84 bp EcoRI-KpnI synthetic fragment was ligated into the vector molecule prepared above and the ligated DNA used to transform *E. coli* HB101 cells. Selection of positive recombinant clones was by ampicillin resistance. Following transformation a number of colonies containing recombinant plasmid were selected for screening purposes.

The synthetic fragment incorporated into the vector during cloning was of a size (84 mer) such as to make restriction analysis of recombinant plasmid DNA samples inappropriate as a simple screening method. Inserts of such a small size are not readily apparent on agarose gel electrophoresis. The fragment itself contains no internal restriction endonuclease cleavage site which could be diagnostic of its presence. Initial screening of recombinant clones was therefore by the method of colony hybridisation (see Grunstein and Hogness Proc. Natl Acad. Sci 72, 3961 (1975)). Nitrocellulose filters containing immobilized plasmid DNA from the recombinant clones were hybridised against a probe prepared by random radiolabelling of the synthetic annealed oligonucleotide SEQ ID No. 38 and SEQ ID No. 39 . The DNA was labelled using $\alpha^{32}$P-dCTP and incubation with Klenow polymerase at 37° C. for 2 hours. Recombinant colonies which generated a positive hybridisation reaction were selected for plasmid DNA preparation. Plasmid DNA was prepared in each case by a relatively large scale method incorporating CsCl gradient density centrifugation to ensure purity see "Molecular Cloning—A laboratory manual" second edition, Sambrook Fritsch and Maniatis (Cold Spring Harbor Laboratory, 1989) p1.42–1.52. Preparation of DNA by such a method ensures high quality material suitable for use in subsequent cloning manipulations and sequence analysis.

All plasmid DNA isolated from recombinant clones was included in a secondary screen by sequence analysis, to ensure that the oligonucleotide sequence at the cloning junctions and of the T7A3-RBS1 fragment itself was absolutely correct. The sequencing protocol used was that of Sequenase and the sequencing primer selected for use was for example pBR322 UP (pBR322 universal primer). Sequencing was effected using the Sanger dideoxy chain termination sequencing technique.

Clones having the correct sequence were designated as the new expression construct pCG61, and contained the T7A3 promoter, RBS1 sequence and the T4 terminator sequence (see FIG. 8).

EXAMPLE 9

PREPARATION OF RICIN A

The following illustrates the use of plasmid pICI0042 in the preparation of ricin A. A DNA sequence coding for the ricin A was inserted into plasmid pICI0042 such that it was under the control of the trp promoter. DNA sequences for ricin A are described, for example, in EP 145,111; Lamb, I. F. et al., Eur. J. Biochem., 1985, 148, 265–270; and O'Hare, M. et al., FEBS Letts., 1987, 216, 73–78. The following describes the preparation of several intermediate stages in the derivation of the particular vector used to prepare recombinant ricin A.

9.1 Synthetic oligonucleotides

Synthetic oligonucleotides were used to introduce specific DNA sequence alterations of the ricin gene. All oligonucleotides subsequently described were prepared on an Applied Biosystems 380A DNA synthesiser from 5'-dimethoxytrityl base-protected nucleoside-2-cyanoethyl-N,N-diisopropylphosphoramidites and protected nucleosides linked to controlled-pore glass supports on a 0.2 micro mol scale, according to protocols supplied by Applied Biosystems Inc.

Each oligonucleotide, after cleavage from the solid support and removal of all protecting groups, was dissolved in water (1 ml) and a measurement of absorbance at 260 nm used to determine concentration.

9.2 Enzymes

A variety of restriction endonucleases and DNA modifying enzymes were used in the manipulations described below. These were purchased from one of a number of suppliers (Amersham International, Bethesda Research Laboratories, Boehringer Mannheim or New England Biolabs) and used in accordance with the manufacturers instructions with respect to reaction conditions.

9.3 Construction of the pICI expression vectors 9.3 a) pICI0020

As mentioned in Example 5(c), plasmid vector pICI0020 is a pAT153 based plasmid in which the 651 bp EcoRI-AccI region is replaced by a 167 bp EcoRI-ClaI fragment consisting of:

(1) a synthetic *E. coli* trp promoter and trp leader ribosome binding site
(2) a translation initiation codon
(3) a multiple restriction enzyme recognition sequence derived from M13mp18, containing sites for KpnI, BamHI, XbaI, SalI, PstI, SphI and HindIII
(4) a synthetic transcription termination sequence The construction of a plasmid vector containing a synthetic trp promoter sequence is published (Windass et al Nuc. Acids Res. 10 p6639–6657, 1982). A promoter fragment was isolated from such a vector after digestion with the enzymes EcoRI and HpaI and purification of the appropriate band from an agarose gel by electro-elution (in "Molecular Cloning—A Laboratory Manual", Maniatis, Fritsch and Sambrook, published by CSH laboratory, second edition 1989 and hereinafter referred to as "Maniatis"). A pair of complementary synthetic oligonucleotides (SEQ ID NO:57) were prepared which would ligate to the HpaI end of the promoter fragment providing the natural trp leader ribosome binding site, a translation initiation codon and a 3' KpnI cloning site. These oligonuleotides were mixed in equimolar concentrations and allowed to anneal by heating to 100° C. followed by slowly cooling to room temperature.

The promoter fragment and annealed oligonucleotides were then ligated and the appropriate band isolated from a polyacrylamide gel by electroelution. This fragment was then ligated with an M13mp18 vector derivative containing the trp attenuator sequence (generated from synthetic oligonucleotides) cloned into the HindIII site and introducing an additional ClaI restriction site 3' to the attenuator. The ligated DNA was transfected into *E.coli* strain JM109 (Yanisch-Perron et al Gene, 33, p103, 1985) made competent by the $CaCl_2$ method (Maniatis, chapter 1 p82). After plating out and incubation of the plates, plaques were screened by the method of Benton and Davies (Maniatis, chapter 4 p41) using a $^{32}$P labelled probe generated by nick translation of the EcoRI-HpaI promoter fragment isolated previously. Single stranded DNA was prepared from positively hybridising plaques by a standard method (Maniatis, chapter 4 p29) and sequenced using the M13 universal primer and the Sanger dideoxy chain termination method as provided in kit form by a number of suppliers eg. Sequenase (United States Bioscience).

RF DNA was prepared from one isolate in which the promoter/ribosome binding site/attenuator sequence had been confirmed. This DNA was digested with EcoRI and ClaI and the appropriate fragment isolated from a polyacrylamide gel as above. Plasmid pAT153 was digested with the enzymes EcoRI and AccI and ligated with the isolated promoter fragment. Ligated DNA was used to transform competent *E. coli* HB101 (Bethesda Research Laboratories) and ampicillin resistant colonies selected.

Plasmid DNA from several clones was prepared and DNA sequence derived from the region between the EcoRI and ClaI sites. One clone confirmed as containing the correct promoter/attenuator region was named pICI0020.

This construction is outlined in FIG. 12.

9.3 b) pICI1079

As mentioned in Example 8(a), plasmid vector pICI1079 is an ampicillin resistant, pAT153-derived plasmid containing the following elements between the EcoRI and StyI restriction sites:

(i) a CI857 gene from phage $\lambda$;

(ii) a $\lambda P_L$ promoter;

(iii) a synthetic ribosome binding site;

(iv) a synthetic interferon $\alpha_2$ gene sequence;

(v) a synthetic transcription terminator sequence, derived from phage T4, between the SalI and StyI restriction sites. The DNA sequence of this transcription terminator is shown in FIG. 1*b*.

pICI1079 is illustrated in FIG. 6.

pICI1079 has been deposited under the Budapest Treaty. The deposit has been made at the NCIMB, 23 St Machaer Drive, Aberdeen, Scotland. The date of deposit was 19 Feb. 1991 and the number is NCIMB 40370.

This plasmid was used to provide a source of the T4 transcription terminator for the generation of the ricin A expressing clone pICI1185 (see 9.5.d below). The starting point for the generation of this plasmid was pICI1043. pICI1043 is a plasmid based on pICI0020 (see 9.3.a above) in which an expression cassette containing a $\lambda P_L$ promoter and interferon $\alpha$2 gene (Edge et al Nuc. Acids Res. 11 p6419–6435, 1983) is present between the EcoRI and SalI sites.

A complementary pair of oligonucleotides was synthesised to generate the transcription terminator from gene 32 of bacteriophage T4 with 5' SalI and 3' ShpI cohesive ends. This fragment was ligated with a plasmid fragment isolated from pICI1043 which had been digested to completion with SalI and SphI. The intermediate plasmid thus produced (pICI1078) contained both the T4 terminator and trp attenuator sequences in tandem.

A second pair of complementary oligonucleotides was then used to replace the trp attenuator sequence (and remaining part of the tetracycline resistance gene) by insertion between the SphI and StyI sites of pICI1078. A unique BamHI site was introduced within this synthetic fragment.

These manipulations are outlined in FIG. 13.

9.4 Generation of a ricin A expressing clone 9.4 a) Preparation of pUC8RA plasmid DNA A clone (pUC8RA) was generated which contains the DNA coding for ricin A. This clone contains A-chain cDNA from base number −74 in the leader sequence through to the BamHI site within the B-chain (base number 857) according to the published cDNA sequence (Lamb,I. F., Roberts,L. M., Lord,J. M. Eur. J. Biochem , 1985, 148, p265–270) in plasmid pUC8 (Vieira,J and Messing,J. Gene, 19, p259, 1982). In addition, site-directed mutagenesis has been used to generate a translation termination codon immediately 3' to the final codon of mature ricin A (as reported in O'Hare, M et al FEBS Letts, 1987, 216, p73–78). The entire A-chain coding region is included in a BamHI fragment from this clone.

A small quantity of pUC8RA plasmid DNA was obtained from the originators. For future stocks, a dilution of this DNA was used to transform into *E. coli* DH5$\alpha$ competent cells (Bethesda Research Laboratories) and an ampicillin resistant transformant selected. Plasmid DNA from this clone was prepared by a modified Birnboim-Doly procedure (Maniatis, chapter 1p25). Samples of this DNA were digested with BamHI and BanI separately and compared to corresponding digests of the original sample of DNA after electrophoresis on an agarose gel. No differences in restriction pattern were observed and, on this basis, the two DNA samples were assumed to be identical.

9.4 b) Sub-cloning into M13

BamHI digests of pUC8RA plasmid DNA and RF (replicative form) DNA from the phage M13 strain K19 (Anglian Biotechnology) were "shotgun" ligated using standard conditions (Maniatis, chapter 1p68). Control ligations were also performed. The ligated DNAs were used to transform *E. coli* strain TG1 (Gibson, 1984/Anglian) made competent by the $CaCl_2$ method (Maniatis, chapter 1p82).

The transformation frequencies indicated efficient ligation and recombinant phage were expected in the progeny. Recombinant phage were predicted to produce clear plaques on IPTG+X-gal (BRL) containing plates due to disruption of the lacZ ($\beta$-galactosidase) gene. Wild type phage produce blue plaques due to conversion of the X-gal by $\beta$-galactosidase.

Several clear plaques were picked for single strand DNA preparation. Direct gel electrophoresis of lysed phage suspensions indicated that one phage clone contained a sizeable insert which was confirmed by sequencing to be the ricin A-chain coding sequence. Only 182 bases of the mature ricin A coding sequence were confirmed but this was taken as sufficient evidence for the presence of the entire ricin A gene. This clone was named M13K19RA 9.4 c) Mutagenesis of M13Kl9RA To generate a KpnI site, compatible with pICI expression vectors, at the start of mature ricin A, the following changes (underlined) are necessary:

SEQ. ID. NO. 44

```
5' . . . GATAACAACATATTCCCCAAA . . . 3'
. . . Ricin leader sequence . . . | - - - Mature ricin A -->
```

Changed to:

SEQ. ID. No. 45

```
5' . . . GATAACAACATGGTACCCAAA . . . 3'
                 |  KpnI
                 |
        Translation initiation
```

and result in an ATG codon overlapping a KpnI site. A KpnI fragment containing ricin A can be excised from the mutant and inserted into the ICI expression vector series. Two N-terminal amino acid modifications are made (ile-phe to met-val).

The single stranded DNA prepared from M13K19RA was the template for the mutagenesis step for each mutation strategy. A single oligonucleotide (DTR16) introducing all the mutational changes for this strategy was synthesised.

SEQ. ID. NO. 46

DTR16 5' AACAACATGGTACCCAAACAA 3'

Several protocols exist for the introduction of specific DNA sequence changes by site directed mutagenesis. The procedures outlined below were achieved using the method of Eckstein et al (Nuc. Acid Res., 1985, 13 p8749–8764 and 1986, 14, p9679–9698) as provided in kit form (Amersham International) and used in accordance with the manufacturers instructions.

The principle of this method is to prime the single-stranded DNA template with the mutagenic oligonucleotide and synthesise the complementary strand incorporating dATPαS in place of dATP. Using this nucleotide results in the formation of phosphorothioate bonds which are not cleaved by certain restriction enzymes (eg. NciI). After synthesis of the second strand, NciI is used to nick the parent strand and exonuclease III added to digest back past the mutation point. DNA polymerase I then allows resynthesis of the parent strand. Consequently, the mutagenic oligonucleotide acts as a template for resynthesis and the mutation is introduced into both strands prior to transformation. Mutation frequencies up to 96% of the total progeny are claimed and screening is simply performed by picking plaques at random for sequence analysis.

In our experiments 4 out of 4 plaques picked were correctly mutated.

Having chosen one mutant (MRA16), RF DNA was prepared and checked for the presence of the newly generated restriction fragment ie KpnI.

9.4.d) Cloning, Expression and Initial Characterisation

The pICI series of expression vectors (see section 5) can accept DNA fragments cloned into a unique KpnI restriction site adjacent to the Trp promoter. The KpnI site overlaps the translation initiation codon (ATG) which is situated 8bp downstream from the Shine-Dalgarno site (AGGA) of the promoter.

Having verified the sequence of MRA16, a large scale (~5 μg RF DNA) KpnI digest was performed and the relevant ricin A coding DNA fragment isolated from an agarose gel (Nu-Sieve GTG agarose, FMC Bio-products) by phenol extraction of an excised gel slice according to the manufacturer's protocol. pICI0020 (see 9.3a) was digested with KpnI and then dephosphorylated using calf intestinal alkaline phosphatase (CIP—Boehringer Mannheim). The latter treatment prevents recircularisation of the vector upon ligation which would lead to a high proportion of parentals in the transformation progeny.

Ligations were set up with ratios of plasmid vector to isolated fragment from 8:1 (w/w) to 1:3 for the various strategies. Control ligations to test the effectiveness of phosphatase treatment, ligase activity etc., were included. The ligation conditions were appropriate for the source of T4 DNA ligase used (New England Biolabs or Amersham). Reactions were generally incubated at 15° C. overnight.

Fifty percent of each ligation (5 μl) reaction was diluted to 100 μl with 1 ×TNE (50 mM Tris, 50 mM NaCl, 1 mM EDTA) and 200 μl of competent *E.coli* DS410 added. After a standard transformation protocol (Maniatis, chapter 1p74), the cells were plated onto L agar plus streptomycin (25 μg/ml) and ampicillin (100 μg/ml) and incubated at 37° C. overnight. *E.coli* DS410 has a chromosomal streptomycin resistant gene.

The transformation plates were examined after incubation. In general, 5 to 10 times more colonies were seen in ligations compared to controls without ligase. In some cases, little difference in the number of colonies produced in the presence or absence of ligase occurred indicating incomplete digestion of the vector or poor ligase activity.

Transformants, plus the relevant controls were picked onto nitrocellulose filters placed on L agar plates for hybridisation screening (based on the method of Grunstein and Hogness as described in Maniatis, chapter 1p98). After incubation, the colonies were lysed in situ using 10% SDS and 1M NaOH, neutralised using 1M Tris (pH 7.5) and dried under vacuum at 80° C. for 2 hours.

Hybridisation probes were generated by $^{32}$p labelling of the mutational oligonucleotides using T4 polynucleotide kinase. The filters were probed at room temperature and then washed in stages up to 55–65° C. to remove non-specifically bound counts before autoradiography. Specific hybridisation indicated putative clones containing ricin A DNA.

Small scale DNA preparations (by the methods of Holmes and Quigley or Birnboim-Doly as specified in Maniatis, chapter 1p25) were made from positively hybridising clones. The DNAs were digested with the relevant restriction enzymes eg. KpnI and EcoRI/BglII, and analysed by electrophoresis on agarose gels. Vector DNAs and mutated RF DNAs were cut with the same enzymes to demonstrate the fragment sizes expected for the correct clones.

Larger scale plasmid DNA preparations (Birnboim-Doly) of each clone were used for more detailed restriction analysis, eg. ClaI, HindIII, BamHI, EcoRI/BglII, KpnI, and ScaI. On agarose gels, these digests showed the size of fragment inserted, an indication of its orientation and the gain of some unique ricin A-chain enzyme sites.

9.4.e) Expression studies

The clones positively identified by hybridisation and restriction screening were tested for expression of ricin A by SDS-PAGE analysis of total cell lysates. The standard conditions for expression studies were:

1) Inoculate 10 ml of L-broth+antibiotic(s) with a single colony and grow at 37° C. overnight with gentle shaking.
2) Take 750 μl of the L-broth overnight and pellet the cells in a microfuge (1 min at 6500 rpm).
3) Resuspend pellet in 300 μl M9 medium (Maniatis, appendix A.3)+0.02% casein hydrolysate+0.2% glucose+50μg/ml thiamine and inoculate into 10 ml of same.
4) Incubate for 7 hours or overnight at 37° C. with gentle shaking.
5) After incubation, measure $OD_{540}$, pellet the cells and resuspend to $OD_{540}$ =10 per ml in Laemmli sample buffer (Maniatis, chapter 18p53). Boil for 15 minutes.
6) Load 20 μl of total cell lysate on an SDS polyacrylamide gel, electrophorese, stain with Coomassie blue, destain and visualise.

Of the clones studied by SDS-PAGE, only 1 showed an additional band with equivalent molecular weight of ~29 KD (equivalent to that estimated for unglycosylated, mature ricin A). Gel scans indicated the expression level to be in the range of 5–10% of total cell protein. This clone was named pICI1102.

The construction of pICI1102 is outlined in FIG. 14. Results of expression studies are shown in FIGS. 15 and 16.

9.4 f) Western transfers and immunodetection of recombinant ricin A

Authenticity of recombinant ricin A-chain protein, initially observed by Coomassie blue staining of SDS-polyacrylamide gels, was confirmed by Western blotting. The protein bands were transferred to nitrocellulose filters and detected using a ricin A specific antibody followed by peroxidase labelled antiglobulins.

15% SDS-PAGE gels were run overnight at 8 mA then equilibrated for at least 30 minutes in transfer buffer.

Protein bands on the gels were then transferred to nitrocellulose membranes (Hybond-C, Amersham) electrophoretically in a Bio-Rad Trans Blot apparatus at 70 V for 3 hours. The filters could be stored, after drying, in sealed plastic bags at −20° C.

Ricin A.1 was a polyclonal antibody raised in rabbits against a synthetic peptide fragment of ricin A. Preliminary studies showed good affinity for ricin A but considerable cross-reactivity with many *E.coli* proteins. To overcome the high background caused by this cross-reactivity the antibody was pre-incubated with an *E.coli* lysate.

Thus, a 10 ml L-broth overnight culture of *E.coli* strain DS410 was centrifuged at 4000 rpm for 10 minutes to pellet the cells. The pellet was resuspended in 5 ml of bacterial buffer and sonicated at 4–6$\mu$ for 6×10 second bursts with 30 seconds cooling intervals on ice.

0.5 ml of sonicate was then mixed with 0.5 ml of ricin A.1 antiserum and incubated at room temperature for 90 minutes. Cell debris was spun down at 13000 rpm for 5 minutes and the supernate stored at −20° C.

The nitrocellulose filters from Western transfers were blocked by incubation overnight at room temperature in 5% BSA-PBS/Tween. (PBS Tween=5 ml Tween 20 per 1 litre of PBS).

Washed 3×3 minutes in PBS/Tween.

Incubated 2 hours (or overnight) at room temperature with a 1/4000 dilution of "blocked" Ricin A.1 antibody in 0.5% BSA-PBS/Tween.

Washed 3×3 minutes in PBS/Tween.

Incubated 1 hour with a 1/1000 dilution of goat anti rabbit antiserum in 0.5% BSA-PBS/Tween at room temperature.

Washed 3×3 minutes in PBS/Tween.

Incubated 1 hour with a 1/5000 dilution of rabbit peroxidase anti-peroxidase antiserum in 0.5% BSA/PBS/Tween at room temperature.

Washed 3×3 minutes in PBS/Tween.

Developed by immersion in a solution of 4-chloronaphthol (60 mg) in 20 ml methanol made to 120 ml with PBS and containing 12 $\mu$l hydrogen peroxide. The membrane was removed from the solution as soon as bands were visible, dried and photographed.

A typical Western blot analysis is shown in FIG. 17.

9.4 g) Biological assay for recombinant ricin A protein

The aim here was to establish conditions under which samples generated during the ricin A-chain purification from *E.coli* cells could be tested for biological activity in a cell-free in vitro protein synthesis assay.

Rabbit reticulocyte lysates were prepared according to the method of Allen and Schweet (J Biol Chem (1962), 237, 760–767). The assay demonstrates inhibition of protein synthesis in a cell-free system by a lack of incorporation of $^{14}$C-labelled leucine into newly synthesised protein.

9.4 g.i) The assay protocol

Stock solution: 1 mM amino acid mix minus leucine. A solution containing all L-amino acids at 1 mM except leucine (adjusted to pH7.4 with NaOH and stored at −70° C.).

Soln. A 40 mM Magnesium acetate

2M Ammonium acetate 0.2M Tris (pH 7.4 with HCl, stored 4° C.)

Soln. B

ATP (Sigma A5394) 246 mg/ml

GTP (Sigma G8752) 24.4 mg/ml

Assay mix: 1 ml Amino acid mixture 1 ml Soln. A 0.1 ml Soln. B 103 mg Creatine phosphate 1 mg Creatine kinase 510 $\mu$l $H_2O$ 600 $\mu$l (60 $\mu$Ci) L- $^{14}$C-leucine (New England Nuclear, NEC-279E)

Reaction mix: Test sample 25 $\mu$l

Assay mix 12.5 $\mu$l

Rabbit reticulocyte lysate 25 $\mu$l

Blank solution was 2 mg/ml BSA in PBS

All assays were done in duplicate 12.5 $\mu$l of assay mix placed in sterile glass tubes 25 $\mu$l of BSA in PBS added to each of first four tubes for blanks 25 $\mu$l of test samples added to rest of tubes 1 ml 0.1M KOH added to first two tubes (background blank)

Tubes equilibrated to 28° C. in a water bath

25 $\mu$l of rabbit reticulocyte lysate (allowed to thaw from liquid nitrogen temperature) were added to each tube at 20 second intervals. When first tube had incubated for 12 minutes, 1 ml 0.1M KOH was added to each tube again at 20 second intervals to allow all tubes to have 12 minutes incubation. Two drops of 20% hydrogen peroxide were added to each tube followed by 1 ml of 20% TCA.

Tubes were mixed and allowed to stand for at least 1 hour, or overnight, at 4° C. The precipitates were filtered on to 2.5 cm GFC discs, washed with 3×4 ml of 5% TCA, transferred to scintillation vials and 10 ml scintillant (Ready-Solv. MP, Beckman) added. After 1 hour the vials were shaken and counted.

9.4 g.ii)Establishment of technique for use with *E.coli* lysates 10 ml L-broth overnight cultures were grown at 37° C. 400 $\mu$l aliquots were pelleted at 13000 rpm for 30 seconds and most of the supernate decanted.

The pellets were subjected to 2 rounds of rapid freezing in dry ice/EtOH followed by thawing at 37° C. 12 $\mu$l of 25% sucrose in 50 mM Tris HCl pH8.0 were added followed by 4$\mu$l of a 10 mg/ml solution of lysozyme.

After incubation on ice for 15 minutes, 8 $\mu$l of 0.25M EDTA were added and incubation continued for 15 minutes. Lysis was brought about osmotically by diluting the samples to 400 $\mu$l with water. This procedure produced viable cell counts of 80–100 per ml.

When a 25 $\mu$l aliquot of this lysate was added into the assay reaction mix, the level of incorporation of $^{14}$C-leucine into newly synthesised protein was ~10% of the blank without lysate. This was a similar level of inhibition to that produced by 8 ng/ml ricin A. Dilutions of the *E. coli* lysate were then prepared and the assay repeated. The result clearly showed that a minimum 16-fold dilution was necessary to reduce the effect of the lysate to equal that of the blank.

In order to be as confident as possible that lysis of *E. coli* and *E. coli* lysates would not compromise ricin A toxicity, 2 control assays were performed. The first added plant-derived ricin A to a 16× diluted *E. coli* cell pellet so as to give a final concentration of 8 ng/ml in the assay mix after cell lysis. Both these controls showed no deleterious affect from the lysates or the lysis procedure on the inhibitory action of ricin A.

These techniques were used to verify the synthesis of biologically active, recombinant ricin A from pICI1102 and the clones described below.

9.4 h) DNA sequence analysis

Plasmid DNA sequencing was used to analyse pICI1102. The protocol chosen was modified from Zagursky et al (Gene Analysis Techniques Vol 2, N° 5) and involves alkaline denaturation of double stranded plasmid DNA prior to primer annealing and sequencing by a standard procedure such as that provided in kit form by several suppliers, eg. Sequenase (United States Bioscience). By using an oligonucleotide to prime at the 3' end of βlactamase and several A-chain internal primers, sequencing both strands of the promoter and ricin A gene was possible.

The initial sequencing data revealed an unexpected result in that an additional KpnI fragment was present between the promoter and ricin A coding sequence, ie: SEQ. ID. NO. 47

```
                            KpnI
                           ------
5' AAAAAGGGTATCGACATGGTACCCGGGGATCCACCTCAGGGTGG
                               KpnI
                              ------
TCTTTCACATTAGAGGATAACAACATGGTACCCAAACAATAC 3'
```

The additional KpnI fragment has come from M13K19RA and contains restriction enzyme sites plus the part of the ricin leader sequence cloned from pUC8RA. The 5' region of the ricin A chain contains the base changes induced during mutagenesis.

Study of this sequence reveals that the first translation initiation codon (ATG) is out of frame with that the ricin A coding region. Also, there is an in-frame termination codon (TAG) prior to the ricin A initiation codon and a putative Shine-Dalgarno sequence (AGGA) which could re-initiate translation from the second ATG.

Subsequent studies revealed that, surprisingly, this additional DNA fragment conferred a beneficial advantage with respect to the accumulation level of ricin A-chain in *E. coli* when compared to clones from which it had been excised.

The complete DNA sequence (SEQ ID No: 60) and the peptide sequence (FIG. 18) is dewsignated as SEQ ID No: 61 of the ricin A gene contained in pICI1102 is given in FIG. 18.

9.5. Generation of subsequent ricin A expressing clones 9.5 a) Mutation of Ricin-A clone pICI1102 to allow subcloning To subclone the two KpnI fragments from the fortuitously generated pICI 1120 in the correct orientation for ricin-A expression would be difficult. Consequently, we planned to alter the internal KpnI recognition site by a single base substitution (A to T). This would prevent KpnI cleavage at this site and allow the subcloning of a single KpnI fragment into the range of trp/RBS vectors. By substituting the adenine of the KpI recognition site (GGTACC) with thymine (ie GGTTCC) the first residue of ricin-A is unaltered (GTA/GTT =Val). ie:

```
KpnI   53bp fragment  KpnI          Ricin-A sequence          KpnI
_|_ _________  |  _  __________________ ___   |
GGTAC           ATGGTACC                       |    GGTACC
                                              TGA

changed to:

KpnI             53bp fragment     Ricin-A sequence          KpnI
_|_ _________  |  _  __________________ ___   |
GGTACC          ATGGTTCC                       |    GGTACC
                  |                           TGA
             not recognized by KnpI
```

The oligonucleotide synthesised to produce this change has the sequence:

```
                                        SEQ ID NO:54
5' ATAACAACATGGTTCCCAAACAATAC 3'
```

where the underlined base represents the mutational change.

We planned to clone the mutated ricin-A fragment into a range of trp expression vectors for comparative expression studies. Cloning into pICI0020 provides a comparison with pICI 1102 to determine the effects on expression, if any, of the single base substitution.

9.5 b) Mutagenesis

The template for mutagenesis was MRA16 which is the M13 clone containing the two KpnI fragments present in pICI 1102. After mutagenesis, isolates carrying the desired mutations were identified by random sampling and DNA sequence determination over the region to which the mutagenic oligonucleotide binds specifically.

One mutated template was named MRA22. This was analysed further by DNA sequence determination of the entire ricin-A coding sequence to verify the absence of non-specific mutations.

9.5 c) Sub-cloning

The mutated, single-stranded DNAs were used to transform competent *E. coli* TG1 cells to produce single plaques. Individual plaques were then picked and replicative form (RF, double-stranded) DNA purified by banding on caesium chloride/ethidium bromide buoyant density gradients. The purified RF DNA was digested to completion with KpnI. Cloning was achieved by "shotgun" ligation of the digested RF DNA with the appropriate KpnI cut and phosphatased expression vector or by specific ligation of the ricin-A fragment after its purification from an agarose gel. Ligated DNA was transformed into *E. coli* TG1 or HB101.

Ricin-A containing clones were identified by hybridisation screening using a $^{32}P$ labelled ricin-A probe produced by random hexanucleotide priming of a KpnI fragment isolated from another ricin A containing clone (pICI 1121). Colonies showing positive hybridisation were screened further by restriction analysis of plasmid DNA using a KpnI single digest and an EcoRI/BglII double digest. KpnI identifies the size of the inserted fragment and EcoRI/BglII determines the orientation of the fragment.

Clones confirmed as having the ricin-A fragment in the correct orientation for expression were subjected to clone selection grows and analysis by SDS-PAGE followed by Coomassie staining and Western blotting of duplicate gels. The level of ricin A accumulation in these clones was equivalent to that detected from pICI1102.

One isolate was selected and named pICII131.

9.5 d) Use of an alternative transcription terminator element.

In these experiments, the trp promoter and ricin-A fragment from pICI 1131 was excised by digestion with the enzymes EcoRI and SalI. The latter enzyme cleaves between the 3' terminus of the ricin-A coding sequence and the trpA transcription terminator. The resulting fragment was excised from an agarose gel (2% NuSieve GTCG Agarose, FMC Bioproducts) and purified by phenol and chloroform extractions followed by ethanol precipitation. The purified fragment was ligated with pICT 1079 cut with EcoRI and SalI. This latter plasmid contains the $T_4$ terminator between unique SalI and SphI sites.

Ligated DNA was used to transform competent *E. coli* HB101 (BRL) and hybridisation screening used to detect the presence of ricin-A DNA as in previous experiments. Positively hybridising clones were chosen for plasmid DNA preparation followed by restriction analysis with EcoRI and SalI together to show the presence of an appropriately sized fragment.

One isolate with the correct construction was identified and named pICI1185.

9.5 e) Generation inducible tetracycline selection vector

The clone, pICI1185, was used to produce a further construct by subcloning the expression cassette into a further vector, pICI 0042. Plasmid DNA was prepared from pICI1185 and digested with EcoRI and SphI together to excise an expression cassette containing the trp promoter/RBS1/ricin-A (MRA22) fragment/$T_4$ terminator. This fragment was isolated by the method outlined in 9.4d and ligated with pICI 0042 cut with EcoRI and SphI.

Ligated DNA was used to transform *E. coli* HB101. HB101 transformations were plated on L agar+tetracycline, and incubated at 37° C. overnight and colonies screened by hybridisation with a $^{32}P$ labelled ricin-A DNA probe.

In both cases, positively identified colonies were confirmed by restriction analysis of plasmid DNA using EcoRI/SphI and EcoRI/BglII digests. Three isolates were identified ie pICI1187.1–3.

FIG. 19 outlines the construction of pICI1185 and pICI1187.

9.5 f) Clone selection

The clones isolated were used to transform *E. coli* 71.18 and single colonies picked for clone selection studies. The resulting whole cell lysates were electrophoresed on duplicate SDS-PAGE gels, one of which was stained with Coomassie blue and the other used for Western blot analysis.

The stained gel provided minimal data on ricin-A expression due to the presence of a co-migrating protein from *E. coli* 71.18. Western blotting clearly indicated ricin-A expression in comparison to positive and negative control samples. One isolate was used in the fermentations described below.

RICIN A CHAIN FERMENTATION

Plasmid pICI 1187 was transformed into *E. coli* strain MSD68 and the resultant recombinant (MSD1051) purified and maintained on glycerol stocks at −80° C.

An aliquot of the culture was removed from stock and streaked onto agar plates of L-tetracycline to separate single colonies after overnight growth at 37° C. A single colony of MSD 1051 was removed and resuspended in 10 ml L-tetracycline broth and 100 $\mu$l immediately inoculated into each of 10 250 ml Erhlenmeyer flasks containing 75 ml L-tetracycline broth. After growth for 16 at 37° C. on a reciprocating shaker the contents of the flasks were pooled and used to inoculate a fermenter containing 20L modified LCM50 growth medium.

Composition of Modified LCM50

| | Made up of distilled water g/l |
|---|---|
| $KH_2PO_4$ | 3.0 |
| $Na_2HPO_4$ | 6.0 |
| NaCl | 0.5 |
| Casein hydrolysate (Oxoid L41) | 2.0 |
| $(NH_4)_2SO_4$ | 10.00 |
| Yeast Extract (Difco) | 20.00 |
| Glycerol | 35.00 |
| $MgSO_4.7H_2O$ | 0.5 |
| $CaCl_2.2H_2O$ | 0.03 |
| Thiamine | 0.008 |
| $FeSO_4$/Citric Acid | 0.94/0.02 |
| Trace element solution (TES) | 0.5 ml |

Fermentations were then carried out at a temperature of 37° C. and pH, controlled by automatic addition of 6M sodium hydroxide solution, of pH 6.7. The dissolved oxygen tension (dOT) set point was 50% air-saturation and was controlled by automatic adjustment of the fermenter stirrer speed. Air flow to the fermenter, initially 20 L/min, corresponding to 1 volume per volume per minute (VVM) was increased to 45 L/min when the fermenter stirrer speed approached 80–90% of its maximum.

Throughout the fermentation samples were taken for measurement of optical density ($OD_{550}$), cell dry weight and accumulation of ricin A chain within the cells. Ricin A chain accumulation was measured by scanning Coomassie blue stained SDS-PAGE gels of whole cell lysates of the sampled bacteria as is well known in the art.

4½ h after inoculation, yeast extract (Difco) solution (225 g/L) was pumped into the fermenters at a rate of 1.7 g/L/h.

After 12 h when $OD_{550}$ reached approximately 50, and before the fermentation became oxygen-limited bacteria were harvested on a Sorval RC3B centrifuge (700 g, 30 min, 4°) and accumulated protein recovered from the bacteria.

NOTE:

*E. coli* DS410 (also referred to as MSD68 herein) is well known (Dougan and Sherratt, Molecular and General Genetics, Vol 151, pl151–160, 1977) and has the published genotype $F^-$<u>ara</u> <u>azi</u> <u>ton A</u> <u>lac Y</u> <u>min Amin B</u> <u>rps L</u> <u>mal A</u> <u>xyl</u> <u>mtl</u> <u>thi</u>. This strain is freely available to the public, and moreover was deposited by the Applicants on 7 Jun. 1985, under the Budapest Treaty, with the National Collections Of Industrial & Marine Bacteria Ltd, Aberdeen, Scotland under deposition number 12100.

The cells were collected from the fermentation broth using a continuous disc stack intermittent discharge separator. The broth (50 l from 2×25 l fermentation) was initially transferred from the fermenters to a 501 trundle tank and transported to a contained system consisting of a number of holding tanks connected to the separator and homogenizer.

The trundle tank was connected to this system and the broth pumped through the centrifugal separator at a flow rate of 40 l/h. The discharge rate was adjusted so that the centrifuge supernatant was clear by visual inspection of an eyeglass in the supernatant discharge line. The supernatant was collected in a kill tank containing .201 of 0.1M sodium hydroxide sanitizing solution prior to disposal. The cells were resuspended in 40 l of Buffer A (50 mM sodium dihydrogen orthophosphate, 25 mM ethylene diamine tetra acetic acid, 5 mM benzamidine, 2 mM dithiothreitol, pH 6.3 with 5N sodium hydroxide) and prechilled to 8° C. in the solids receiver vessel. The suspended cells were then transferred back to the trundle tank via the homogenizer adjusted to a working pressure of 600 bar. The resulting homogenate (601) was chilled to <20° C. and make 0.5% with respect to polythenemine by the addition of 2.51 of a 10% (v/v) solution. The suspension was allowed to flocculate for 10 min before transfer to the Holding Tank via the centrifugal separator. The clear supernatant was then sterilized by purifying through a depth filter and a positively charged 0.2 $\mu$ membrane filter.

The sterile clarified supernatant was concentrated to a volume of 121 using aspiral cartridge cross flow filtration device and the solution brought to 40% saturation by the addition of 2.9 KG of solid ammonium sulphate crystals. The solution was allowed to flocculate by gentle stirring overnight at 15° C. and then centrifuged using the continuous flow centrifuge. The discharged slurry was stored at 70° C. until required for further processing.

The ammonium sulphate precipitate was thawed in the presence of 14 l of Buffer B (50 mM sodium dihydrogen orthophosphate, 25 mM elthylene diamine tetracetic acid, 2 mM dithiothreitol, pH 6.3 with 5N sodium hydroxide). After 30 min the suspension was clarified by centrifugation and desalted by diafiltration against 70 l of Buffer B and the conductivity checked that it had been reduced to below 3 MS/cm. The desalted solution was clarified further by centrifugation and processed immediately.

The desalted solution was slowly added to a batch chromatography tank containing 2 kg of DEAE-cellulose which had been equilibrated with 60 l of Buffer B. After stirring for 6.5 h the unbound r-ricin solution was pumped from the bottom of the tank through an 11.3 cm diam×10 cm column of packed and equilibrated DEAE-cellulose at a flow rate of 80 ml/min. The bulk of the r-ricin A did not bind and was collected in a stainless steel vessel.

The r-ricin A solution was adjusted to pH 5.5 with 1M orthophosphonic acid and applied to a 10 cm diameter×10 cm column of carboxymethyl agarose equilibrated with 10 l of Buffer C (25 mM sodium dihydrogen orthophosphate, 5 mM ethylene diamine tetra acetic acid, 2 mM dithiothreitol, pH 5.5 with 5N sodium hydroxide). The r-ricin A bound to this column and after washing with 10 l of Buffer C was eluted with Buffer D (25 mm sodium dihydrogen orthophosphate, 5 mM ethyl diamine tetracetic acid, 2 mM dithiothreitol, 100 mM sodium chloride, pH 5.5 with 5N sodium hydroxide). The pure r-ricin A eluted as a single peak which was collected and stored at 4° C. as a sterile solution until required for further processing. The r-ricin A is stable under these conditions for up to 2 months.

I claim:

1. A vector which comprises an inducible selection gene system comprising the tetA and tetR genes and an expression cassette containing a gene encoding a heterologous polypeptide in its reading frame.

2. A vector as claimed in claim 1 wherein the expression cassette includes a transcription terminator isolated from gene 32 of bacteriophage T4 which is operably linked to a gene coding for the heterologous protein.

3. A vector as claimed in claim 1 wherein the expression cassette contains a promoter which is selected from the group consisting of a trp promoter and T7A3 promoter and which is operably linked to the gene encoding the heterologous polypeptide.

4. A vector as claimed in claim 1 wherein the heterologous polypeptide is ricin A, G-CSF or a biologically active G-CSF analogue differing by one or two amino acids from naturally occurring G-CSF.

5. A vector as claimed in claim 1 which includes a DNA sequence which contains the cer sequence.

6. A vector which comprises a replicable plasmidic expression vehicle containing an expression cassette containing a promoter, an origin of replication, a DNA sequence which codes for a heterologous polypeptide, a transcription terminator isolated from gene 32 or bacteriophage T4 and operably linked to said expression cassette, and the cer sequence.

7. A replicable plasmidic expression vehicle which comprises an inducible selection gene system containing tetA and tetR genes and an expression cassette containing a DNA sequence which codes for a heterologous polypeptide wherein the tetA gene is induced in the presence of either tetracycline or a suitable analogue thereof and repressed in absence of either tetracycline or a suitable analogue thereof.

8. A bacterial transformant which contains the replicable plasmidic expression vehicle as claimed in claim 7.

9. A vector which comprises an inducible selection gene system containing tetA and tetR genes and an expression cassette containing a DNA sequence which codes for a heterologous polypeptide wherein the tetA gene is induced in the presence of either tetracycline or a suitable analogue thereof and repressed in the absence of either tetracycline or a suitable analogue thereof.

10. A vector as claimed in claim 9 wherein the heterologous protein is ricin A, G-CSF or a biologically active G-CSF analogue differing by one or two amino acids from naturally occurring G-CSF.

11. A vector as claimed in claim 9 which includes a DNA sequence which contains the cer sequence.

12. A vector according to claim 11 wherein the vector is plasmid pICI 1187.

13. A vector which comprises an inducible selection gene system containing tetA and tetR genes and a synthetic multicloning sequence placed in close proximity to the induced selection gene system wherein the tetA gene is induced in the presence of either tetracycline or a suitable analogue thereof and repressed in the absence of tetracycline or a suitable analogue thereof.

14. A vector according to claim 13 wherein the vector is plasmid pTB 351.

15. A vector as claimed in claim 13 which includes a DNA sequence which contains the cer sequence.

16. A vector as claimed in claim 15 wherein the vector is plasmid pICI 0042.

17. A bacterial transformant which contains a vector as claimed in any one of claims 1, 2, 3, 4, 5, 6, 9, 10, 11, 12, 13, 14, 15, and 16.

18. A process for producing a polypeptide comprising cultivating the bacterial transformant of claim 17 in a fermentation medium to form the polypeptide and recovering the polypeptide.

19. A process for producing a polypeptide comprising selecting the bacterial transformant of claim 17 by inducing the first gene of the selection gene system, cultivating the selected bacterial transformant in a fermentation medium under conditions which repress the first gene and which are suitable for the formation of the polypeptide and recovering the polypeptide.

* * * * *

SEQUENCE LISTING ( 1 ) GENERAL INFORMATION:

( i i i ) NUMBER OF SEQUENCES: 61

( 2 ) INFORMATION FOR SEQ ID NO:1:

( i ) SEQUENCE CHARACTERISTICS:
( A ) LENGTH: 62
( B ) TYPE: Nucleic acid
( C ) STRANDEDNESS: Single
( D ) TOPOLOGY: Linear ( x i ) SEQUENCE DESCRIPTION: SEQ ID NO:1:

AATTCAGT ACT CCA CTG GGT CCA GCA AGC TCT CTG CCG CAG TCT TTC 47

CTG CTG AAG TGT CTC 62

( 2 ) INFORMATION FOR SEQ ID NO:2:

( i ) SEQUENCE CHARACTERISTICS:
( A ) LENGTH: 64
( B ) TYPE: Nucleic acid
( C ) STRANDEDNESS: Single
( D ) TOPOLOGY: Linear ( x i ) SEQUENCE DESCRIPTION: SEQ ID NO:2:

CTG TTC GAG ACA CTT CAG CAG GAA AGA CTG CGG CAG AGA GCT TGC 45

TGG ACC CAG TGG AGT ACTG 64

( 2 ) INFORMATION FOR SEQ ID NO:3:

( i ) SEQUENCE CHARACTERISTICS:
( A ) LENGTH: 60
( B ) TYPE: Nucleic acid
( C ) STRANDEDNESS: Single
( D ) TOPOLOGY: Linear ( x i ) SEQUENCE DESCRIPTION: SEQ ID NO:3:

GAA CAG GTA CGT AAA ATT CAA GGC GAT GGT GCG GCT CTG CAG GAA 45

-continued

AAG CTG TGC GCA ACC 60

( 2 ) INFORMATION FOR SEQ ID NO:4:

( i ) SEQUENCE CHARACTERISTICS:
( A ) LENGTH: 60
( B ) TYPE: Nucleic acid
( C ) STRANDEDNESS: Single
( D ) TOPOLOGY: Linear ( x i ) SEQUENCE DESCRIPTION: SEQ ID NO:4:

TTT GTA GGT TGC GCA CAG CTT TTC CTG CAG AGC CGC ACC ATC GCC 45

TTG AAT TTT ACG TAC 60

( 2 ) INFORMATION FOR SEQ ID NO:5:

( i ) SEQUENCE CHARACTERISTICS:
( A ) LENGTH: 48
( B ) TYPE: Nucleic acid
( C ) STRANDEDNESS: Single
( D ) TOPOLOGY: Linear ( x i ) SEQUENCE DESCRIPTION: SEQ ID NO:5:

TAC AAA CTG TGC CAC CCT GAG GAA CTG GTG CTG CTC GGT CAC TCT CTG 48

( 2 ) INFORMATION FOR SEQ ID NO:6:

( i ) SEQUENCE CHARACTERISTICS:
( A ) LENGTH: 51
( B ) TYPE: Nucleic acid
( C ) STRANDEDNESS: Single
( D ) TOPOLOGY: Linear ( x i ) SEQUENCE DESCRIPTION: SEQ ID NO:6:

CGG GAT CCC CAG AGA GTG ACC GAG CAG CAC CAG TTC CTC AGG GTG 45

GCA CAG 51

( 2 ) INFORMATION FOR SEQ ID NO:7:

( i ) SEQUENCE CHARACTERISTICS:
( A ) LENGTH: 63
( B ) TYPE: Nucleic acid
( C ) STRANDEDNESS: Single
( D ) TOPOLOGY: Linear ( x i ) SEQUENCE DESCRIPTION: SEQ ID NO:7:

GGG ATC CCG TGG GCT CCA CTG AGC TCT TGC CCG TCC CAA GCT TTA 45

CAA CTG GCA GGC TGC TTG 63

( 2 ) INFORMATION FOR SEQ ID NO:8:

( i ) SEQUENCE CHARACTERISTICS:
( A ) LENGTH: 60
( B ) TYPE: Nucleic acid
( C ) STRANDEDNESS: Single
( D ) TOPOLOGY: Linear ( x i ) SEQUENCE DESCRIPTION: SEQ ID NO:8:

CTG GCT CAA GCA GCC TGC CAG TTG TAA AGC TTG GGA CGG GCA AGA 45

GCT CAG TGG AGC CCA 60

( 2 ) INFORMATION FOR SEQ ID NO:9:

( i ) SEQUENCE CHARACTERISTICS:

( A ) LENGTH: 63
( B ) TYPE: Nucleic acid
( C ) STRANDEDNESS: Single
( D ) TOPOLOGY: Linear ( x i ) SEQUENCE DESCRIPTION: SEQ ID NO:9:

AGC CAG CTG CAC TCC GGT CTG TTC CTG TAC CAG GGT CTG CTG CAG 45

GCT CTA GAA GGC ATC TCT 63

( 2 ) INFORMATION FOR SEQ ID NO:10:

( i ) SEQUENCE CHARACTERISTICS:
( A ) LENGTH: 63
( B ) TYPE: Nucleic acid
( C ) STRANDEDNESS: Single
( D ) TOPOLOGY: Linear ( x i ) SEQUENCE DESCRIPTION: SEQ ID NO:10:

TTC AGG AGA GAT GCC TTC TAG AGC CTG CAG CAG ACC CTG GTA CAG 45

GAA CAG ACC GGA GTG CAG 63

( 2 ) INFORMATION FOR SEQ ID NO:11:

( i ) SEQUENCE CHARACTERISTICS:
( A ) LENGTH: 60
( B ) TYPE: Nucleic acid
( C ) STRANDEDNESS: Single
( D ) TOPOLOGY: Linear ( x i ) SEQUENCE DESCRIPTION: SEQ ID NO:11:

CCT GAA TTG GGG CCC ACC CTG GAC ACA CTG CAG CTG GAC GTT GCC 45

GAC TTC GCT ACT ACC 60

( 2 ) INFORMATION FOR SEQ ID NO:12:

( i ) SEQUENCE CHARACTERISTICS:
( A ) LENGTH: 63
( B ) TYPE: Nucleic acid
( C ) STRANDEDNESS: Single
( D ) TOPOLOGY: Linear ( x i ) SEQUENCE DESCRIPTION: SEQ ID NO:12:

TTG CCA TAT GGT AGT AGC GAA GTC GGC AAC GTC CAG CTG CAG TGT 45

GTC CAG GGT GGG CCC CAA 63

( 2 ) INFORMATION FOR SEQ ID NO:13:

( i ) SEQUENCE CHARACTERISTICS:
( A ) LENGTH: 63
( B ) TYPE: Nucleic acid
( C ) STRANDEDNESS: Single
( D ) TOPOLOGY: Linear ( x i ) SEQUENCE DESCRIPTION: SEQ ID NO:13:

ATA TGG CAA CAG ATG GAG GAA CTG GGT ATG GCT CCG GCA CTG CAG 45

CCG ACT CAG GGT GCG ATG 63

( 2 ) INFORMATION FOR SEQ ID NO:14:

( i ) SEQUENCE CHARACTERISTICS:
( A ) LENGTH: 60
( B ) TYPE: Nucleic acid
( C ) STRANDEDNESS: Single
( D ) TOPOLOGY: Linear -continued ( x i ) SEQUENCE DESCRIPTION: SEQ ID NO:14:

TGC TGG CAT CGC ACC CTG AGT CGG CTG CAG TGC CGG AGC CAT ACC 45

CAG TTC CTC CAT CTG 60

( 2 ) INFORMATION FOR SEQ ID NO:15:

( i ) SEQUENCE CHARACTERISTICS:
( A ) LENGTH: 60
( B ) TYPE: Nucleic acid
( C ) STRANDEDNESS: Single
( D ) TOPOLOGY: Linear ( x i ) SEQUENCE DESCRIPTION: SEQ ID NO:15:

CCA GCA TTC GCC TCT GCT TTC CAG CGG CGC GCA GGC GGT GTT CTG 45

GTT GCC TCC CAT CTT 60

( 2 ) INFORMATION FOR SEQ ID NO:16:

( i ) SEQUENCE CHARACTERISTICS:
( A ) LENGTH: 60
( B ) TYPE: Nucleic acid
( C ) STRANDEDNESS: Single
( D ) TOPOLOGY: Linear ( x i ) SEQUENCE DESCRIPTION: SEQ ID NO:16:

GCT CTG AAG ATG GGA GGC AAC CAG AAC ACC GCC TGC GCG CCG CTG 45

GAA AGC AGA GGC GAA 60

( 2 ) INFORMATION FOR SEQ ID NO:17:

( i ) SEQUENCE CHARACTERISTICS:
( A ) LENGTH: 55
( B ) TYPE: Nucleic acid
( C ) STRANDEDNESS: Single
( D ) TOPOLOGY: Linear ( x i ) SEQUENCE DESCRIPTION: SEQ ID NO:17:

CAG AGC TTC CTC GAG GTG TCT TAC CGC GTT CTG CGT CAC CTG GCC 45

CAG CCG TTAG 55

( 2 ) INFORMATION FOR SEQ ID NO:18:

( i ) SEQUENCE CHARACTERISTICS:
( A ) LENGTH: 53
( B ) TYPE: Nucleic acid
( C ) STRANDEDNESS: Single
( D ) TOPOLOGY: Linear ( x i ) SEQUENCE DESCRIPTION: SEQ ID NO:18:

TCGACTTA CGG CTG GGC CAG GTG ACG CAG AAC GCG GTA AGA CAC CTC 47

GAG GAA 53

( 2 ) INFORMATION FOR SEQ ID NO:19:

( i ) SEQUENCE CHARACTERISTICS:
( A ) LENGTH: 21
( B ) TYPE: Nucleic acid
( C ) STRANDEDNESS: Single
( D ) TOPOLOGY: Linear ( x i ) SEQUENCE DESCRIPTION: SEQ ID NO:19:

TACAACTGGC AGGCTGCTTG A 21

( 2 ) INFORMATION FOR SEQ ID NO:20:

( i ) SEQUENCE CHARACTERISTICS:
( A ) LENGTH: 21
( B ) TYPE: Nucleic acid
( C ) STRANDEDNESS: Single
( D ) TOPOLOGY: Linear ( x i ) SEQUENCE DESCRIPTION: SEQ ID NO:20:

GACGTTGCCG ACTTCGCTAC T 21

( 2 ) INFORMATION FOR SEQ ID NO:21:

( i ) SEQUENCE CHARACTERISTICS:
( A ) LENGTH: 21
( B ) TYPE: Nucleic acid
( C ) STRANDEDNESS: Single
( D ) TOPOLOGY: Linear ( x i ) SEQUENCE DESCRIPTION: SEQ ID NO:21:

TGCCGGAGCC ATACCCAGTT C 21

( 2 ) INFORMATION FOR SEQ ID NO:22:

( i ) SEQUENCE CHARACTERISTICS:
( A ) LENGTH: 21
( B ) TYPE: Nucleic acid
( C ) STRANDEDNESS: Single
( D ) TOPOLOGY: Linear ( x i ) SEQUENCE DESCRIPTION: SEQ ID NO:22:

GCCTGCCAGT TGTAAAGCTT G 21

( 2 ) INFORMATION FOR SEQ ID NO:23:

( i ) SEQUENCE CHARACTERISTICS:
( A ) LENGTH: 26
( B ) TYPE: Nucleic acid
( C ) STRANDEDNESS: Single
( D ) TOPOLOGY: Linear ( x i ) SEQUENCE DESCRIPTION: SEQ ID NO:23:

GCACCATCGC CTTGAATTTT ACGTAG 26

( 2 ) INFORMATION FOR SEQ ID NO:24:

( i ) SEQUENCE CHARACTERISTICS:
( A ) LENGTH: 62
( B ) TYPE: Nucleic acid
( C ) STRANDEDNESS: Single
( D ) TOPOLOGY: Linear ( x i ) SEQUENCE DESCRIPTION: SEQ ID NO:24:

AATTCAGT ACT CCA CTG GGT CCA GCA AGC TCT CTG CCG CAG TCT TTC 47

CTG CTG AAG TCT CTC 62

( 2 ) INFORMATION FOR SEQ ID NO:25:

( i ) SEQUENCE CHARACTERISTICS:
( A ) LENGTH: 64
( B ) TYPE: Nucleic acid
( C ) STRANDEDNESS: Single
( D ) TOPOLOGY: Linear ( x i ) SEQUENCE DESCRIPTION: SEQ ID NO:25:

CTG TTC GAG AGA CTT CAG CAG GAA AGA CTG CGG CAG AGA GCT TGC 45

TGG ACC CAG TGG AGT ACTG 64

( 2 ) INFORMATION FOR SEQ ID NO:26:

( i ) SEQUENCE CHARACTERISTICS:
( A ) LENGTH: 60
( B ) TYPE: Nucleic acid
( C ) STRANDEDNESS: Single
( D ) TOPOLOGY: Linear ( x i ) SEQUENCE DESCRIPTION: SEQ ID NO:26:

GAA CAG GTA CGT AAA ATT CAA GGC AGC GGT GCG GCT CTG CAG GAA 45

AAG CTG TGC GCA ACC 60

( 2 ) INFORMATION FOR SEQ ID NO:27:

( i ) SEQUENCE CHARACTERISTICS:
( A ) LENGTH: 60
( B ) TYPE: Nucleic acid
( C ) STRANDEDNESS: Single
( D ) TOPOLOGY: Linear ( x i ) SEQUENCE DESCRIPTION: SEQ ID NO:27:

TTT GTA GGT TGC GCA CAG CTT TTC CTG CAG AGC CGC ACC GCT GCC 45

TTG AAT TTT ACG TAC 60

( 2 ) INFORMATION FOR SEQ ID NO:28:

( i ) SEQUENCE CHARACTERISTICS:
( A ) LENGTH: 29
( B ) TYPE: Nucleic acid
( C ) STRANDEDNESS: Single
( D ) TOPOLOGY: Linear ( x i ) SEQUENCE DESCRIPTION: SEQ ID NO:28:

CTT CAG CAG GAA AGA ACG CGG CAG AGA GC 29

( 2 ) INFORMATION FOR SEQ ID NO:29:

( i ) SEQUENCE CHARACTERISTICS:
( A ) LENGTH: 33
( B ) TYPE: Nucleic acid
( C ) STRANDEDNESS: Single
( D ) TOPOLOGY: Linear ( x i ) SEQUENCE DESCRIPTION: SEQ ID NO:29:

GC TTG GGA AGA GCA AGA GCT CAG AGA AGC CCA C 33

( 2 ) INFORMATION FOR SEQ ID NO:30:

( i ) SEQUENCE CHARACTERISTICS:
( A ) LENGTH: 168
( B ) TYPE: Nucleic acid
( C ) STRANDEDNESS: Single
( D ) TOPOLOGY: Linear ( x i ) SEQUENCE DESCRIPTION: SEQ ID NO:30:

AATTCTGGCA AATATTCTGA AATGAGCTGT TGACAATTAA TCATCGAACT 50

AGTTAACTAG TACGCAAGTT CACGTAAAAA GGGTATCGAC 90

AATGGTACCC GGGGATCCTC TAGAGTCGAC CTGCAGGCAT GCAAGCTTAG 140

CCCGCCTAAT GAGCGGGCTT TTTTTTAT 168

( 2 ) INFORMATION FOR SEQ ID NO:31:

( i ) SEQUENCE CHARACTERISTICS:

( A ) LENGTH: 534
( B ) TYPE: Nucleic acid
( C ) STRANDEDNESS: Single
( D ) TOPOLOGY: Linear ( x i ) SEQUENCE DESCRIPTION: SEQ ID NO:31:

```
AATTCAGT ACT CCA CTG GGT CCA GCA AGC TCT CTG CCG CAG TCT TTC CTG       50
         Thr Pro Leu Gly Pro Ala Ser Ser Leu Pro Gln Ser Phe Leu
           1               5                  10

CTG AAG TCT CTC GAA CAG GTA CGT AAA ATT CAA GGC AGC GGT GCG GCT        98
Leu Lys Ser Leu Glu Gln Val Arg Lys Ile Gln Gly Ser Gly Ala Ala
 15                  20                  25                  30

CTG CAG GAA AAG CTG TGC GCA ACC TAC AAA CTG TGC CAC CCT GAG GAA       146
Leu Gln Glu Lys Leu Cys Ala Thr Tyr Lys Leu Cys His Pro Glu Glu
                 35                  40                  45

CTG GTG CTG CTC GGT CAC TCT CTG GGG ATC CCG TGG GCT CCA CTG AGC       194
Leu Val Leu Leu Gly His Ser Leu Gly Ile Pro Trp Ala Pro Leu Ser
             50                  55                  60

TCT TGC CCG TCC CAA GCT TTA CAA CTG GCA GGC TGC TTG AGC CAG CTG       242
Ser Cys Pro Ser Gln Ala Leu Gln Leu Ala Gly Cys Leu Ser Gln Leu
         65                  70                  75

CAC TCC GGT CTG TTC CTG TAC CAG GGT CTG CTG CAG GCT CTA GAA GGC       290
His Ser Gly Leu Phe Leu Tyr Gln Gly Leu Leu Gln Ala Leu Glu Gly
     80                  85                  90

ATC TCT CCT GAA TTG GGG CCC ACC CTG GAC ACA CTG CAG CTG GAC GTT       338
Ile Ser Pro Glu Leu Gly Pro Thr Leu Asp Thr Leu Gln Leu Asp Val
 95                 100                 105                 110

GCC GAC TTC GCT ACT ACC ATA TGG CAA CAG ATG GAG GAA CTG GGT ATG       386
Ala Asp Phe Ala Thr Thr Ile Trp Gln Gln Met Glu Glu Leu Gly Met
                115                 120                 125

GCT CCG GCA CTG CAG CCG ACT CAG GGT GCG ATG CCA GCA TTC GCC TCT       434
Ala Pro Ala Leu Gln Pro Thr Gln Gly Ala Met Pro Ala Phe Ala Ser
            130                 135                 140

GCT TTC CAG CGG CGC GCA GGC GGT GTT CTG GTT GCC TCC CAT CTT CAG       482
Ala Phe Gln Arg Arg Ala Gly Gly Val Leu Val Ala Ser His Leu Gln
        145                 145                 155

AGC TTC CTC GAG GTG TCT TAC CGC GTT CTG CGT CAC CTG GCC CAG CCG       530
Ser Phe Leu Glu Val Ser Tyr Arg Val Leu Arg His Leu Ala Gln Pro
    160                 165                 170                 174

TAA G                                                                 534
```

( 2 ) INFORMATION FOR SEQ ID NO:32:

( i ) SEQUENCE CHARACTERISTICS:
( A ) LENGTH: 81
( B ) TYPE: Nucleic acid
( C ) STRANDEDNESS: Single
( D ) TOPOLOGY: Linear ( x i ) SEQUENCE DESCRIPTION: SEQ ID NO:32:

```
GAATTCAACA AAACGGTTGA CAACATGAAG TAAACACGGT ACGATGTACC      50

ACAAGTTCAC GTAAAAAGGG TATCGACAATG                           81
```

( 2 ) INFORMATION FOR SEQ ID NO:33:

( i ) SEQUENCE CHARACTERISTICS:
( A ) LENGTH: 67
( B ) TYPE: Nucleic acid
( C ) STRANDEDNESS: Single
( D ) TOPOLOGY: Linear ( x i ) SEQUENCE DESCRIPTION: SEQ ID NO:33:

```
TCGACATTAT ATTACTAATT AATTGGGGAC CCTAGAGGTC CCCTTTTTTA TTTTAAAAAG      60
```

-continued

CATGCGA 67

( 2 ) INFORMATION FOR SEQ ID NO:34:

( i ) SEQUENCE CHARACTERISTICS:
( A ) LENGTH: 118
( B ) TYPE: Nucleic acid
( C ) STRANDEDNESS: Single
( D ) TOPOLOGY: Linear ( x i ) SEQUENCE DESCRIPTION: SEQ ID NO:34:

AATTCTGGCA AATATTCTGA AATGAGCTGT TGACAATTAA TCATCGAACT 50

AGTTAACTAG TACGCAGAGC TCAATCTAGA GGGTATTAAT AATGTTCCCA 100

TTGGAGGATG ATTAAATG 118

( 2 ) INFORMATION FOR SEQ ID NO:35:

( i ) SEQUENCE CHARACTERISTICS:
( A ) LENGTH: 35
( B ) TYPE: Nucleic acid
( C ) STRANDEDNESS: Single
( D ) TOPOLOGY: Linear ( x i ) SEQUENCE DESCRIPTION: SEQ ID NO:35:

AGCTCCATAT GGTACCAGAT CTCTCGAGAG TACTT 35

( 2 ) INFORMATION FOR SEQ ID NO:36:

( i ) SEQUENCE CHARACTERISTICS:
( A ) LENGTH: 23
( B ) TYPE: Nucleic acid
( C ) STRANDEDNESS: Single
( D ) TOPOLOGY: Linear ( x i ) SEQUENCE DESCRIPTION: SEQ ID NO:36:

AGCTCAGCTG CAGCATATGG TAC 23

( 2 ) INFORMATION FOR SEQ ID NO:37:

( i ) SEQUENCE CHARACTERISTICS:
( A ) LENGTH: 72
( B ) TYPE: Nucleic acid
( C ) STRANDEDNESS: Single
( D ) TOPOLOGY: Linear ( x i ) SEQUENCE DESCRIPTION: SEQ ID NO:37:

TCGACATTAT ATTACTAATT AATTGGGGAC CCTAGAGGTC CCCTTTTTTA TTTTAAAAAG 60

CATGCGGATC CC 72

( 2 ) INFORMATION FOR SEQ ID NO:38:

( i ) SEQUENCE CHARACTERISTICS:
( A ) LENGTH: 84
( B ) TYPE: Nucleic acid
( C ) STRANDEDNESS: Single
( D ) TOPOLOGY: Linear ( x i ) SEQUENCE DESCRIPTION: SEQ ID NO:38:

AAT TCA ACA AAA CGG TTG ACA ACA TGA AGT AAA CAC GGT ACG ATG 45

TAC CAC AAG TTC ACG TAA AAA GGG TAT CGA CAA TGG TAC 84

( 2 ) INFORMATION FOR SEQ ID NO:39:

( i ) SEQUENCE CHARACTERISTICS:

-continued ( A ) LENGTH: 76
( B ) TYPE: Nucleic acid
( C ) STRANDEDNESS: Single
( D ) TOPOLOGY: Linear ( x i ) SEQUENCE DESCRIPTION: SEQ ID NO:39:

CAT TGT CGA TAC CCT TTT TAC GTG AAC TTG TGG TAC ATC GTA CCG 45

TGT TTA CTT CAT GTT GTC AAC CGT TTT GTT G 76

( 2 ) INFORMATION FOR SEQ ID NO:40:

( i ) SEQUENCE CHARACTERISTICS:
( A ) LENGTH: 24
( B ) TYPE: Nucleic acid
( C ) STRANDEDNESS: Single
( D ) TOPOLOGY: Linear ( x i ) SEQUENCE DESCRIPTION: SEQ ID NO:40:

AATTCGCATG CGGATCCATC GATC 24

( 2 ) INFORMATION FOR SEQ ID NO:41:

( i ) SEQUENCE CHARACTERISTICS:
( A ) LENGTH: 177 Amino acids
( B ) TYPE: amino acid
( C ) STRANDEDNESS: Single
( D ) TOPOLOGY: Linear ( i x ) FEATURE:
( D ) OTHER INFORMATION:
Xaa Xaa Xaa, between amino acids 35 and 36, is (Val Ser Glu)m, where m = 0 or 1.

( x i ) SEQUENCE DESCRIPTION: SEQ ID NO:41:

| | | | | | | | | | | |
|---|---|---|---|---|---|---|---|---|---|---|
| Thr | Pro | Leu | Gly | Pro | Ala | Ser | Ser | Leu | Pro | Gln |
| 1 | | | | 5 | | | | | 10 | |
| Ser | Phe | Leu | Leu | Lys | Cys | Leu | Glu | Gln | Val | Arg |
| | | | 15 | | | | | 20 | | |
| Lys | Ile | Gln | Gly | Asp | Gly | Ala | Ala | Leu | Gln | Glu |
| | | 25 | | | | | 30 | | | |
| Lys | Leu | Xaa | Xaa | Xaa | Cys | Ala | Thr | Tyr | Lys | Leu |
| | 35 | | | | | 40 | | | | |
| Cys | His | Pro | Glu | Glu | Leu | Val | Leu | Leu | Gly | His |
| 45 | | | | | 50 | | | | | 55 |
| Ser | Leu | Gly | Ile | Pro | Trp | Ala | Pro | Leu | Ser | Ser |
| | | | | 60 | | | | | 65 | |
| Cys | Pro | Ser | Gln | Ala | Leu | Gln | Leu | Ala | Gly | Cys |
| | | | 70 | | | | | 75 | | |
| Leu | Ser | Gln | Leu | His | Ser | Gly | Leu | Phe | Leu | Tyr |
| | | 80 | | | | | 85 | | | |
| Gln | Gly | Leu | Leu | Gln | Ala | Leu | Glu | Gly | Ile | Ser |
| | 90 | | | | | 95 | | | | |
| Pro | Glu | Leu | Gly | Pro | Thr | Leu | Asp | Thr | Leu | Gln |
| 100 | | | | | 105 | | | | | 110 |
| Leu | Asp | Val | Ala | Asp | Phe | Ala | Thr | Thr | Ile | Trp |
| | | | | 115 | | | | | 120 | |
| Gln | Gln | Met | Glu | Glu | Leu | Gly | Met | Ala | Pro | Ala |
| | | | 125 | | | | | 130 | | |
| Leu | Gln | Pro | Thr | Gln | Gly | Ala | Met | Pro | Ala | Phe |
| | | 135 | | | | | 140 | | | |
| Ala | Ser | Ala | Phe | Gln | Arg | Arg | Ala | Gly | Gly | Val |

-continued

| | | | | | | | | | | |
|---|---|---|---|---|---|---|---|---|---|---|
| | 145 | | | | | 150 | | | | |
| Leu | Val | Ala | Ser | His | Leu | Gln | Ser | Phe | Leu | Glu |
| 155 | | | | | 160 | | | | | 165 |
| Val | Ser | Tyr | Arg | Val | Leu | Arg | His | Leu | Ala | Gln |
| | | | | 170 | | | | | 175 | |
| Pro | | | | | | | | | | |
| 177 | | | | | | | | | | |

( 2 ) INFORMATION FOR SEQ ID NO:42:

( i ) SEQUENCE CHARACTERISTICS:
( A ) LENGTH: 46
( B ) TYPE: Nucleic acid
( C ) STRANDEDNESS: Single
( D ) TOPOLOGY: Linear ( x i ) SEQUENCE DESCRIPTION: SEQ ID NO:42:

AACAAAACGG TTGACAACAT GAAGTAAACA CGGTACGATG TACCAC 46

( 2 ) INFORMATION FOR SEQ ID NO:43:

( i ) SEQUENCE CHARACTERISTICS:
( A ) LENGTH: 22
( B ) TYPE: Nucleic acid
( C ) STRANDEDNESS: Single
( D ) TOPOLOGY: Linear ( x i ) SEQUENCE DESCRIPTION: SEQ ID NO:43:

AATTGTGAGC GGATAACAAT TT 22

( 2 ) INFORMATION FOR SEQ ID NO:44:

( i ) SEQUENCE CHARACTERISTICS:
( A ) LENGTH: 21
( B ) TYPE: Nucleic acid
( C ) STRANDEDNESS: Single
( D ) TOPOLOGY: Linear ( x i ) SEQUENCE DESCRIPTION: SEQ ID NO:44:

GATAACAACA TATTCCCCAA A 21

( 2 ) INFORMATION FOR SEQ ID NO:45:

( i ) SEQUENCE CHARACTERISTICS:
( A ) LENGTH: 21
( B ) TYPE: Nucleic acid
( C ) STRANDEDNESS: Single
( D ) TOPOLOGY: Linear ( x i ) SEQUENCE DESCRIPTION: SEQ ID NO:45:

GATAACAACA TGGTACCCAA A 21

( 2 ) INFORMATION FOR SEQ ID NO:46:

( i ) SEQUENCE CHARACTERISTICS:
( A ) LENGTH: 21
( B ) TYPE: Nucleic acid
( C ) STRANDEDNESS: Single
( D ) TOPOLOGY: Linear ( x i ) SEQUENCE DESCRIPTION: SEQ ID NO:46:

AACAACATGG TACCCAAACA A 21

( 2 ) INFORMATION FOR SEQ ID NO:47:

( i ) SEQUENCE CHARACTERISTICS:

-continued ( A ) LENGTH: 86
( B ) TYPE: Nucleic acid
( C ) STRANDEDNESS: Single
( D ) TOPOLOGY: Linear ( x i ) SEQUENCE DESCRIPTION: SEQ ID NO:47:

AAAAAGGGTA TCGACATGGT ACCCGGGGAT CCACCTCAGG GTGGTCTTTC 50

ACATTAGAGG ATAACAACAT GGTACCCAAA CAATAC 86

( 2 ) INFORMATION FOR SEQ ID NO:48:

( i ) SEQUENCE CHARACTERISTICS:
( A ) LENGTH: 166
( B ) TYPE: Nucleic acid
( C ) STRANDEDNESS: Single
( D ) TOPOLOGY: Linear ( x i ) SEQUENCE DESCRIPTION: SEQ ID NO:48:

GACCGTTTAT AAGACTTTAC TCGACAACTG TTAATTAGTA GCTTGATCAA 50

TTGATCATGC GTTCAAGTGC ATTTTTCCCA TAGCTGTTAC CATGGGCCCC 100

TAGGAGATCT CAGCTGGACG TCCGTACGTT CGAATCGGGC GGATTACTCG 150

CCCGAAAAAA AATAGC 166

( 2 ) INFORMATION FOR SEQ ID NO:49:

( i ) SEQUENCE CHARACTERISTICS:
( A ) LENGTH: 67
( B ) TYPE: Nucleic acid
( C ) STRANDEDNESS: Single
( D ) TOPOLOGY: Linear ( x i ) SEQUENCE DESCRIPTION: SEQ ID NO:49:

GTAATATAAT GATTAATTAA CCCCTGGGAT CTCCAGGGGA AAAAATAAAA 50

TTTTTCGTAC GCTTCGA 67

( 2 ) INFORMATION FOR SEQ ID NO:50:

( i ) SEQUENCE CHARACTERISTICS:
( A ) LENGTH: 35
( B ) TYPE: Nucleic acid
( C ) STRANDEDNESS: Single
( D ) TOPOLOGY: Linear ( x i ) SEQUENCE DESCRIPTION: SEQ ID NO:50:

GGTATACCAT GGTCTAGAGA GCTCTCATGA AGATC 35

( 2 ) INFORMATION FOR SEQ ID NO:51:

( i ) SEQUENCE CHARACTERISTICS:
( A ) LENGTH: 15
( B ) TYPE: Nucleic acid
( C ) STRANDEDNESS: Single
( D ) TOPOLOGY: Linear ( x i ) SEQUENCE DESCRIPTION: SEQ ID NO:51:

GTCGACGTCG TATAC 15

( 2 ) INFORMATION FOR SEQ ID NO:52:

( i ) SEQUENCE CHARACTERISTICS:
( A ) LENGTH: 72
( B ) TYPE: Nucleic acid
( C ) STRANDEDNESS: Single
( D ) TOPOLOGY: Linear ( x i ) SEQUENCE DESCRIPTION: SEQ ID NO:52:

GTAATATAAT GATTAATTAA CCCCTGGGAT CTCCAGGGGA AAAAATAAAA 50

TTTTTCGTAC GCCTAGGGGA AC 72

( 2 ) INFORMATION FOR SEQ ID NO:53:

( i ) SEQUENCE CHARACTERISTICS:
( A ) LENGTH: 24
( B ) TYPE: Nucleic acid
( C ) STRANDEDNESS: Single
( D ) TOPOLOGY: Linear ( x i ) SEQUENCE DESCRIPTION: SEQ ID NO:53:

GCGTACGCCT AGGTAGCTAG AGCC 24

( 2 ) INFORMATION FOR SEQ ID NO:54:

( i ) SEQUENCE CHARACTERISTICS:
( A ) LENGTH: 26
( B ) TYPE: Nucleic acid
( C ) STRANDEDNESS: Single
( D ) TOPOLOGY: Linear ( x i ) SEQUENCE DESCRIPTION: SEQ ID NO:54:

ATAACAACATGGTTCCCAAACAATAC 26

( 2 ) INFORMATION FOR SEQ ID NO:55:

( i ) SEQUENCE CHARACTERISTICS:
( A ) LENGTH: 177 Amino acids
( B ) TYPE: amino acid
( C ) STRANDEDNESS: Single
( D ) TOPOLOGY: Linear ( i x ) FEATURE:
( D ) OTHER INFORMATION:
Xaa Xaa Xaa, between amino acids 35 and 36, is (Val Ser Glu)m, where m = 0 or 1.

( x i ) SEQUENCE DESCRIPTION: SEQ ID NO:55:

Thr Pro Leu Gly Pro Ala Ser Ser Leu Pro Gln
1 5 10

Ser Phe Leu Leu Lys Cys Leu Glu Gln Val Arg
15 20

Lys Ile Gln Gly Asp Gly Ala Ala Leu Gln Glu
25 30

Lys Leu Xaa Xaa Xaa Cys Ala Thr Tyr Lys Leu
35 40

Cys His Pro Glu Glu Leu Val Leu Leu Gly His
45 50 55

Ser Leu Gly Ile Pro Trp Ala Pro Leu Ser Ser
60 65

Cys Pro Ser Gln Ala Leu Gln Leu Ala Gly Cys
70 75

Leu Ser Gln Leu His Ser Gly Leu Phe Leu Tyr
80 85

Gln Gly Leu Leu Gln Ala Leu Glu Gly Ile Ser
90 95

Pro Glu Leu Gly Pro Thr Leu Asp Thr Leu Gln
100 105 110

Leu Asp Val Ala Asp Phe Ala Thr Thr Ile Trp
115 120

-continued

Gln Gln Met Glu Glu Leu Gly Met Ala Pro Ala
125 130

Leu Gln Pro Thr Gln Gly Ala Met Pro Ala Phe
135 140

Ala Ser Ala Phe Gln Arg Arg Ala Gly Gly Val
145 150

Leu Val Ala Ser His Leu Gln Ser Phe Leu Glu
155 160 165

Val Ser Tyr Arg Val Leu Arg His Leu Ala Gln
170 175

Pro
177

( 2 ) INFORMATION FOR SEQ ID NO:56:

( i ) SEQUENCE CHARACTERISTICS:
( A ) LENGTH: 534
( B ) TYPE: Nucleic acid
( C ) STRANDEDNESS: Single
( D ) TOPOLOGY: Linear ( x i ) SEQUENCE DESCRIPTION: SEQ ID NO:56:

AATTCAGT ACT CCA CTG GGT CCA GCA AGC TCT CTG CCG CAG TCT TTC CTG 50
Thr Pro Leu Gly Pro Ala Ser Ser Leu Pro Gln Ser Phe Leu
1 5 10

CTG AAG TCT CTC GAA CAG GTA CGT AAA ATT CAA GGC AGC GGT GCG GCT 98
Leu Lys Ser Leu Glu Gln Val Arg Lys Ile Gln Gly Ser Gly Ala Ala
15 20 25 30

CTG CAG GAA AAG CTG TGC GCA ACC TAC AAA CTG TGC CAC CCT GAG GAA 146
Leu Gln Glu Lys Leu Cys Ala Thr Tyr Lys Leu Cys His Pro Glu Glu
35 40 45

CTG GTG CTG CTC GGT CAC TCT CTG GGG ATC CCG TGG GCT CCA CTG AGC 194
Leu Val Leu Leu Gly His Ser Leu Gly Ile Pro Trp Ala Pro Leu Ser
50 55 60

TCT TGC CCG TCC CAA GCT TTA CAA CTG GCA GGC TGC TTG AGC CAG CTG 242
Ser Cys Pro Ser Gln Ala Leu Gln Leu Ala Gly Cys Leu Ser Gln Leu
65 70 75

CAC TCC GGT CTG TTC CTG TAC CAG GGT CTG CTG CAG GCT CTA GAA GGC 290
His Ser Gly Leu Phe Leu Tyr Gln Gly Leu Leu Gln Ala Leu Glu Gly
80 85 90

ATC TCT CCT GAA TTG GGG CCC ACC CTG GAC ACA CTG CAG CTG GAC GTT 338
Ile Ser Pro Glu Leu Gly Pro Thr Leu Asp Thr Leu Gln Leu Asp Val
95 100 105 110

GCC GAC TTC GCT ACT ACC ATA TGG CAA CAG ATG GAG GAA CTG GGT ATG 386
Ala Asp Phe Ala Thr Thr Ile Trp Gln Gln Met Glu Glu Leu Gly Met
115 120 125

GCT CCG GCA CTG CAG CCG ACT CAG GGT GCG ATG CCA GCA TTC GCC TCT 434
Ala Pro Ala Leu Gln Pro Thr Gln Gly Ala Met Pro Ala Phe Ala Ser
130 135 140

GCT TTC CAG CGG CGC GCA GGC GGT GTT CTG GTT GCC TCC CAT CTT CAG 482
Ala Phe Gln Arg Arg Ala Gly Gly Val Leu Val Ala Ser His Leu Gln
145 145 155

AGC TTC CTC GAG GTG TCT TAC CGC GTT CTG CGT CAC CTG GCC CAG CCG 530
Ser Phe Leu Glu Val Ser Tyr Arg Val Leu Arg His Leu Ala Gln Pro
160 165 170 174

TAA G 534

( 2 ) INFORMATION FOR SEQ ID NO:57:

( i ) SEQUENCE CHARACTERISTICS:

-continued ( A ) LENGTH: 85
( B ) TYPE: Nucleic acid
( C ) STRANDEDNESS: Single
( D ) TOPOLOGY: Linear ( x i ) SEQUENCE DESCRIPTION: SEQ ID NO:57:

AACTAGTACG CAAGTTCACG TAAAAAGGGT ATCGACAATG GTAC 44

TTGATCATGC GTTCAAGTGC ATTTTTCCCA TAGCTGTTAC C 85

( 2 ) INFORMATION FOR SEQ ID NO:58:

( i ) SEQUENCE CHARACTERISTICS:
( A ) LENGTH: 68
( B ) TYPE: Nucleic acid
( C ) STRANDEDNESS: Single
( D ) TOPOLOGY: Linear ( i x ) FEATURE:
( D ) OTHER INFORMATION:
sequence includes attenuator ( x i ) SEQUENCE DESCRIPTION: SEQ ID NO:58:

AGCTTAGCCC GCCTAATGAG CGGGCTTTTT ATCGAT 36

ATCGGGCGGA TTACTCGCCC GAAAAATAGC TA 68

( 2 ) INFORMATION FOR SEQ ID NO:59:

( i ) SEQUENCE CHARACTERISTICS:
( A ) LENGTH: 6
( B ) TYPE: Nucleic acid
( C ) STRANDEDNESS: Single
( D ) TOPOLOGY: Linear ( x i ) SEQUENCE DESCRIPTION: SEQ ID NO:59:

A 1

TACGA 6

( 2 ) INFORMATION FOR SEQ ID NO:60:

( i ) SEQUENCE CHARACTERISTICS:
( A ) LENGTH: 1140
( B ) TYPE: Nucleic acid
( C ) STRANDEDNESS: Single
( D ) TOPOLOGY: Linear ( x i ) SEQUENCE DESCRIPTION: SEQ ID NO:60:

TTCTGGCAAA TATTCTGAAA TGAGCTGTTG ACAATTAATC ATCGAACTAG TTAACTAGTA 60

CGCAAGTTCA CGTAAAAAGG GTATCGACAA TGGTACCCGG GGATCCACCT CAGGGTGGTC 120

TTTCACATTA GAGGATAACA ACATGGTACC CAAACAATAC CCAATTATAA ACTTTACCAC 180

AGCGGGTGCC ACTGTGCAAA GCTACACAAA CTTTATCAGA GCTGTTCGCG GTCGTTTAAC 240

AACTGGAGCT GATGTGAGAC ATGAAATACC AGTGTTGCCA AACAGAGTTG GTTTGCCTAT 300

AAACCAACGG TTTATTTTAG TTGAACTCTC AAATCATGCA GAGCTTTCTG TTACATTAGC 360

CCTGGATGTC ACCAATGCAT ATGTGGTCGG CTACCGTGCT GGAAATAGCG CATATTTCTT 420

TCATCCTGAC AATCAGGAAG ATGCAGAAGC AATCACTCAT CTTTTCACTG ATGTTCAAAA 480

TCGATATACA TTCGCCTTTG GTGGTAATTA TGATAGACTT GAACAACTTG CTGGTAATCT 540

GAGAGAAAAT ATCGAGTTGG GAAATGGTCC ACTAGAGGAG GCTATCTCAG CGCTTTATTA 600

TTACAGTACT GGTGGCACTC AGCTTCCAAC TCTGGCTCGT TCCTTTATAA TTTGCATCCA 660

AATGATTTCA GAAGCAGCAA GATTCCAATA TATTGAGGGA GAAATGCGCA CGAGAATTAG 720

-continued

| | | | | | | |
|---|---|---|---|---|---|---|
| GTACAACCGG | AGATCTGCAC | CAGATCCTAG | CGTAATTACA | CTTGAGAATA | GTTGGGGGAG | 780 |
| ACTTTCCACT | GCAATTCAAG | AGTCTAACCA | AGGAGCCTTT | GCTAGTCCAA | TTCAACTGCA | 840 |
| AAGACGTAAT | GGTTCCAAAT | TCAGTGTGTA | CGATGTGAGT | ATATTAATCC | CTATCATAGC | 900 |
| TCTCATGGTG | TATAGATGCG | CACCTCCACC | ATCGTCACAG | TTTTGATTGC | TTATAAGGCC | 960 |
| AGTGGTACCC | GGGGATCCTC | TAGAGTCGAC | CTGCAGGCAT | GCAAGCTTAG | CCCGCCTAAT | 1020 |
| GAGCGGGCTT | TTTTTTATCG | ACCGATGCCC | TTGAGAGCCT | TCAACCCAGT | CAGCTCCTCC | 1080 |
| CGGTGGGCGC | GGGGCATGAC | TATCGTCGCC | GCACTTATGA | CTGTCTTCTT | TATCATGCAA | 1140 |

( 2 ) INFORMATION FOR SEQ ID NO:61:

( i ) SEQUENCE CHARACTERISTICS:
( A ) LENGTH: 267 amino acids
( B ) TYPE: amino acid
( C ) STRANDEDNESS: Single
( D ) TOPOLOGY: Linear ( x i ) SEQUENCE DESCRIPTION: SEQ ID NO:61:

| | | | | | | | | | | | | |
|---|---|---|---|---|---|---|---|---|---|---|---|---|
| Met | Val | Pro | Lys | Gln | Tyr | Pro | Ile | Ile | Asn | Phe | Thr | Thr |
| 1 | | | | 5 | | | | | 10 | | | |
| Ala | Gly | Ala | Thr | Val | Gln | Ser | Tyr | Thr | Asn | Phe | Ile | Arg |
| | 15 | | | | | 20 | | | | | 25 | |
| Ala | Val | Arg | Gly | Arg | Leu | Thr | Thr | Gly | Ala | Asp | Val | Arg |
| | | | 30 | | | | | 35 | | | | |
| His | Glu | Ile | Pro | Val | Leu | Pro | Asn | Arg | Val | Gly | Leu | Pro |
| 40 | | | | | 45 | | | | | 50 | | |
| Ile | Asn | Gln | Arg | Phe | Ile | Leu | Val | Glu | Leu | Ser | Asn | His |
| | | 55 | | | | | 60 | | | | | 65 |
| Ala | Glu | Leu | Ser | Val | Thr | Leu | Ala | Leu | Asp | Val | Thr | Asn |
| | | | | 70 | | | | | 75 | | | |
| Ala | Tyr | Val | Val | Gly | Tyr | Arg | Ala | Gly | Asn | Ser | Ala | Tyr |
| | 80 | | | | | 85 | | | | | 90 | |
| Phe | Phe | His | Pro | Asp | Asn | Gln | Glu | Asp | Ala | Glu | Ala | Ile |
| | | | 95 | | | | | 100 | | | | |
| Thr | His | Leu | Phe | Thr | Asp | Val | Gln | Asn | Arg | Tyr | Thr | Phe |
| 105 | | | | | 110 | | | | | 115 | | |
| Ala | Phe | Gly | Gly | Asn | Tyr | Asp | Arg | Leu | Glu | Gln | Leu | Ala |
| | | 120 | | | | | 125 | | | | | 130 |
| Gly | Asn | Leu | Arg | Glu | Asn | Ile | Glu | Leu | Gly | Asn | Gly | Pro |
| | | | | 135 | | | | | 140 | | | |
| Leu | Glu | Glu | Ala | Ile | Ser | Ala | Leu | Tyr | Tyr | Tyr | Ser | Thr |
| | 145 | | | | | 150 | | | | | 155 | |
| Gly | Gly | Thr | Gln | Leu | Pro | Thr | Leu | Ala | Arg | Ser | Phe | Ile |
| | | | 160 | | | | | 165 | | | | |
| Ile | Cys | Ile | Gln | Met | Ile | Ser | Glu | Ala | Ala | Arg | Phe | Gln |
| 170 | | | | | 175 | | | | | 180 | | |
| Tyr | Ile | Glu | Gly | Glu | Met | Arg | Thr | Arg | Ile | Arg | Tyr | Asn |
| | | 185 | | | | | 190 | | | | | 195 |
| Arg | Arg | Ser | Ala | Pro | Asp | Pro | Ser | Val | Ile | Thr | Leu | Glu |
| | | | | 200 | | | | | 205 | | | |
| Asn | Ser | Trp | Gly | Arg | Leu | Ser | Thr | Ala | Ile | Gln | Glu | Ser |
| | 210 | | | | | 215 | | | | | 220 | |
| Asn | Gln | Gly | Ala | Phe | Ala | Ser | Pro | Ile | Gln | Leu | Gln | Arg |
| | | | 225 | | | | | 230 | | | | |
| Arg | Asn | Gly | Ser | Lys | Phe | Ser | Val | Tyr | Asp | Val | Ser | Ile |

-continued

| | | | | | | | | | | | | |
|---|---|---|---|---|---|---|---|---|---|---|---|---|
| 235 | | | | | 240 | | | | | 245 | | |
| Leu | Ile | Pro | Ile | Ile | Ala | Leu | Met | Val | Tyr | Arg | Cys | Ala |
| | | 250 | | | | | 255 | | | | | 260 |
| Pro | Pro | Pro | Ser | Ser | Gln | Phe | | | | | | |
| | | | | 265 | | 267 | | | | | | |